(12) United States Patent
Borzilleri et al.

(10) Patent No.: US 7,547,782 B2
(45) Date of Patent: Jun. 16, 2009

(54) MET KINASE INHIBITORS

(75) Inventors: Robert M. Borzilleri, New Hope, PA (US); Xiao-Tao Chen, Furlong, PA (US); David K. Williams, Delran, NJ (US); John S. Tokarski, Princeton, NJ (US); Robert F. Kaltenbach, Holland, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 112 days.

(21) Appl. No.: 11/529,875

(22) Filed: Sep. 28, 2006

(65) Prior Publication Data

US 2007/0078140 A1  Apr. 5, 2007

Related U.S. Application Data

(60) Provisional application No. 60/722,089, filed on Sep. 30, 2005.

(51) Int. Cl.
*C07D 401/12* (2006.01)
*C07D 421/12* (2006.01)
*C07D 403/12* (2006.01)
*C07D 405/12* (2006.01)
*C07D 239/28* (2006.01)
*C07D 409/12* (2006.01)
*C07D 411/12* (2006.01)
*C07D 413/12* (2006.01)
*C07D 417/12* (2006.01)
*C07D 419/23* (2006.01)
*A61P 35/00* (2006.01)
*C07D 419/12* (2006.01)
*C07D 239/20* (2006.01)
*C07D 411/04* (2006.01)
*C07D 491/04* (2006.01)
*C07D 498/04* (2006.01)
*C07D 513/04* (2006.01)
*C07D 515/04* (2006.01)
*C07D 213/46* (2006.01)
*C07D 413/10* (2006.01)
*C07D 211/74* (2006.01)
*C07D 211/86* (2006.01)
*C07D 211/78* (2006.01)
*C07D 211/90* (2006.01)
*C07D 211/81* (2006.01)
*C07D 213/56* (2006.01)
*C07D 213/63* (2006.01)
*C01B 15/14* (2006.01)
*C01B 33/12* (2006.01)
*C07F 7/10* (2006.01)

(52) U.S. Cl. ............ 544/405; 544/298; 544/322; 544/333; 544/317; 544/328; 544/327; 544/122; 544/324; 544/91; 544/131; 546/113; 546/262; 546/14; 546/316; 546/323; 546/261; 546/268.1; 546/291; 423/325; 556/400

(58) Field of Classification Search .............. 546/268.1, 546/236.1, 113, 262; 544/238, 298, 322, 544/333, 405, 317, 328, 327, 122, 324, 127
See application file for complete search history.

(56) References Cited

U.S. PATENT DOCUMENTS 6,869,952 B2  3/2005  Bhide et al.
6,969,717 B2  11/2005 Bhide et al.

FOREIGN PATENT DOCUMENTS

EP  0151962 A2  8/1985
EP  0119774 B1  6/1987
EP  0152910 B1  7/1989

(Continued)

OTHER PUBLICATIONS

Lutterback, et al., Cancer Res. 2007; 67 (5) Mar. 1, 2007.*

(Continued)

*Primary Examiner*—Mark L Berch
*Assistant Examiner*—Cecilia M Jaisle
(74) *Attorney, Agent, or Firm*—Gary D. Greenblatt; Maureen S. Gibbons

(57) ABSTRACT

The present invention is directed to compounds having the formula I or II:

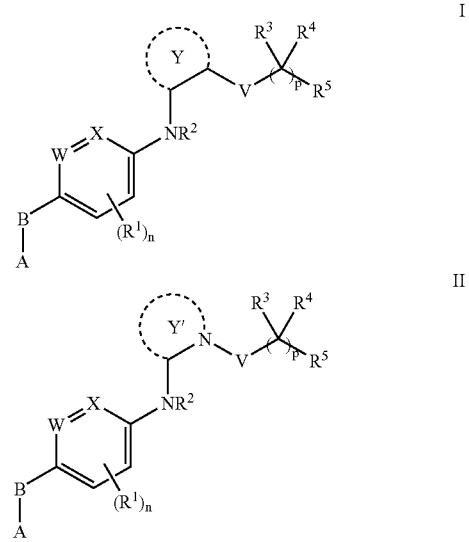

including salts thereof, and methods for using them for the treatment of cancer.

17 Claims, No Drawings

FOREIGN PATENT DOCUMENTS

| | | |
|---|---|---|
| WO | WO91/08211 | 12/1990 |
| WO | WO95/00511 | 1/1995 |
| WO | WO97/49704 A | 12/1997 |
| WO | WO99/58533 | 11/1999 |
| WO | WO00/41505 A2 | 7/2000 |
| WO | WO00/71129 A1 | 11/2000 |
| WO | WO01/57040 A1 | 8/2001 |
| WO | WO01/94353 A1 | 12/2001 |
| WO | WO02/40486 A2 | 5/2002 |
| WO | WO02/055501 A2 | 7/2002 |
| WO | WO02/081728 A2 | 10/2002 |
| WO | WO03/000194 A2 | 1/2003 |
| WO | WO03/040102 A | 5/2003 |
| WO | WO03/042172 A2 | 5/2003 |
| WO | WO03/082208 A2 | 10/2003 |
| WO | WO03/091229 A1 | 11/2003 |
| WO | WO2004/048386 A2 | 6/2004 |
| WO | WO2004/054514 | 7/2004 |
| WO | WO2004/106305 A1 | 12/2004 |
| WO | WO2005/021554 A1 | 3/2005 |
| WO | WO2005/044793 | 5/2005 |

OTHER PUBLICATIONS

Park, et al., Breast Can. Res., vol. 7, Suppl. 1, VI Madrid Breast Cancer Conf., p. S22, #P12.*
Stenina, et al., Nature Med., vol. 11, No. 4, Apr. 2005.*
Amemiya, et al., Oncology 2002;63:286-296 (Abstract).*
Mazzone, et al., The FASEB Journal vol. 20, Aug. 2006, 1611-1621.*
Park, et al., Breast Can. Res., vol. 7, Suppl. 1, VI Madrid Breast Can. Cionf. S22, #P12, Jun. 2005.*
Bardelli et al., *Concomitant activation of pathways downstream of Grb2 and Pl3-kinase is required for MET-mediated metastasis*, Oncogene (1999) 18, 1139-1146.
Barker et al., *Thienopryrdines. Part 7. Some Electrophilic Substitution Reactions of Thieno [2,3-b] pyridine isosteres of 4-oxygenaed and 2,4-dioxygenated Quinolines*, J. Chem. Research (S) 1986, pp. 122-123.
Battesti et al., *Recherches sur des pyrazolo-pyridazines et pyrimido-pyridazines. V.-Action d'hydrazines sur un derive du furanne*, Bull. Soc. Chim. Fr., 1975, 2185-2188.
Bottaro et al., *Identification of the Hepatocyte Growth Factor Receptor as the c-met Proto-Oncogene Product*, Science 251: 802-4, 1991.
Bussolino et al., *Hepatocyte Growth Factor is a Potent Antiogenic Factor Which Stimulates Endothelial Cell Motility and Growth*, J. Cell Biology, vol. 119, No. 3, Nov. 1992 629-641.
Camp et al., *Met Expression is Associated with Poor Outcome in Patients with Axillary Lymph Node Negative Breast Carcinoma*, Cancer 86, 2259-2265 (1999).
Chan et al., *Copper promoted C-N and C-O bond cross-coupling with phenyl and pyridylboronates*, Tetrahedron Lett 44 (2003) 3863-3865.
Christensen et al., *A Selective Small Molecule Inhibitor of c-Met Kinase Inhibits c-Met-Dependent Phenotypes in Vitro and Exhibits Cytoreductive Antitumor Activity in Vivo*, Cancer Research 63, 7345-7355, Nov. 1, 2003.
Cooper et al., *Amplification and overexpression of the met gene in spontaneously transformed NIH3T3 mouse fibroblasts*, EMBO Journal vol. 5, No. 10, pp. 2623-2628 (1986).
DiRenzo et al., *Overexpression and Amplification of the Met/HGF Receptor Gene during the Progression of Colorectal Cancer*, Clinical Cancer Research vol. 1, 147-154, Feb. 1995.
Dorn et al., *Unambiguous Synthesis of 4,7 Dihydro-4-exo-1H-pyrazolo [3,4-b] pyridine*, J. Prakt. Chem (1982) 324, 557-562.
Furge et al., *Met receptor tyrosine kinase: enhanced signaling through adapter proteins*, Oncogene (2000) 19, 5582-5589.
Gual et al., *Sustained recruitment of phospholipase C-γ to Gab1 is required for HGF-induced branching tubulogenesis*, Oncogene (2000) 19, 1509-1518.
Galeeva, R.N. et al., Khim. Farm. Zh. 1998, 32, 31.
Gelin, Suzanne, *Synthesis and Reactions of Some 5-Hydrozypyridazinium Hydroxide Inner Salts from 3(2H)-Furanones*, J. Org. Chem. vol. 44, No. 17, 1979, pp. 3053-3057.
Greene et al., *Protective Groups in Organic Synthesis*, Wiley, NY, (1991).
Hagmann et al., *Substituted 2-Aminopyridines as Inhibitors of Nitric Oxide Synthases*, Bioorganic & Medicinal Chem. Lett. 10 (2000) 1975-1978.
Hennequin et al., *Design and Structure-Activity Relationship of a New Class of Potent VEGF Receptor Tyrosine Kinase Inhibitors*, J. Med. Chem. 1999, 42, 5369-5389.
Howe, Robert K., *Reaction of Ethyl β-Aminocrotonate with Trichloromethanesulfenyl Chloride*, J. Org. Chem., vol. 42, No. 20, 1977.
Hunt et al., *Discovery of the Pyrrolo[2,1-f][1,2,4] triazine Nucleus as a New Kinase Inhibitor Template*, J. Med. Chem. 2004, 47, pp. 4054-4059.
Ishiyama et al., *Palladium (0)-Catalyzed Cross-Coupling Reaction of Alkoxydiboron with Haloarenes: A Direct Procedure for Arylboronic Esters*, J. Org. Chem. (1995), 60, 7508-7510.
Itoh et al., *Studies on the Chemical Synthesis of Potential Antimetabolites*, J. Heterocyclic Chem (1982) 19, 513-517.
Jiang et al., *Reduction of Stromal Fibroblast-induced Mammary Tumor Growth, by Retroviral Ribozyme Transgenes to Hepatocyte Growth Factor/Scatter Factor and its Receptor, c-MET*, Clin. Cancer Research (2003), vol. 9, 4274-4281.
Kenworthy et al., *The presence of scatter factor in patients with metastatic spread to the pleura*, Br. J. Cancer (1992), 66, 243-247.
Kermack et al., *Some Anilinopyridine Derivatives*, J. Chem. Soc. (1942) 726.
Lai et al., *Involvement of Focal Adhesion Kinase in Hepatocyte Growth Factor-induced Scatter of Madin-Darby Canine Kidney Cells*, J. Biol. Chem. (2000), vol. 275, No. 11, pp. 7474-7480.
Lee et al., *A novel germ line juxtamembrane Met mutation in human gastric cancer*, Oncogene (2000) 19, 4947-4953.
Lowe et al., *Structure-Activity Relationship of Quinazolinedione Inhibitors of Calcium-Independent Phosphodiesterase*, J. Med. Chem. 1991, 34, 624-628.
Lubensky et al., *Hereditary and Sporadic Papillary Renal Carcinomas with c-Met Mutations Share a Distinct Morphological Phenotype*, American Journal of Pathology, vol. 155, No. 2, Aug. 1999.
Masuya et al., *The tumour-stromal interaction between intramural c-Met and stromal hepatocyte growth factor associated with tumour growth and prognosis in non-small-cell lung cancer patients*, Br. J. of Cancer (2004) 90, 1555-1562.
Matsumoto et al., *Hepatocyte Growth Factor: Molecular Structure, Roles in Liver Regeneration, and Other Biological Functions*, Crit. Review 3(1,2): 27-54 (1992).
Montesano et al., *Identification of a Fibroblast-Derived Epithelial Morphogen as Hepatocyte Growth Factor*, Cell, vol. 67, 901-908, Nov. 29, 1991.
Nicolaou et al., *o-Iodoxybenzoic Acid (IBX) as a viable reagent in the manipulation of Nitrogen-and Sulfur-containing substrates; Scope, Generality, and Mechanism of IBX-Mediated Amine Oxidations and Dithiane Deprotections*, J. Am. Chem. Soc. 2004, 126, 5192-5201.
Nishikawa et al., *Preparation and Structure-Activity Relationships of 4-Substituted Amino-2-methylpyrido [3,4-d] pyrimidines as Cytokinin Analogs*, J. Agric. Food Chem. 1995, 43, 1034-138.
Park et al., *Sequence of MET protooncogene cDNA has features characteristic of the tyrosine kinase family of growth-factor receptors*, Proc. Natl. Acad. Sci, vol. 84, pp. 6379-6383, Sep. 1987.
Phuan et al., *Product Class 8: Naphthyridines*, Science of Synthesis (2005) 15, 947-985.
Radwan et al., "*Pyridazine derivatives: Synthesis and reactions of some new indeno[1,2-d]pyridazine derivatives*" Pharmazie 52 (1997) 6, pp. 483-485.
Rewcastle et al., *Tyrosine Kinase Inhibitors. 10. Isometric 4-[(3-Bromophenyl)amino]pyrido[d]-pyrimidines are Potent ATP Binding Site Inhibitors of the Tyrosine Kinase Function of the Epidermal Growth Factor Receptor*, J. Med. Chem., 1996, 39, 1823-1835.
Rogues et al., "*Etudes de la bromation du furfural en presence de chlorure d'aluminium*", Bull. Soc. Chim. Fr. (1971) 1, 242-245.

Rong et al., *Met Expression and Sarcoma Tumorigenicity*, Cancer Research 53, 5355-5360, Nov. 15, 1993.

Rong et al., *Met Proto-oncogene Product is Overexposed in Tumors of p53-deficient Mice and Tumors of Li-Fraumeni Patients*, Cancer Research 55, 1963-1970, May 1995

Sachs et al., *Essential Role of Gab1 for Signaling by the c-Met Receptor in Vivo*, J. Cell. Biol., vol. 150 (6), Sep. 18, 2000, pp. 1375-1384.

Sanghvi et al., *Synthesis and Biological Evaluation of Certain C-4 Substituted Pyrazolo [3,4-b] pyridine Nucleosides*, J. Med. Chem. (1989) 32, 945-951.

Scarpino et al., *Hepatocyte Growth Factor (HGF) Stimulates Tumour Invasiveness in Papillary Carcinoma of the Thyroid*, Journal of Pathology, 189: 570-575 (1999).

Schaeper et al., *Coupling of Gab1 to c-Met, Grb2, and Shp2 Mediates Biological Responses*, J. Cell Biology 149(7), Jun. 26, 2000, pp. 1419-1432.

Soloducho et al., *Synthesis of Some Pyrido [2,3-d] pyrimidine and Pyrido [3m2-d] pyrimidine Derivatives*, Arch. Pharm., 323, 513-515 (1990).

Sonnenberg et al., *Scatter Factor/Hepatocyte Growth Factor and Its Receptor, the c-met Tyrosine Kinase, Can Mediate a Signal Exchange between Mesenchyme and Epithelia during Mouse Development*, J. Cell. Biology, vol. 123, No. 1, Oct. 1993, pp. 223-235.

Stabile et al., *Inhibition of human non-small cell lung tumors by a c-Met antisense/U6 expression plasmid strategy*, Gene Therapy (2004) 11, 325-335 (2004).

Stella et al., *HGF: a multifuctional growth factor controlling cell scattering*, Intl. J. of Biochem & Cell Biol. 31 (1999) 1357-1362.

Stoker et al., *Scatter Factor is a fibroblast-derived modulato of epithelial cell mobility*, Nature, vol. 327, May 1987.

Stuart et al., *Hepatocyte growth factor/scatter factor-induced intracellular signaling*, Int. J. Exp. Path (2000), 81, 17-30.

Takagi et al., *Iridium-catalyzed C-H coupling reaction of heteroaromatic compounds with bis (pinacolato)diboron: regioselective synthesis of hereoarylboronates*, Tetrahedron Lett 43 (2002) 5649-5651.

Takayama et al., *Diverse tumorigenesis associated with aberrant development in mice overexpressing hepatocyte growth factor/scatter factor*, Proc. Natl. Acad. Sci. vol. 94, pp. 701-706, Jan. 1997.

Tanimura et al., *Activation of the 41/43 kDa mitogen-activated protein kinase signaling pathway is required for hepatocyte growth factor-induced cell scattering*, Oncogene (1998) 17, 57-65.

Tedder et al., *Structure-based design, synthesis and antimicrobial activity of purine derived SAH/MTA nucleosidase inhibitors*, Bioorganic & Medicinal Chemistry Letter 14 (2004, 3165-3168.

Tehrani et al., *Synthesis of 2-Acyl-3-chloropyrroles: Application to the Synthesis of the Trail Pheromone of the Ant Atta texana*, Tetrahedron 55 (1999) 4133-4152.

Temple Jr., et al., *Preparation and Properties of Some Isomeric v-Triazolopryidines, 1- and 3-Deaza-8azapurines*, J. Org. Chem., vol. 37, No. 23, 1972.

Thibault et al., *Concise and Efficient Synthesis of 4-Fluoro-1H-pyrrolo[2,3-b]pyridine*, Org. Lett. (2003) vol. 5, No. 26, 5023-5025.

Tsuge et al., *Studies of Acyl and Thiobenzoyl Isocyanates with Sulfonium Ylides and with Diazoalkanes*, Tetrahedron, vol. 29, pp. 1983-1990 (1973).

Wolfe et al., *Improved Functional Group Compatibility in the Palladium-Catalyzed Amination of Aryl Bromides*, Tetrahedron Lett (1997) 38, No. 36, 6359-6362.

Yanai et al., *Studies on the Heterocyclic Compounds* Chen. Pharm. Bull. (1977) 25, 1856-1861.

Yu et al., *A facile synthesis of 2-oxazolidinones via Hofmann rearrangement mediated by bis(trifluoroacetoxy)iodobenzene*, Tetrahedron Lett 42 (2001) 1449-1452.

Zhang et al., *Discovery and Structure- Activity Relationship of 3-Aryl-5-aryl-1,2,4-oxadiazoles as a New Series of Apoptosis Inducers and Potential Anticancer Agents*, J. Med. Chem. 2005, 48, 5215-5223.

Zhang et al., *A General Method for the Preparation of 4-and 6-Azaindoles*, J. Org. Chem. 2002, 67, 2345-2347.

Zhong et al., *Controlling the Oxygenation Level of Hemoglobin by Using a Synthetic Receptor of 2,3-Biphosphoglycerate*, Angew. Chem. Int. Ed. 2003, 42, 3005-3008.

\* cited by examiner

MET KINASE INHIBITORS

RELATED APPLICATION

This application claims priority benefit under Title 35 § 119(e) of U.S. provisional Application No. 60/722,089, filed Sep. 30, 2005, the contents of which are herein incorporated by reference.

FIELD OF THE INVENTION

This invention relates to compounds that inhibit the protein tyrosine kinase activity of growth factor receptors such as c-Met, thereby making them useful as anti-cancer agents. The pharmaceutical compositions that comprise these compounds are also useful in the treatment of diseases, other than cancer, which are associated with signal transduction pathways operating through growth factor and anti-angiogenesis receptors such as c-Met.

BACKGROUND OF THE INVENTION

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223-235, 1993; Matsumato et al., *Crit. Rev. Oncog.* 3:27-54, 1992; and Stoker et al., *Nature* 327:239-242, 1987). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell* 67:901-908, 1991), and promotion of invasion (Stella et al., *Int. J. Biochem. Cell Biol.* 12:1357-62, 1999 and Stuart et al., *Int. J. Exp. Path.* 81:17-30, 2000), all critical processes underlying metastasis. HGF has also been reported to promote angiogenesis (Bussolino et al., *J. Cell Biol.* 119:629-641, 1992). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA* 84:6379-83, 1987 and Bottaro et al., *Science* 251:802-4, 1991). The mature form of Met consists of a highly glycosylated external α-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene* 19:5582-9, 2000). These include the p85 subunit of the PI3-kinase, phospholipase Cγ (Gaul et al., *Oncogene* 19:1509-18, 2000), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J. Cell Biol.* 149:1419-32, 2000; Bardelli, et al., *Oncogene* 18:1139-46, 1999 and Sachs et al., *J. Cell Biol.* 150:1375-84, 2000). Activation of other signaling molecules has been reported in HGF stimulated cells, most notably Ras, MAP kinases, STATs, ERK-1, -2 and FAK (Tanimura et al., *Oncogene* 17:57-65, 1998; Lai et al., *J. Biol. Chem.* 275:7474-80 2000 and Furge et al., *Oncogene* 19:5582-9, 2000). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology,* 155:517-26, 1999). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.,* 63:7345-55, 2003; Lee et al., *Oncogene,* 19:4947-53, 2000 and Direnzo et al., *Clin. Cancer Res.,* 1: 147-54, 1995). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al. *Cancer Res.* 55:1963-1970, 1995; Rong et al., *Cancer Res.* 53:5355-5360, 1993; Kenworthy et al., *Br. J. Cancer* 66:243-247, 1992 and Scarpino et al. *J. Pathology* 189:570-575, 1999). TPR-Met (an activated form similar to BCR/Abl in CML) has been described and identified in human gastric carcinoma (PNAS 88:4892-6, 1991). In patients with invasive breast carcinoma and in a recent study in non small cell lung cancer patients, expression of either the receptor or ligand is a predictor of decreased survival, further linking Met to tumor progression (Camp et al., *Cancer* 86:2259-65 1999 and Masuya et al., *Br. J. Cancer,* 90:1555-62, 2004). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *PNAS,* 94:701-6, 1997) and an amplified/overexpressed Met spontaneously transforms NIH-3T3 cells (Cooper et al., *EMBO J.,* 5:2623-8, 1986).

Biological agents, such as ribozymes, antibodies and antisense RNA targeting either HGF or Met have been shown to inhibit tumorogenesis (Stabile et al., *Gene Therapy,* 11:325-35, 2004, Jiang et al., *Clin. Cancer Res,* 9:4274-81, 2003 and Genentech U.S. Pat. No. 6,214,344, 2001). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

SUMMARY

The present invention is directed to compounds that are useful for targeting Met, and therefore, useful for treating cancer. Specifically, the present invention is directed to compounds having the following Formulas I or II: A compound having the following Formula I or Formula II:

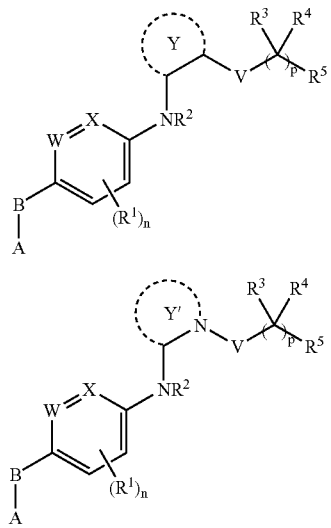

wherein
each $R^1$ is H, halogen, halogenated alkyl, cyano, $NO_2$, $OR^6$, $NR^7R^8$, alkyl, substituted alkyl, cycloalkyl, substituted cycloalkyl, aryl, substituted aryl, heteroaryl, substituted heteroaryl, aryalkyl, substituted arylalkyl, heterocycloalkyl, or substituted heterocycloalkyl;

B is O, $NR^9$, S, SO, $SO_2$, or $CR^{10}R^{11}$;

W and X are each independently C or N;

V is CO;

n is 1 to 4;

m is 1 to 4;

p is 0 to 2;

l is 1 to 2;

$R^2$ is H, alkyl, substituted alkyl, cycloalkyl, or substituted cycloalkyl;

$R^3$ and $R^4$ are independently H, halogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycloalkyl, substituted heterocycloalkyl or taken together to form a carbocyclic or heterocyclic ring of 3 to 8 atoms;

$R^5$ is $-NR^{12}R^{13}$, $-OR^{14}$, alkyl, substituted alkyl, haloalkyl, cycloalkyl, substituted cycloalkyl, aryl, substituted aryl, heteroaryl, substituted heteroaryl, aryalkyl, substituted arylalkyl, heterocycloalkyl, or substituted heterocycloalkyl;

$R^6$, $R^7$, $R^8$, and $R^9$ are each independently H, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycloalkyl or substituted heterocycloalkyl;

$R^{10}$ and $R^{11}$ are each independently H, halogen, alkyl, substituted alkyl, cycloalkyl, substituted cycloalkyl, aryl, substituted aryl, benzyl, heteroaryl, substituted heteroaryl, heterocycloalkyl, or substituted heterocycloalkyl, or taken together to form a carbocyclic or heterocyclic ring of 3 to 8 atoms;

$R^{12}$ and $R^{13}$ are each independently H, alkyl, substituted alkyl, cycloalkyl, substituted cycloalkyl, arylalkyl, substituted arylalkyl, aryl, substituted aryl, heteroaryl, substituted heteroaryl, heteroarylalkyl, substituted heteroarylalkyl, heterocycloalkyl, or substituted heterocycloalkyl, or taken together to form a heterocyclic ring of 3 to 8 atoms;

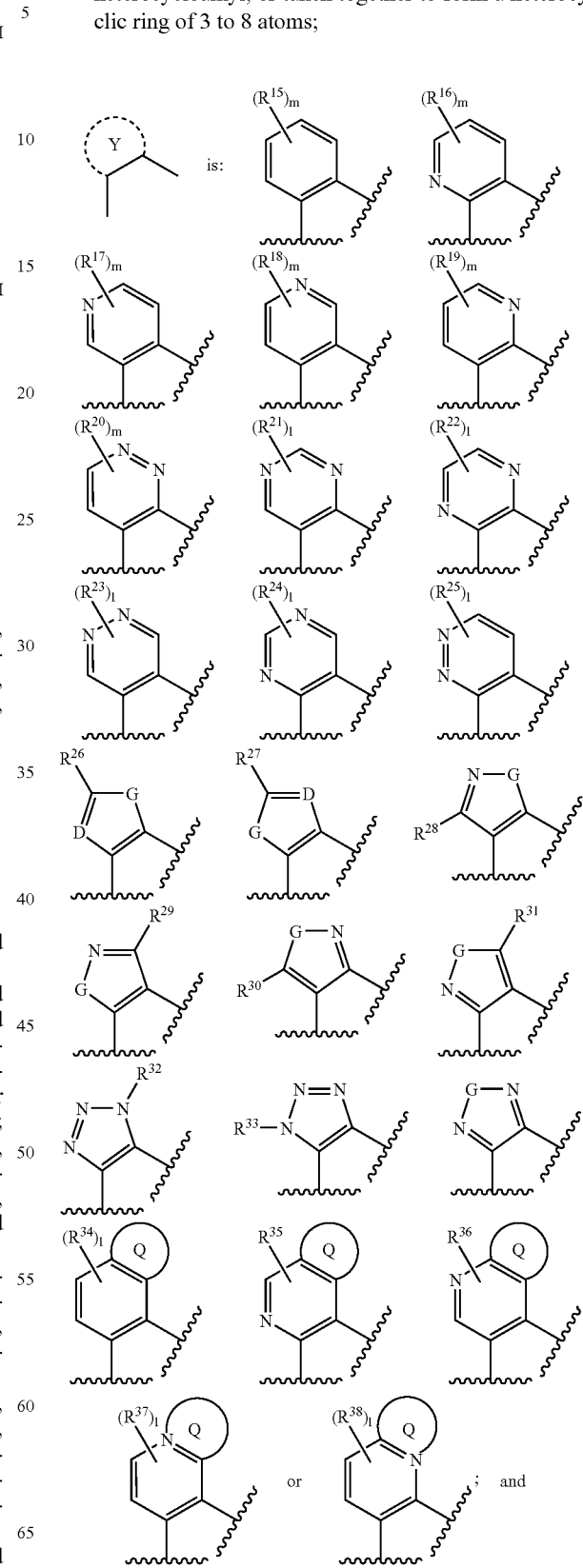

-continued

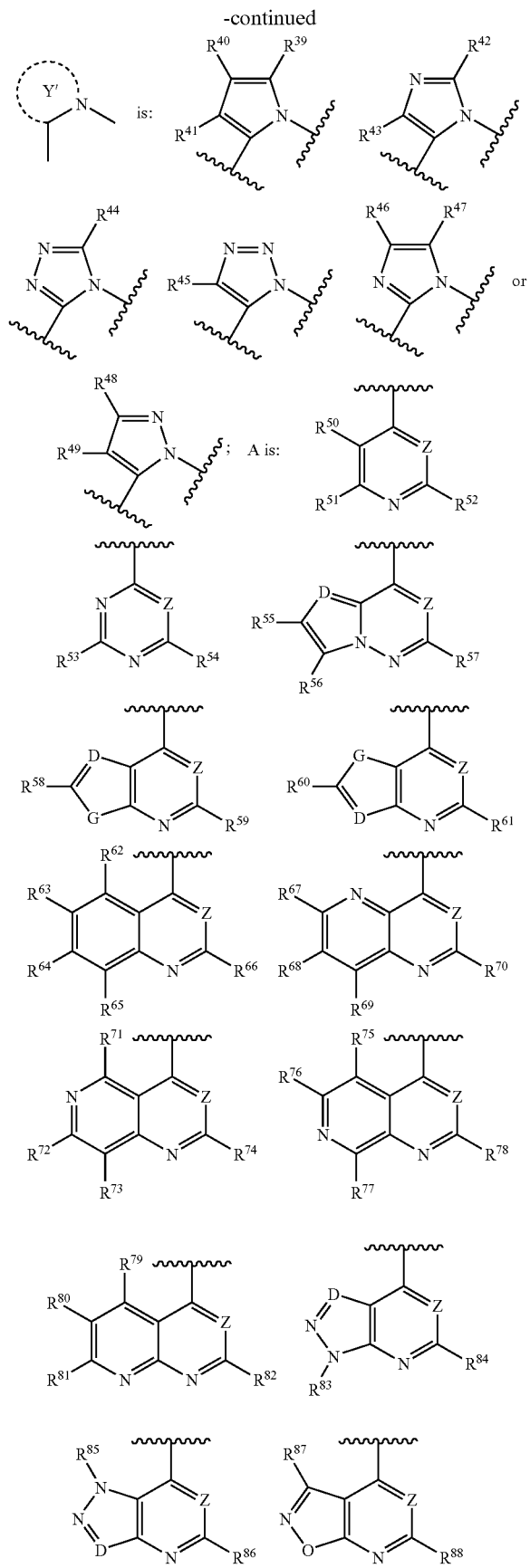

A is:

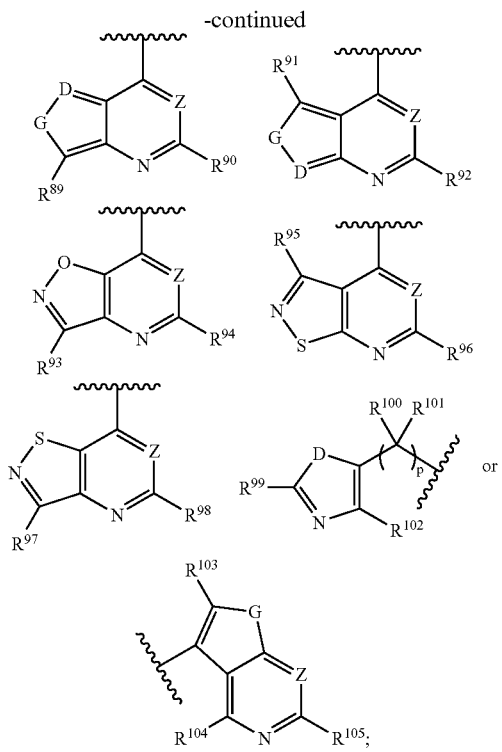

wherein
  G is O, S, or $NR^{106}$;
  D is $CR^{107}$ or N;
  Z is N or $CR^{108}$;
  Q is an optionally substituted carbocyclic or heterocyclic ring containing 4-8 atoms;
  $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$, $R^{80}$, $R^{81}$, $R^{82}$, $R^{84}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$, $R^{98}$, $R^{99}$, $R^{102}$, $R^{103}$, $R^{104}$, $R^{105}$, $R^{107}$ and $R^{108}$ are each independently H, halogen, haloalkyl, $NO_2$, cyano, $OR^{109}$, $NR^{110}R^{111}$, $CO_2R^{112}$, $C(O)NR^{113}R^{114}$, $SO_2R^{115}$, $SO_2NR^{116}R^{117}$, $NR^{118}SO_2R^{119}$, $NR^{120}C(O)R^{121}$, $NR^{122}CO_2R^{123}$, —$CO(CH_2)_mR^{124}$; —$CONH(CH_2)_mR^{125}$, $SR^{126}$, $SOR^{127}$, aminoalkyl, alkylaminoalkyl, alkylaminoalkylamino, diaalkylaminoalkylamino, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl; or
  $R^{40}$ is taken together with either $R^{39}$ or $R^{41}$ to form a carbocyclic, or an unsaturated or saturated heterocyclic ring of 3 to 8 atoms;
  $R^{32}$, $R^{33}$ $R^{83}$ and $R^{85}$ are each independently H, halogenated alkyl, —$CO_2R^{128}$, —$SO_2R^{129}$, —$CO(CH_2)_mR^{130}$, alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, hydroxyalkyl, aryl, substituted aryl, heteroaryl, substituted heteroaryl, arylalkyl, substituted arylalkyl, or heterocycloalkyl;

$R^{100}$ and $R^{101}$ are independently selected from H, halogen, alkyl, substituted alkyl, cycloalkyl, substituted cycloalkyl, aryl, substituted aryl, heteroaryl, substituted heteroaryl, heterocycloalkyl, or substituted heterocycloalkyl, or taken together to form a carbocyclic or heterocyclic ring of 3 to 8 atoms;

$R^{14}$, $R^{106}$, $R^{109}$, $R^{110}$, $R^{111}$, $R^{112}$, $R^{113}$, $R^{114}$, $R^{115}$, $R^{116}$, $R^{117}$, $R^{118}$, $R^{119}$, $R^{120}$, $R^{121}$, $R^{122}$, $R^{123}$, $R^{124}$, $R^{125}$, $R^{126}$, $R^{127}$, $R^{128}$, $R^{129}$ and $R^{130}$ are each independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

According to one embodiment of the present invention, methods for treating cancer are provided, especially for those cancers that are accompanied by and increased level of HGF or expression of Met in the patient, comprising administering to the patient in need of such treatment a therapeutically effective amount of a compound having Formula I or II as defined herein, in a pharmaceutically acceptable carrier.

The present invention is also directed to pharmaceutical compositions comprising a therapeutically effective amount of a compound having Formula I or II, as defined herein, and a pharmaceutically acceptable carrier.

DETAILED DESCRIPTION OF THE INVENTION

The present invention provides for compounds having Formulas I and II as defined above, pharmaceutical compositions employing such compounds, methods of making and methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. Preferred alkyl groups have from 1 to 6 carbon atoms. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Alkyl groups may be substituted with substituents selected from the following: alkyl, aryl, aryloxy, halo (such as F, Cl, Br, I), haloalkyl (such as $CCl_3$ or $CF_3$), alkoxy, alkylthio, hydroxy, —CN, nitro, carboxy (—COOH), alkyloxycarbonyl (—C(O)nR), alkylcarbonyloxy (—OCOR), amino (—NR'R"), carbamoyl (—NHCOOR— or —OCONHR—), urea (—NHCONHR—) or thiol (—SH).

The term "alkenyl" herein alone or as part of another group refers to a hydrocarbon radical straight, branched or cyclic, containing from 2 to 12 carbon atoms and at least one carbon to carbon double bond. Alkenyl groups may also be substituted at any available point of attachment. Exemplary substituents for alkenyl groups include those listed above for alkyl groups, and especially include $C_3$ to $C_7$ cycloalkyl groups such as cyclopropyl, cyclopentyl and cyclohexyl, which may be further substituted with, for example, amino, oxo, hydroxyl, etc.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkenyl groups include those listed above for alkyl groups such as amino, alkylamino, etc.

The numbers in the subscript after the symbol "C" define the number of carbon atoms a particular group can contain. For example "$C_1$ to $C_6$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_1$ to $C_6$ alkyl" can also refer to $C_1$ to $C_6$ alkylene which bridges two groups; examples include propane-1,3-diyl, butane-1,4-diyl, 2-methyl-butane-1,4-diyl, etc. "$C_2$ to $C_6$ alkenyl means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_2$ to $C_6$ alkenyl" can also refer to $C_2$ to $C_6$ alkenediyl which bridges two groups; examples include ethylene-1,2-diyl(vinylene), 2-methyl-2-butene-1,4-diyl, 2-hexene-1,6-diyl, etc. "$C_2$ to $C_6$ alkynyl" means a straight or branched carbon chain having at least one carbon-carbon triple bond, and from two to six carbon atoms; examples include ethynyl, propynyl, butynyl, and hexynyl.

The term "acyl" herein alone or as part of another group refers to an alkyl group bonded through a carbonyl group or —C(O)R.

The term "alkoxy" herein alone or as part of another group denotes an alkyl group, preferably having from 1 to 6 carbon atoms, bonded through an oxygen atom, such as —OR, wherein R is the alkyl group.

The term "alkyloxycarbonyl" herein alone or as part of another group refers to —C(O)OR, wherein R is an alkyl group.

The term "arylalkyl" or "aralkyl" herein alone or as part of another group denotes an aromatic ring bonded through an alkyl group (such as benzyl) as described above.

The term "haloalkyl" herein alone or as part of another group refers to a halogen atom bonded through an alkyl group, such as —$CF_3$.

The term "aminoalkyl" herein alone or as part of another group refers to an amino group (—NR'R") bonded through an alkyl.

The term "alkylaminoalkylamino" as used herein alone or as part of another group refers to a group such as —NR-alkyl-NR—$CH_3$.

The term "arylalkylamino" as used herein alone or as part of another group refers to an aryl group bonded through an alkyl group which is bonded through an amino group.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Preferred aryl groups contain from 6 to 14 carbon atoms in the rings. Aryl groups may optionally be substituted with one or more groups including, but not limited to halogen, such as Br, F, or Cl, alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=O, 1, 2), or thiol.

The term "amino" herein alone or as part of another group refers to $-NH_2$. An "amino" may optionally be substituted with one or two substituents (NR'R"), wherein R' and R" may be the same or different, such as alkyl, aryl, arylalkyl, alkenyl, alkynyl, heteroaryl, heteroarylalkyl, heterocycloalkyl, alkyl, heterocycloalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, or any of the alkyl or aryl substituents set out herein. In some embodiments, the amino groups are substituted with carboxyl or carbonyl to form N-acyl or N-carbamoyl derivatives.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, selected from the group consisting of halo, alkyl, substituted alkyl, wherein the substituents are defined as above for alkyl substituents, alkenyl, alkynyl, nitro, cyano, oxo (=O), hydroxy, alkoxy, thioalkyl, $-CO_2H$, $-C(=O)H$, $CO_2$-alkyl, $-C(=O)$alkyl, keto, =N—OH, =N—O-alkyl, aryl, heteroaryl, a five or six membered ketal (i.e. 1,3-dioxolane or 1,3-dioxane), —NR'R", $-C(=O)NR'R"$, $-CO_2NR'R"$, $-C(=O)NR'R"$, $-NR'CO_2R"$, $-NR'C(=O)R"$, $-SO_2NR'R"$, and $-NR'SO_2R"$, wherein each of R' and R" are independently selected from hydrogen, alkyl, substituted alkyl, and cycloalkyl, or R' and R" together form a heterocycloalkyl or heteroaryl ring.

The term "heteroaryl" or "heteroaromatic" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated or partially saturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, $-CO_2H$, $-C(=O)H$, $-CO_2$-alkyl, $-C(=O)$alkyl, phenyl, benzyl, phenylethyl, phenyloxy, phenylthio, cycloalkyl, substituted cycloalkyl, heterocycloalkyl, heteroaryl, —NR'R", $-C(=O)NR'R"$, $-CO_2NR'R"$, $-C(=O)NR'R"$, $-NR'CO_2R"$, $-NR'C(=O)R"$, $-SO_2NR'R"$, and $-NR'SO_2R"$, wherein each of R' and R" is independently selected from hydrogen, alkyl, substituted alkyl, and cycloalkyl, or R' and R" together form a heterocycloalkyl or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which one of the carbon atoms in the ring is replaced by a heteroatom selected from O, S or N, and in which up to three additional carbon atoms may be replaced by said heteroatoms. The term "heterocycloalkyl" herein alone or as part of another group refers to a stable, saturated, or partially unsaturated monocyclic ring system containing 5 to 7 ring members of carbon atoms and other atoms selected from nitrogen, sulfur and/or oxygen. A heterocyclic ring may be a 5, 6 or 7-membered monocyclic ring and contain one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocycloalkyl groups include piperazine, piperidine, morpholine, homomorpholine, thiomorpholine, pyrrolidine, and azetidine.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

The phrase "gene amplification," as used herein means the selective synthesis of a DNA fragment that results in multiple copies of the Met gene or fragment of the chromosome in which Met is encoded.

The phrase "activated Met mutation" as used herein means a selective change in the DNA sequence of Met resulting in a Met protein that is constitutively (i.e., permanently) phosphorylated.

The phrase "HGF stimulation," as used herein means the ability of a HGF to bind its cognate receptor (Met) in such a way as to activate the receptor that results in a phenotypic response. In the case of Met, this can be cellular proliferation, motility, differentiation and/or survival.

The term "anticancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin,) and small molecules such as ZD6474, AZD-2171, and SU6668; Vatalanib, BAY-43-9006, SU11248, CP-547632, and CEP-7055; Her 1 and Her 2 inhibitors including anti-Her2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, BMS-354825, AZD-0530 and SKI-606, and AP-23464; Casodex®, Bcr-Abl inhibitors (GLEEVAC), (bicalutamide, Astra Zeneca), Tamoxifen; MEK-1 kinase inhibitors, MAPK kinase inhibitors, PI3 kinase inhibitors; Met inhibitors, aurora kinase inhibitors, PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; IGF1R inhibitors such as those disclosed in US2004/44203A1, inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, ixabepilone, [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "patient" encompasses all mammalian species, including humans, cows, horses, dogs, and cats.

The phrase "therapeutically effective" is intended to qualify the amount of each agent, which will achieve the goal of improvement in disorder severity and the frequency of incidence over treatment of each agent by itself, while avoiding adverse side-effects typically associated with alternative therapies. For example, effective anticancer agents prolong the survivability of the patient, inhibit the rapidly proliferating cell growth associated with the neoplasm, or effect a regression of the neoplasm.

The phrase "pharmaceutically acceptable salt(s)", or "salt" as used herein, unless otherwise indicated, includes salts of acidic or basic groups which may be present in the compounds of formulas I and II. The compounds of formulas I and II that are basic in nature are capable of forming a wide variety of salts with various inorganic and organic acids. Accordingly, compounds having Formula I and II include both the free base and salt forms. The acids that may be used to prepare pharmaceutically acceptable acid addition salts of such basic compounds of formulas I and II are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, mesylate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Compounds of the present invention may contain one or more additional asymmetric carbon atoms and therefore exist in two or more stereoisomeric forms. The present invention includes the individual stereoisomers of the compounds of the formula I and II, where appropriate, the individual tautomeric forms thereof, together with mixtures thereof.

Separation of diastereoisomers may be achieved by conventional techniques, e.g. by fractional crystallization, chromatography or H.P.L.C. of a stereoisomeric mixture of a compound of the formula I and/or II, or a suitable salt or derivative thereof. An individual enantiomer of a compound of the formula I or II may also be prepared from a corresponding optically pure intermediate or by resolution, such as by H.P.L.C. of the corresponding racemate using a suitable chiral support or by fractional crystallization of the diastereoisomeric salts formed by reaction of the corresponding racemate with a suitable optically active acid or base, as appropriate.

The present invention is directed to compounds having the following Formulae I or II, including salts thereof:

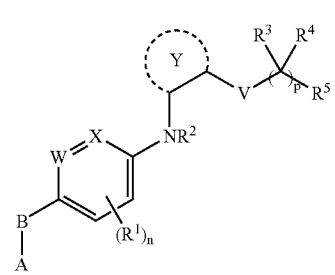

-continued

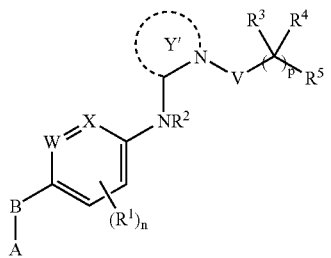
II wherein
- each $R^1$ is H, halogen, halogenated alkyl, cyano, $NO_2$, $OR^6$, $NR^7R^8$, alkyl, substituted alkyl, cycloalkyl, substituted cycloalkyl, aryl, substituted aryl, heteroaryl, substituted heteroaryl, aryalkyl, substituted arylalkyl, heterocycloalkyl, or substituted heterocycloalkyl;
- B is O, $NR^9$, S, SO, $SO_2$, or $CR^{10}R^{11}$ and preferably O;
- W and X are each independently C or N;
- V is CO;
- n is 1 to 4;
- m is 1 to 4;
- p is 0 to 2;
- l is 1 to 2;
- $R^2$ is H, alkyl, substituted alkyl, cycloalkyl, or substituted cycloalkyl;
- $R^3$ and $R^4$ are independently H, halogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycloalkyl, substituted heterocycloalkyl or taken together to form a carbocyclic or heterocyclic ring of 3 to 8 atoms;
- $R^5$ is $—NR^{12}R^{13}$, $—OR^{14}$, alkyl, substituted alkyl, haloalkyl, cycloalkyl, substituted cycloalkyl, aryl, substituted aryl, heteroaryl, substituted heteroaryl, aryalkyl, substituted arylalkyl, heterocycloalkyl, or substituted heterocycloalkyl;
- $R^6$, $R^7$, $R^8$, and $R^9$ are each independently H, alkyl, substituted alkyl, alkenyl, substituted alkenyl, alkynyl, substituted alkynyl, cycloalkyl, substituted cycloalkyl, heterocycloalkyl, substituted heterocycloalkyl, aryl, substituted aryl, heteroaryl, substituted heteroaryl;
- $R^{10}$ and $R^{11}$ are each independently H, halogen, alkyl, substituted alkyl, cycloalkyl, substituted cycloalkyl, aryl, substituted aryl, benzyl, heteroaryl, substituted heteroaryl, heterocycloalkyl, or substituted heterocycloalkyl, or taken together to form a carbocyclic or heterocyclic ring of 3 to 8 atoms;
- $R^{12}$ and $R^{13}$ are each independently H, alkyl, substituted alkyl, cycloalkyl, substituted cycloalkyl, arylalkyl, substituted arylalkyl, aryl, substituted aryl, heteroaryl, substituted heteroaryl, heteroarylalkyl, substituted heteroarylalkyl, heterocycloalkyl, or substituted heterocycloalkyl, or taken together to form a heterocyclic ring of 3 to 8 atoms;

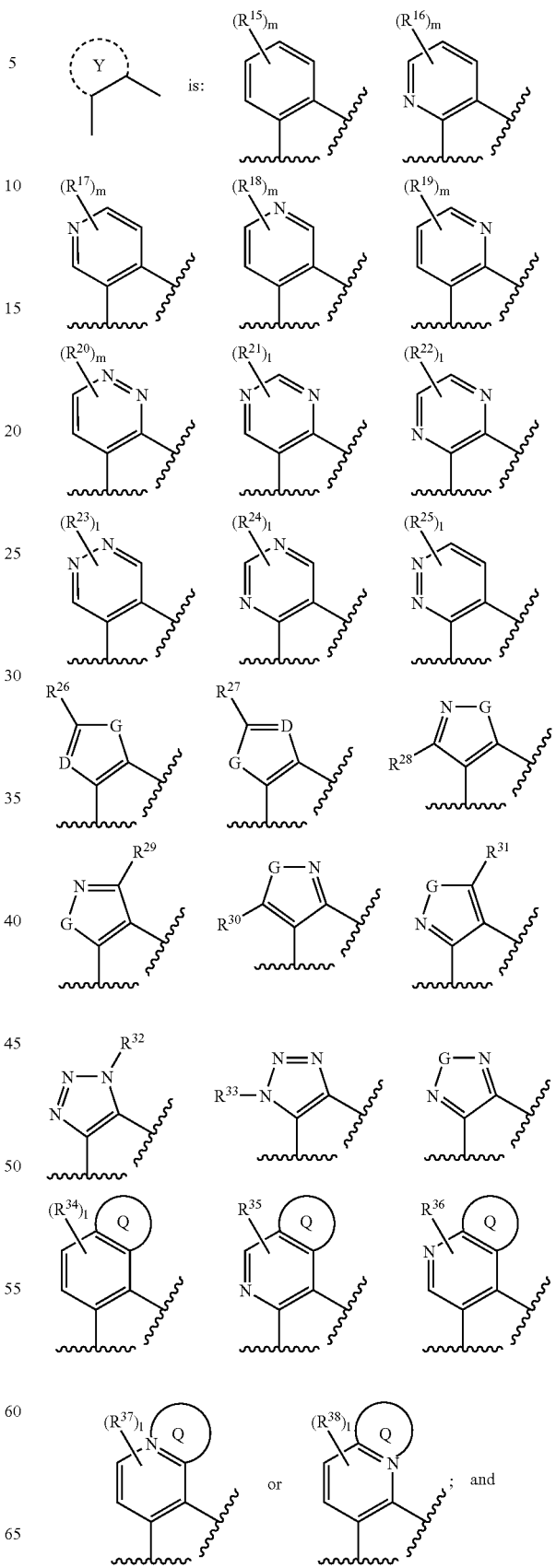

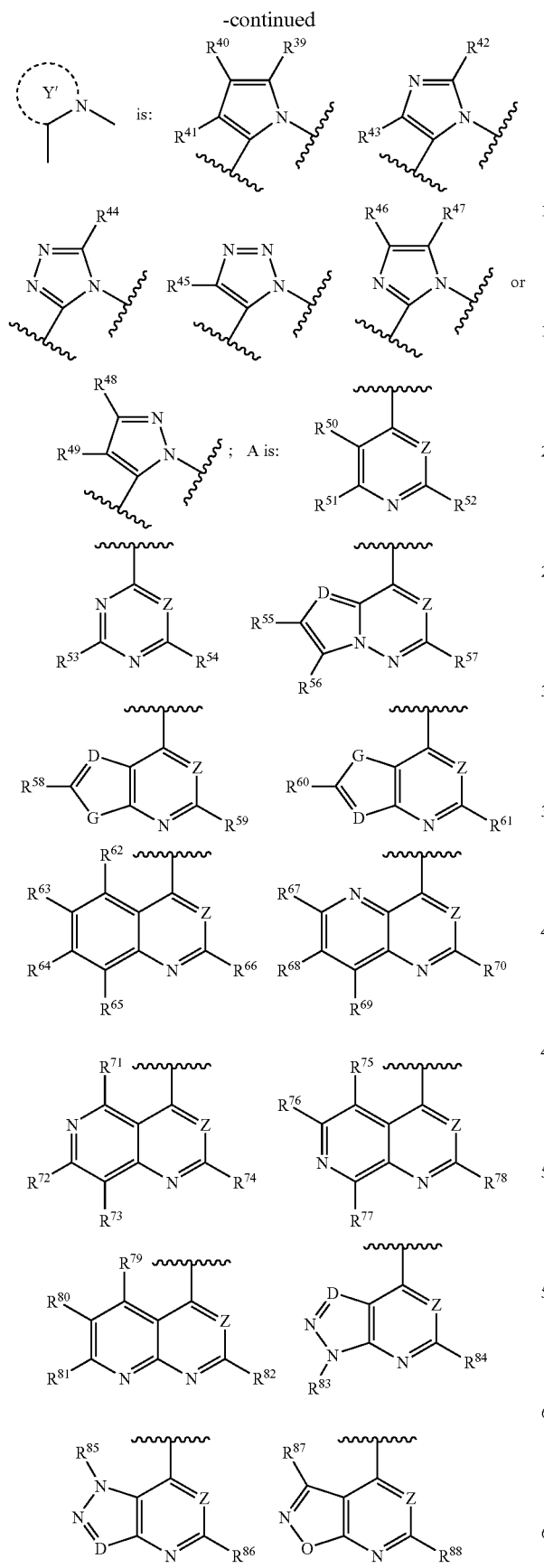
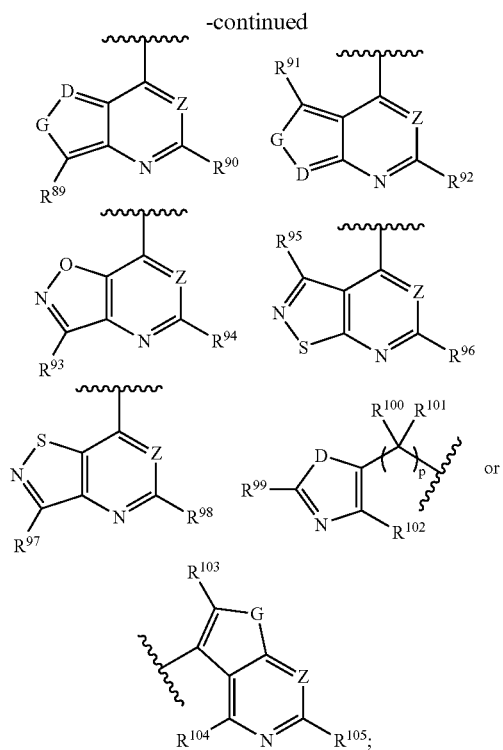

wherein
G is O, S, or NR$^{106}$;
D is CR$^{107}$ or N;
Z is N or CR$^{108}$;
Q is an optionally substituted carbocyclic or heterocyclic ring containing 4-8 atoms;
R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$, R$^{48}$, R$^{49}$, R$^{50}$, R$^{51}$, R$^{52}$, R$^{53}$, R$^{54}$, R$^{55}$, R$^{56}$, R$^{57}$, R$^{58}$, R$^{59}$, R$^{60}$, R$^{61}$, R$^{62}$, R$^{63}$, R$^{64}$, R$^{65}$, R$^{66}$, R$^{67}$, R$^{68}$, R$^{69}$, R$^{70}$, R$^{71}$, R$^{72}$, R$^{73}$, R$^{74}$, R$^{75}$, R$^{76}$, R$^{77}$, R$^{78}$, R$^{79}$, R$^{80}$, R$^{81}$, R$^{82}$, R$^{84}$, R$^{86}$, R$^{87}$, R$^{88}$, R$^{89}$, R$^{90}$, R$^{91}$, R$^{92}$, R$^{93}$, R$^{94}$, R$^{95}$, R$^{96}$, R$^{97}$, R$^{98}$, R$^{99}$, R$^{102}$, R$^{103}$, R$^{104}$, R$^{105}$, R$^{107}$ and R$^{108}$ are each independently H, halogen, haloalkyl, NO$_2$, cyano, OR$^{109}$, NR$^{110}$R$^{111}$, CO$_2$R$^{112}$, C(O)NR$^{113}$R$^{114}$, SO$_2$R$^{115}$, SO$_2$NR$^{116}$R$^{117}$, NR$^{118}$SO$_2$R$^{119}$, NR$^{120}$C(O)R$^{121}$, NR$^{122}$CO$_2$R$^{123}$, —CO(CH$_2$)$_m$R$^{124}$; —CONH(CH$_2$)$_m$R$^{125}$, SR$^{126}$, SOR$^{127}$, aminoalkyl, alkylaminoalkyl, alkylaminoalkylamino, diaalkylaminoalkylamino, alkylaminoalkynyl, C$_1$ to C$_6$ alkyl, substituted C$_1$ to C$_6$ alkyl, C$_3$ to C$_7$ cycloalkyl, substituted C$_3$ to C$_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl; or R$^{40}$ is taken together with either R$^{39}$ or R$^{41}$ to form a carbocyclic, or an unsaturated or saturated heterocyclic ring of 3 to 8 atoms;

R$^{32}$, R$^{33}$ R$^{83}$ and R$^{85}$ are each independently H, halogenated alkyl, —CO$_2$R$^{128}$, —SO$_2$R$^{129}$, —CO(CH$_2$)$_m$ R$^{130}$, alkylaminoalkyl, alkylaminoalkynyl, C$_1$ to C$_6$ alkyl, substituted C$_1$ to C$_6$ alkyl, C$_3$ to C$_7$ cycloalkyl, substituted C$_3$ to C$_7$ cycloalkyl, hydroxyalkyl, aryl, substituted aryl, heteroaryl, substituted heteroaryl, arylalkyl, substituted arylalkyl, or heterocycloalkyl;

$R^{100}$ and $R^{101}$ are independently selected from H, halogen, alkyl, substituted alkyl, cycloalkyl, substituted cycloalkyl, aryl, substituted aryl, heteroaryl, substituted heteroaryl, heterocycloalkyl, or substituted heterocycloalkyl, or taken together to form a carbocyclic or heterocyclic ring of 3 to 8 atoms;

$R^{14}$, $R^{106}$, $R^{109}$, $R^{110}$, $R^{111}$, $R^{112}$, $R^{113}$, $R^{114}$, $R^{115}$, $R^{116}$, $R^{117}$, $R^{118}$, $R^{119}$, $R^{120}$, $R^{121}$, $R^{122}$, $R^{123}$, $R^{124}$, $R^{125}$, $R^{126}$, $R^{127}$, $R^{128}$, $R^{129}$ and $R^{130}$ are each independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

According to one embodiment of the present invention, A is

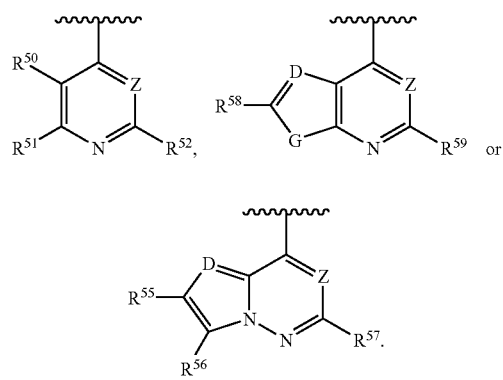

According to a preferred embodiment, D is —CH, G is —NH, Z is N or —CH and $R^{50}$, $R^{51}$, $R^{52}$, $R^{58}$ and $R^{59}$ are each, independently, H, amino, or substituted lower alkyl.

According to one embodiment of the present invention,

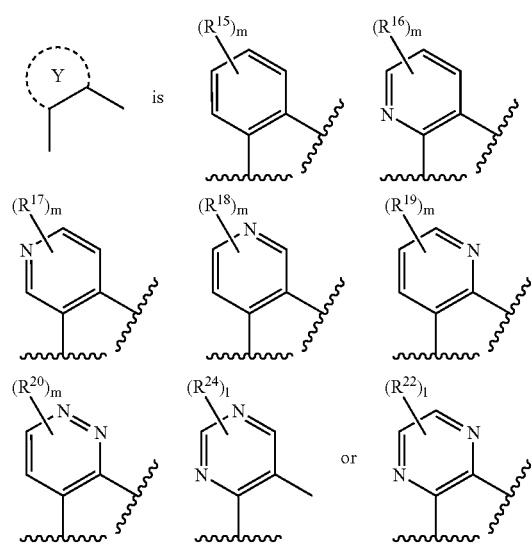

and is prefereably

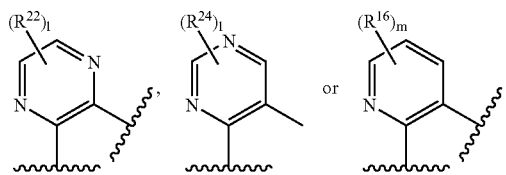

wherein each $R^{22}$, $R^{24}$ and $R^{16}$ are as defined above and preferably, H, hydroxyl, alkoxy, such as methoxy, halo, preferably Cl or Br, lower alkyl, preferably methyl, ethyl or propyl, (—$SCH_3$), haloalkyl, preferably —$CF_3$, —$NR^{10}R^{11}$, —$SR^{126}$, —CN, amino, aminoalkyl, alkylamino, dialkylaminoalkylamino, arylalkylamino or heterocycloalkyl. In a preferred embodiment, each $R^{22}$, $R^{24}$, and $R^{16}$ is, independently, H, —OH, —$OCH_3$, Br, Cl, —$CH_3$, —$SCH_3$, —$CF_3$, —CN, —$CH_2NH_2$, morpholinyl, piperazinyl, —$NR^{10}R^{11}$, wherein $R^{10}$ and $R^{11}$ are, independently, H, lower alkyl, benzyl, or dialkylaminoalkyl.

According to one embodiment of the present invention, W and X are C and each $R^1$ is independently H or F. It should be noted that in the case where W and X are carbon, —CH is indicated unless one of the valences is occupied by an $R_1$ group other than H.

According to one embodiment of the present invention, compounds have the Formulae I or II wherein $R^5$ is an optionally substituted phenyl, and preferably substituted with halo, lower alkyl, hydroxyalkyl, heterocycloalkyl, amino or alkylamino.

According to one embodiment of the present invention, a method is provided for treating a proliferative disease, such as cancer, via modulation of Met kinase by administering to a patient in need of such treatment a therapeutically effective amount of a compound having formula I or II, as defined above, in combination (simultaneously or sequentially) with at least one other anti-cancer agent. In a preferred embodiment, the proliferative disease is cancer.

Specifically, the compounds of Formulas I and II are useful in the treatment of a variety of cancers, most specifically, those cancers that are dependent upon Met activation. Met activation may be regulated by gene amplification, mutation(s) and/or HGF stimulation in which HGF is provided by either the tumor (autocrine) or host (paracrine) tissues. Thus, the present invention is also directed to methods of treating cancers such as the following bladder breast, colorectal, gastric, head and neck, kidney, liver, lung, ovarian, pancreas/gall bladder, prostate, thyroid, osteosarcoma, rhabdomyosarcoma, MFH/fibrosarcoma, glioblastomas/astrocytomas, melanoma, and mesothelioma.

Generally, compounds of the present invention may be useful for treating, the following:
a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;
b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;
c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;
e) tumors of the central and peripheral nervous system, including astrocytoma, neuroblastoma, glioma and schwannomas; and
f) other tumors, including melanoma, seminoma, teratocarcinoma, osteosarcoma, xenoderoma pigmentosum, keratoctanthoma, thyroid follicular cancer and Kaposi's sarcoma.

Due to the key role protein kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulo-nephritis, restenosis following angioplasty or vascular surgery, hypertrophic scar formation, inflammatory bowel disease, transplantation rejection, endotoxic shock, and fungal infections.

Compounds of Formulas I and II as modulators of apoptosis, will be useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formulas I and II may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formulas I and II may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formulas I and II may also be useful in inhibiting tumor angiogenesis and metastasis.

The compounds of this invention may also be useful in combination (administered together or sequentially) with known anti-cancer agents or treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2).

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients or carriers which are suitable for the manufacture of tablets. These excipients or carriers may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formulas I and II may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of Formulas I and II may also be administered sequentially with known anticancer or cytotoxic agents when a combination formulation is inappropriate. The invention is not limited in the sequence of administration; compounds of Formulas I and II may be administered either prior to or after administration of the known anticancer or cytotoxic agent(s).

Certain compounds of Formulas I and II may generally be prepared according to the following Schemes 1-12. Tautomers and solvates (e.g., hydrates) of the compounds of Formulas I and II are also within the scope of the present invention. Methods of solvation are generally known in the art. Accordingly, the compounds of the instant invention may be in the free or hydrate form, and may be obtained by methods exemplified by the following schemes.

In general, compounds of Formula I may be prepared using the chemistry described in Scheme 1, where B is O, NH, or S and LV is a leaving group (e.g., halogen, triflate, or other sulfonate). Compounds A-LV (1) can be purchased or readily prepared using synthetic methods known to one skilled in the art. For example, compounds A-LV (1) can be prepared according to the general procedures outlined in Hunt, J. T. et al. WO 00/071129; Hunt, J. T. et al. *J. Med. Chem.* 2004, 47, 4054-4059; Leftheris, K. et al. WO 02/040486; Mastalerz, H. et al. WO 03/042172; Dyckman, A. et al. WO 03/091229; Vite, G. D. et al. WO 04/054514; Salvati, M. E. et al. WO 03/082208; Thibault, C. et al. *Org. Lett.* 2003, 5, 5023-5025; Hennequin, L. F. et al. *J. Med. Chem.* 1999, 42, 4369-5389; Hagmann, W. K. et al. *Bioorg. Med. Chem. Lett.* 2000, 10, 1975-1978; Spitzner, D. *Science of Synthesis* 2005, 15, 11-284; Bhagwat, S. S. et al. WO 01/057040; Soloducho, J. et al. *Arch. de Pharmazie* 1990, 323, 513-515; Phuan, P.-W. and Kozlowski, M. C. *Science of Synthesis* 2005, 15, 947-985; Nishikawa, S. Et al. *J. Ag. and Food Chem.* 1995, 43, 1034-

1038; Johns, A. et al. WO 99/58533; Rewcastle, G. W. et al. *J. Med. Chem.* 1996, 39, 1823-1835; Zhang, Z. et al. *J. Org. Chem.* 2002, 67, 2345-2347; Itoh, T. et al. *J. Heterocyclic Chem.* 1982, 19, 513-517; Tedder, M. E. et al. *Bioorg. Med. Chem. Lett.* 2004, 14, 3165-3168; Dorn, H. et al. *J. Prakt. Chem.* 1982, 324, 557; Sanghvi, Y. S. et al. *J. Med. Chem.* 1989, 32, 945-951; Temple, C. Jr. et al. *J. Org. Chem.* 1972, 37, 3601-3604; Hurst, J. et al. EP119774; Hurst, J. et al. EP151962; Ward, R. W. et al. EP152910; Luzzio, M. J. et al. WO 01/094353; Marx, M. A. et al. WO 03/000194; Boschelli, D. H. et al. WO 04/048386; He, M. et al. WO 05/021554; Barker, J. M. et al. *J. Chem. Res., Synopses* 1986, 4, 122-123, the disclosures of which are herein incorporated by reference. Also, A-LV groups can be prepared according the procedures generally described in U.S. patent application Ser. No. 11/167,049 filed Jun. 24, 2005; Ser. No. 11/111,144 filed Apr. 21, 2005; Ser. No. 11/113,838, filed Apr. 24, 2005; and 11,167,043, filed Jun. 24, 2005.

Treatment of compound 1 with an appropriately functionalized compound 2 (a substituted phenol, aniline, or thiophenol) in the presence of a base, such as potassium tert-butoxide, followed by reduction of the nitro intermediate with for example, zinc powder and ammonium chloride can provide compound 3 (Scheme 1). Alternatively, intermediate 3 can be obtained from the combination of compounds 4 and 5 in the presence of a base (e.g., cesium carbonate, potassium carbonate, potassium tert-butoxide) followed by subsequent reduction. The coupling of compounds 3 and 6 can be accomplished under acidic conditions when the Y ring of 6 contains at least one heteroatom (Galeeva, R. N. et al. *Khim. Farm. Zh.* 1998, 32, 31; Kermack, W. O. et. al. *J. Chem. Soc.* 1942, 726; i.e., ring Y is a pyridine ring) to generate compounds of Formula I. Alternatively, compounds of Formula I can be obtained by the coupling of compounds 3 and 6 promoted with a metal, such as palladium or copper (Wolfe, J. P. et. al. *Tetrahedron Lett.* 1997, 38, 6359 and Lowe, J. A. et. al. *J. Med. Chem.* 1991, 34, 624).

According to Scheme 2, the amide or ester derivatives 6 (where LV is a leaving group, such as a halogen, a triflate, or other sulfonate; and p, Y, $R^3$-$R^5$, $R^{12}$ and $R^{13}$ are as defined above) can be obtained from the carboxylic acids III. The ketone derivatives 6 can be prepared from the corresponding Weinreb amides IV using the appropriate organometallic reagent (M=metal), such as an organolithium or Grignard reagent. Compound III can be prepared using methods known to one of skill in the art, or alternatively, may be commercially available, such as, for example, when

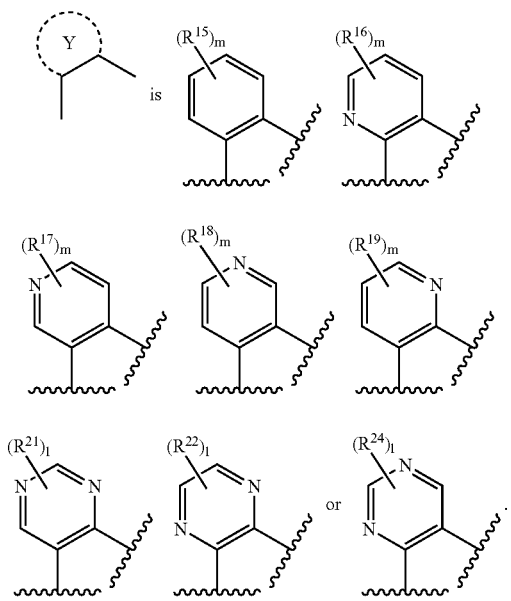

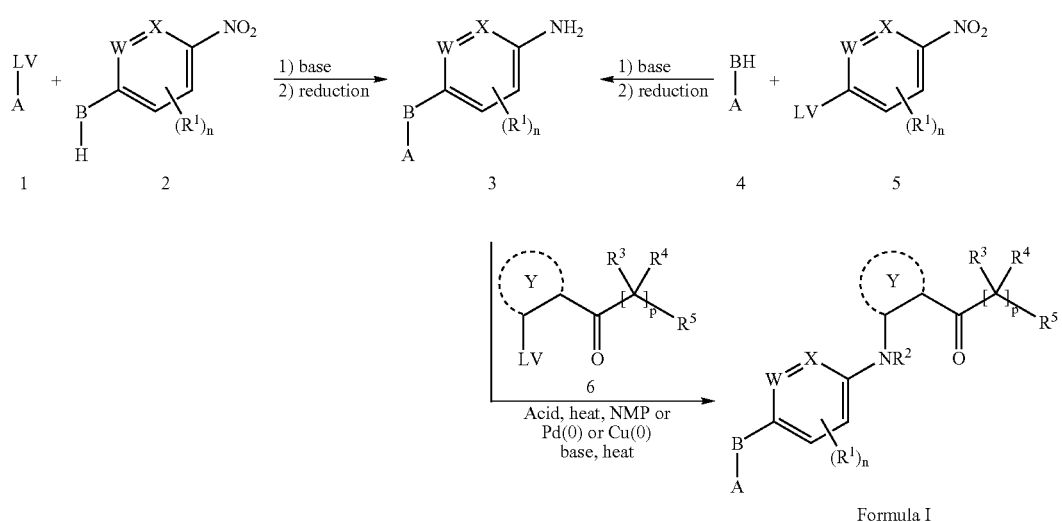

LV = leaving group
B = O, NH, S
A, W, X, Y, n, p and $R^1$-$R^5$
are as defined above The following starting materials III are also commercially available:

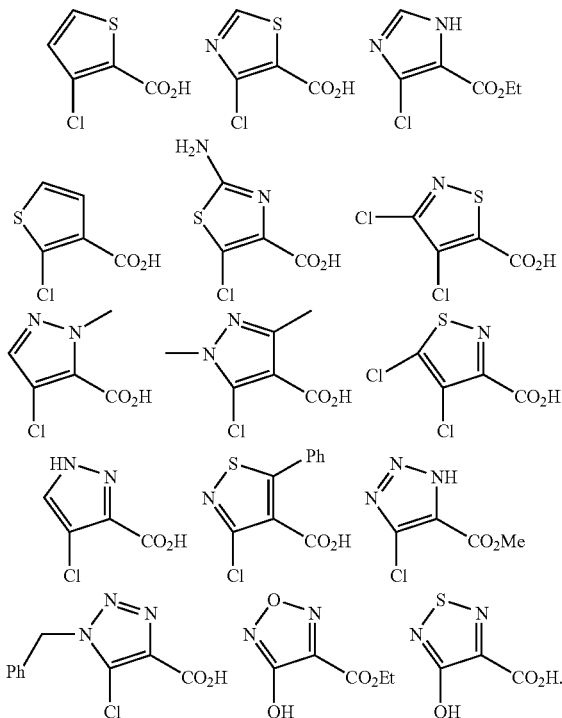

Additional starting material carboxylic acids III (or ester intermediates) such as those listed below can be prepared according to the following referenced literature, the disclosures of which are all herein incorporated by reference in their entirety.

The starting material III having the structure

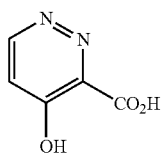

can be prepared according to the procedures described in Ichimoto, I. et al., *Agricultural & Biol. Chem.* 1967, 31, 979-989.

Esters having the formulas

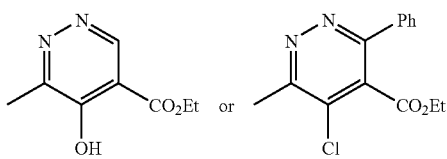

can be made according to the general procedures outlined in Battesti, P. et al., *Bull. Soc. Chim. Fr.* 1975, 2185-2188 and Gelin, S. *J. Org. Chem.* 1979, 44, 3053-3057.

Starting materials III having the structures

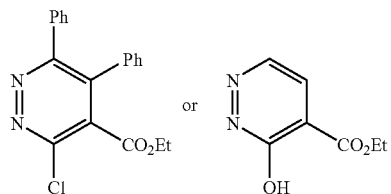

can be prepared according to the general procedure outlined in Radwan, S. M. et al., *Pharmazie* 1997, 52, 483-485 and Yanai, M. et. al. *Chem. Pharm. Bull.* 1977, 25, 1856-1861.

Starting material III having the structure

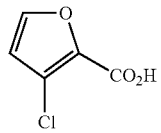

can be prepared according to the procedures outlined in Zhang, H. et al., *J. Med. Chem.* 2005, 48, 5215-5223.

Starting material III having the structure

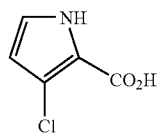

can be prepared according to the procedures outlined in Tehrani, K. A. et al., *Tetrahedron* 1999, 55, 4133-4152.

Starting material III having the structure

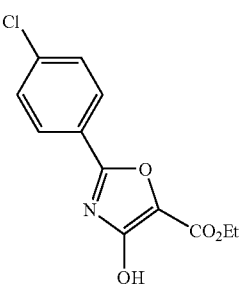

can be prepared by following the general procedure outlines in Tsuge, O. et al., *Tetrahedron* 1973, 29, 1983-1990.

Starting material III having the structure

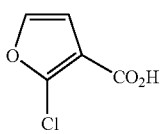

can be prepared according the procedures outlines in Roques, B. et al., *Bull. Soc. Chim. Fr.* 1971, 242-245.

Starting material III having the structure

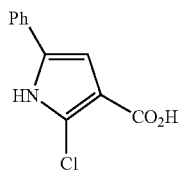

can be prepared according to the general procedures outlined in Pinna, G. A. et al., *Farmaco* 1999, 54, 542-550.

Starting material III having the structure

can be prepared according the general procedures outlined in Grifantini, M. et al., *Annal. di Chim. (Rome, Italy)* 1965, 55, 576-582.

Starting material III having the structure

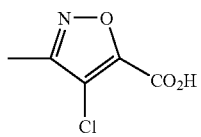

can be prepared following the procedures outlined in Nesi, R. et al., *J. Chem. Soc. Perkin Trans* 1 1985, 1871-1874.

Starting material III having the structure

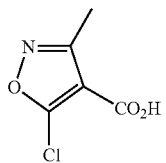

can be prepared by following the general procedures outlined in Adembri, G. et al., *Bollettino Scientifico della Facolta di Chimica Industriale di Bologna* 1965, 23, 203-222.

Starting material III having the structure

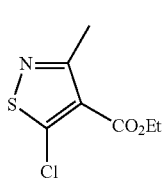

can be prepared by following the general procedures outlined in Howe, R. K., *J. Org. Chem.* 1977, 42, 3230-3233.

Starting material III having the structure

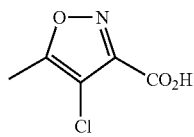

can be prepared according to the general procedures outlined in Wakefield, B. J., *Science of Synthesis* 2002, 11, 229-288.

Starting material III having the structure

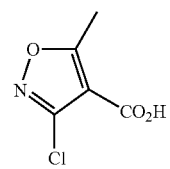

can be prepared by following the general procedures outlined Bowden, K., *J. Chem. Soc. Section C.* 1968, 172-85.

Starting material III having the structure

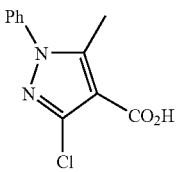

can be prepared according to Rojahn, C. A. et. al. *Ann.* 1923, 434, 252-264.

Starting material III having the structure

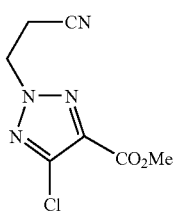

can be prepared generally according to the procedure outlined in Sedov, A. L. et al., *Khimiya Geterotsiklicheskikh Soedinenii* 1994, 1369-1374.

Starting material III having the structure

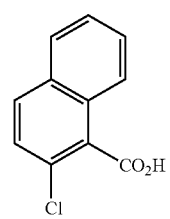

can be prepared generally according to the general procedure outlined in Tilly, D. et. al. *Chem. Lett.* 2005, 34, 446-447.

Starting material III having the structure

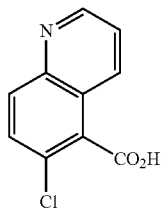

can be prepared generally according to the procedure outlined in Evans, R. et al., WO 04/106305.

Starting material III having the structure

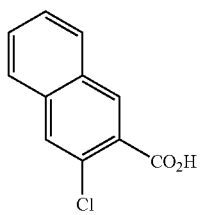

can be prepared generally according the procedure outlined in Cairns, B. et al., *J. Chem. Soc.* 1950, 1322-1327.

Starting material III having the structure

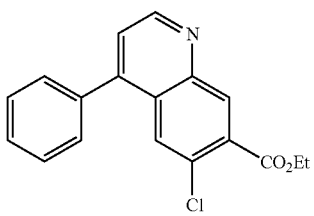

can be prepared generally according to the procedure outlined in Bartmann, W., *Heterocycles* 1989, 29, 707-718.

Starting material III having the structure

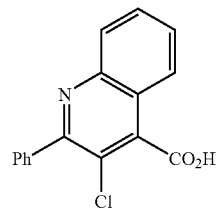

can be prepared generally according to the procedures outlined in Raveglia, L. F. et al., *J. Heterocyclic Chem.* 1997, 34, 557-559.

Starting material III having the structure

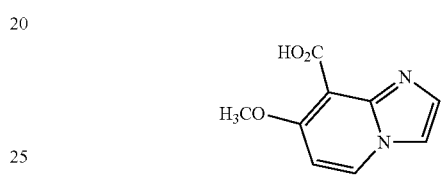

can be prepared generally according to the procedures outlined by Barber, C. G. et al., US 05/020611.

Starting material III having the structure

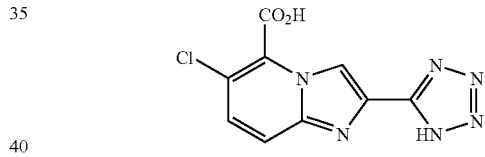

can be prepared generally according to the procedures outlined in Hansen, D. W., Jr. et al., WO 91/08211 (U.S. Pat. No. 5,360,796), the disclosures of which are herein incorporated by reference.

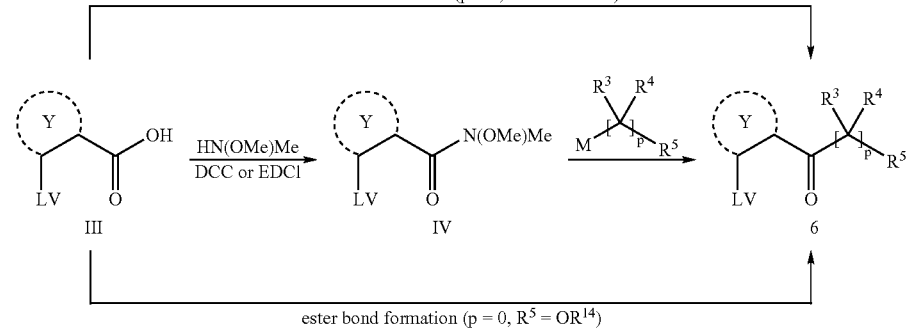

When B=CR[10]R[11] in Formula I, the synthesis of these compounds can be accomplished using the chemistry illustrated in Scheme 3. Thus, compound 1 can be converted to the corresponding organometallic reagent 7 via Grignard formation or lithium-halogen exchange. Treatment of compound 7 with an appropriately functionalized aldehyde 8, followed by deoxygenation of the intermediate with, for example triethylsilane, trifluoroacetic acid and subsequent reduction of the nitro group (e.g., zinc and ammonium chloride) can furnish intermediate 9. The coupling of intermediate 9 with compound 6, using conditions previously described in Scheme 1 can provide the desired analogues of Formula I.

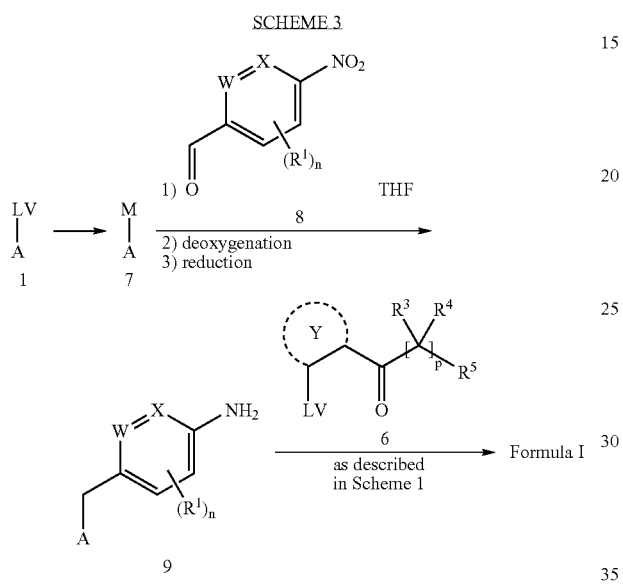

LV = leaving group
M = metal, such as Mg or Li
A, W, X, Y, n, p, R[1], R[3]-R[5] are as defined above Scheme 4 illustrates the preparation of a specific example of Formula I. Thus, 4-chloropicolinamide (10), derived from commercially available 4-chloropicolinic acid (TCI America) can be treated with 3-fluoro-4-hydroxyaniline (11, Aldrich) under basic conditions to provide adduct 12. Intermediate 12 can then be treated with commercially available N-(4-chlorophenyl)-2-chloronicotinamide (13, Maybridge) under acidic conditions in a microwave to provide intermediate 14 (Galeeva, R. N. et al. *Khim. Farm. Zh.* 1998, 32, 31; Kermack, W. O. et. al. *J. Chem. Soc.* 1942, 726 herein incorporated by reference). Treatment of 14 with bis(trifluoroacetoxy)iodobenzene (Yu, C. et. al. *Tetrahedron Lett.* 2001, 42, 1449 herein incorporated by reference) and pyridine can provide compound 15.

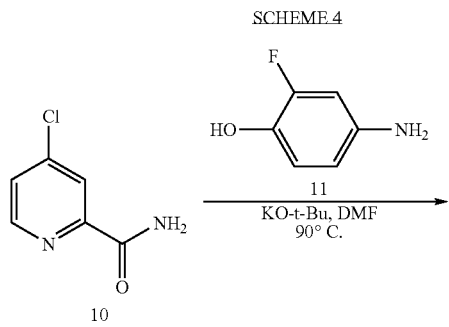

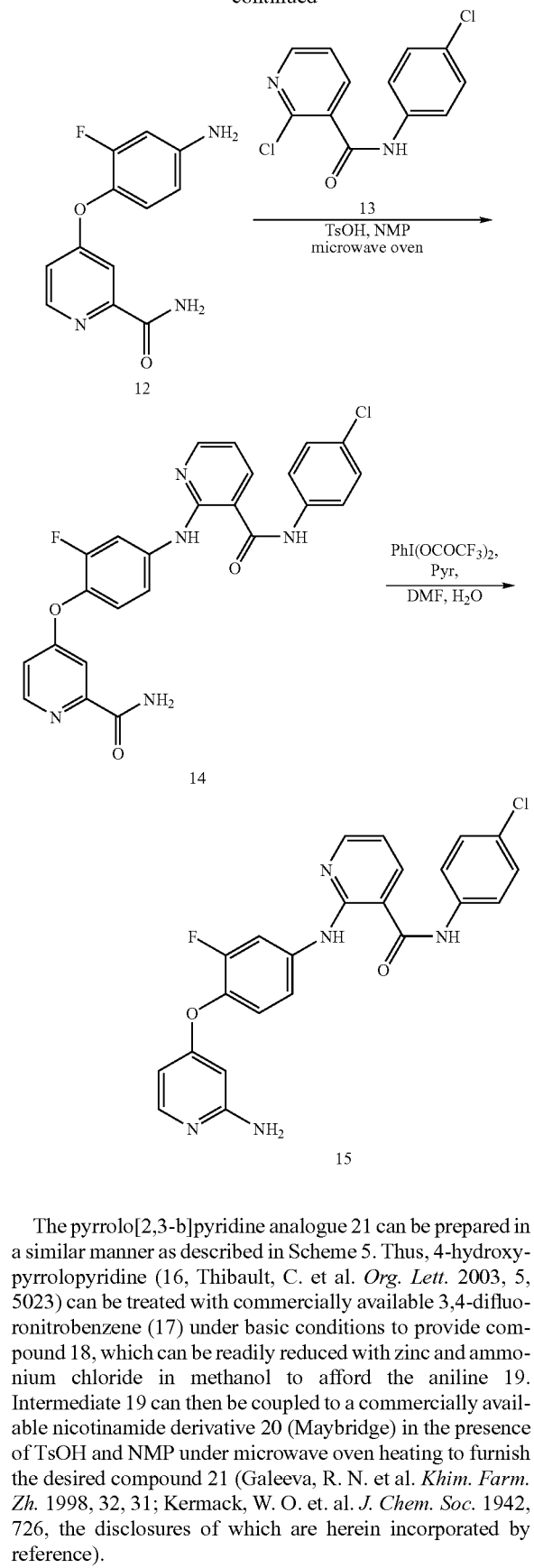

The pyrrolo[2,3-b]pyridine analogue 21 can be prepared in a similar manner as described in Scheme 5. Thus, 4-hydroxypyrrolopyridine (16, Thibault, C. et al. *Org. Lett.* 2003, 5, 5023) can be treated with commercially available 3,4-difluoronitrobenzene (17) under basic conditions to provide compound 18, which can be readily reduced with zinc and ammonium chloride in methanol to afford the aniline 19. Intermediate 19 can then be coupled to a commercially available nicotinamide derivative 20 (Maybridge) in the presence of TsOH and NMP under microwave oven heating to furnish the desired compound 21 (Galeeva, R. N. et al. *Khim. Farm. Zh.* 1998, 32, 31; Kermack, W. O. et. al. *J. Chem. Soc.* 1942, 726, the disclosures of which are herein incorporated by reference).

SCHEME 5

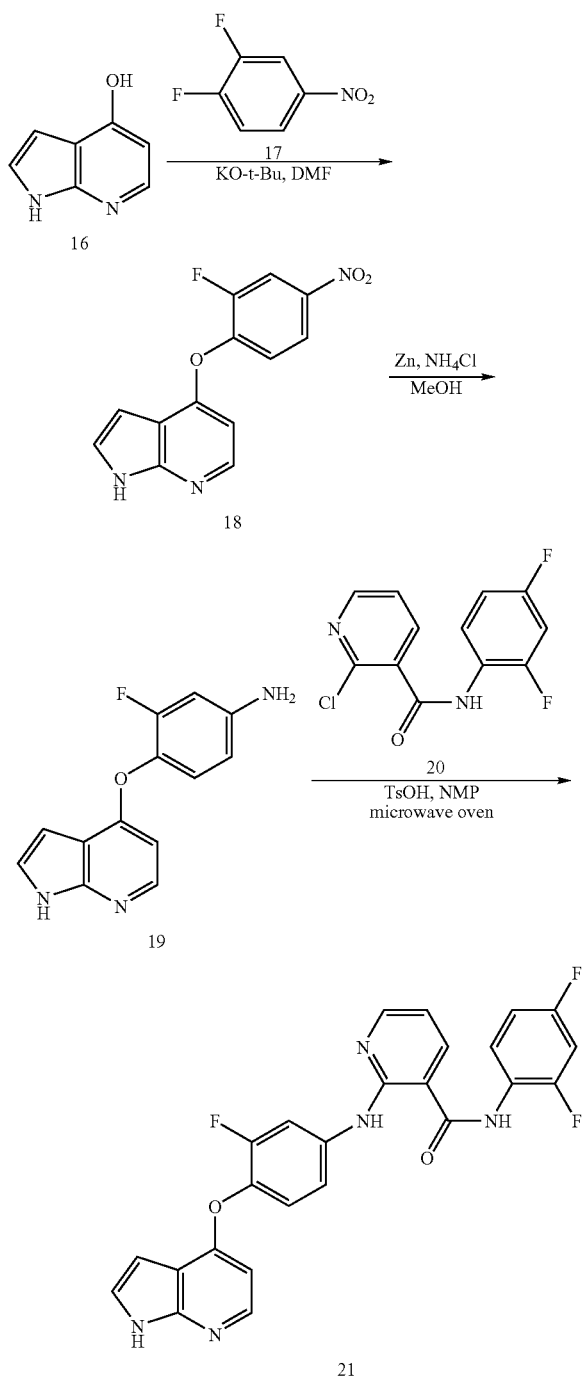

SCHEME 6

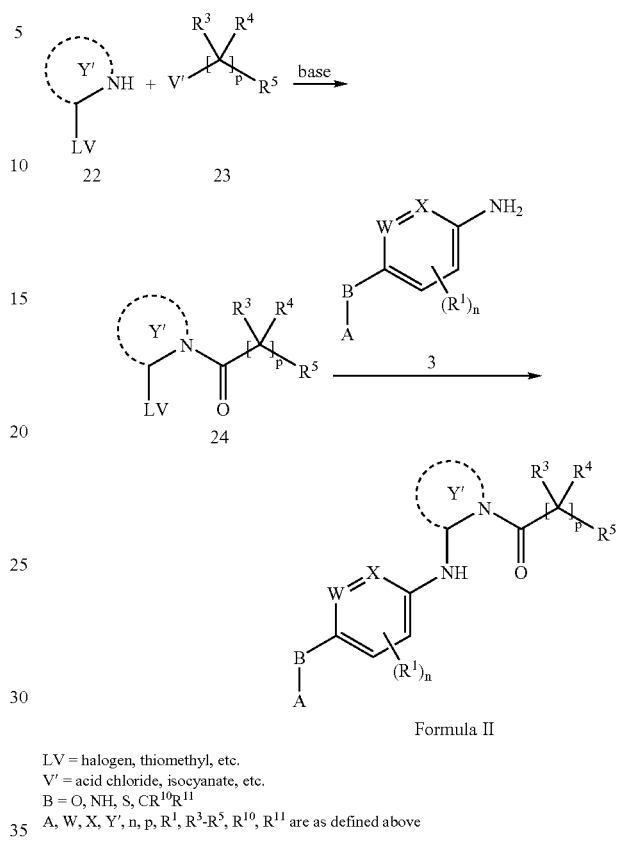

Formula II

LV = halogen, thiomethyl, etc.
V' = acid chloride, isocyanate, etc.
B = O, NH, S, CR$^{10}$R$^{11}$
A, W, X, Y', n, p, R$^1$, R$^3$-R$^5$, R$^{10}$, R$^{11}$ are as defined above Schemes 7 and 8 describe the preparation of specific examples of Formula II. Thus, treatment of 2-thiomethylimidazole (25, prepared according to Nicolaou, K. C. et. al. *J. Am. Chem. Soc.* 2004, 126, 5192, herein incorporated by reference) with commercially available 4-fluorophenylacetyl chloride (26) under basic conditions can furnish intermediate 27. Combining intermediate 27 with the aniline derivative 19 (from Scheme 5) under acidic conditions (Zhong, Z. et. al. *Angew. Chem. Int. Ed.* 2003, 42, 3005, herein incorporated by reference) should provide the desired product 28 (Scheme 8).

In general, compounds of Formula II may be prepared according to Scheme 6. A nitrogen bearing 5-membered heterocycle 22 with a leaving group at the α-position can react with a compound 23 (such as an acyl chloride or an isocyanate) under basic conditions to form intermediate 24. The desired compounds of Formula II can then be obtained by combining intermediate 24 with an appropriately substituted aniline derivative 3 (prepared according to Scheme 1) using methods known to one skilled in the art.

SCHEME 7

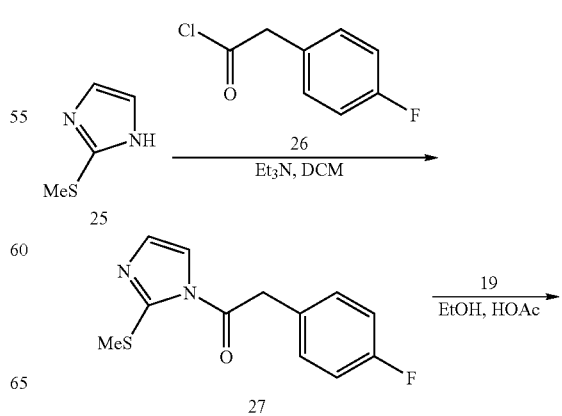

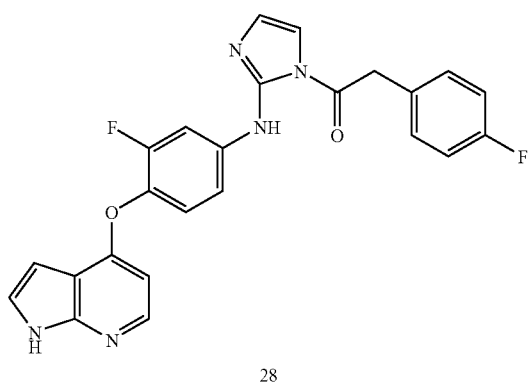

28

Alternatively, 2-thiomethylimidazole (25) can be treated with a commercially available isocyanate 29 (Scheme 8) to generate intermediate 30. Compound 30 can then be transformed to the desired product 31 under acidic conditions (Zhong, Z. et. al. *Angew. Chem. Int. Ed.* 2003, 42, 2005).

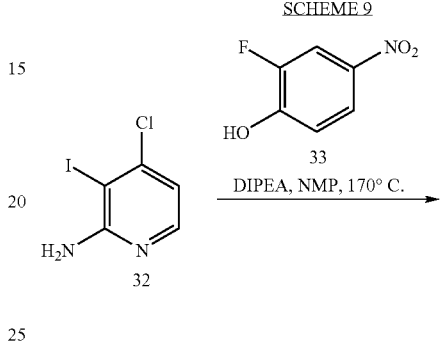

The pyridine derivative 39 can be prepared according to the synthetic route outlined in Scheme 9. Thus, 4-chloro-3-iodopyridin-2-amine, derived from ortho lithiation of (4-chloro-pyridin-2-yl)-carbamic acid tert-butyl ester (CB Research and Development, Inc) and subsequent N—Boc deprotection, can be treated with phenol 33 to generate compound 34. Sonagashira coupling of intermediate 34 with trimethylsilyl acetylene in the presence of a palladium catalyst, followed by reduction of the nitro group can provide the acetylene derivative 35. Palladium-mediated coupling of 35 with commercially available ethyl 2-chloronicotinate (36) in the presence of a base (e.g., potassium carbonate, Hunig's base, or triethylamine) can provide intermediate 37. Base-promoted hydrolysis of the ester group of 37 followed by coupling of the requisite carboxylic acid intermediate with commercially available 2,4-difluorobenzenamine (38), under standard peptide coupling conditions can furnish the desired compound 39.

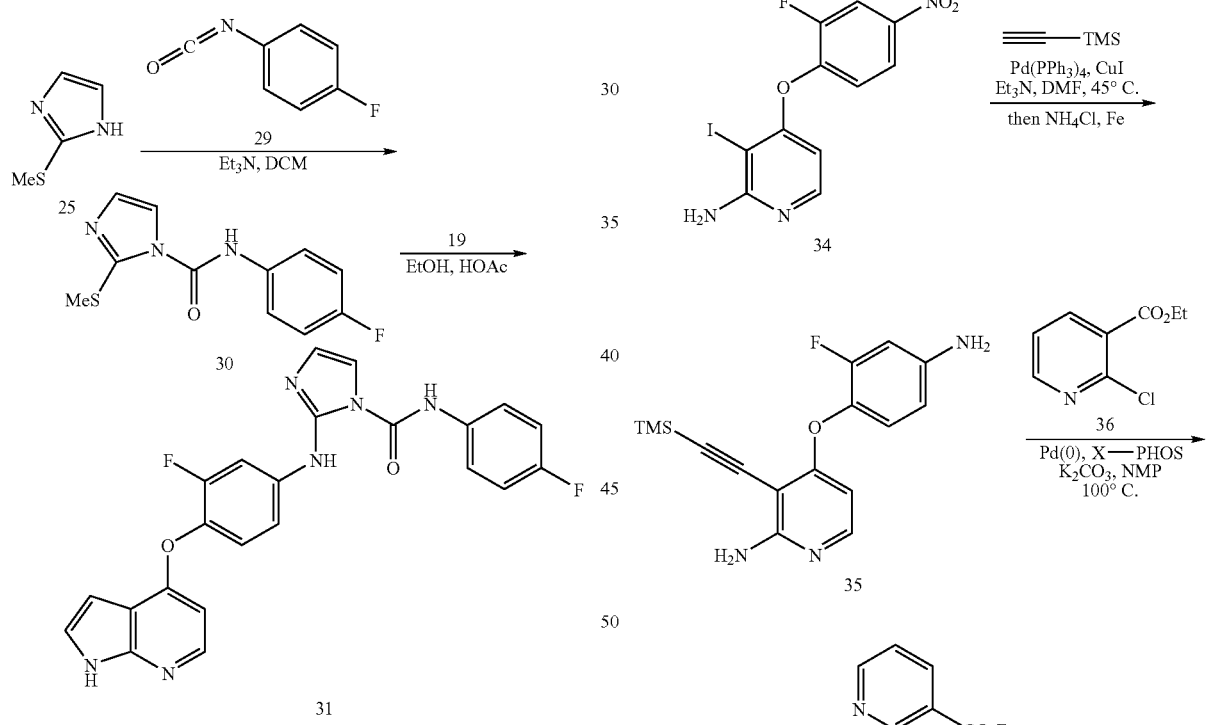

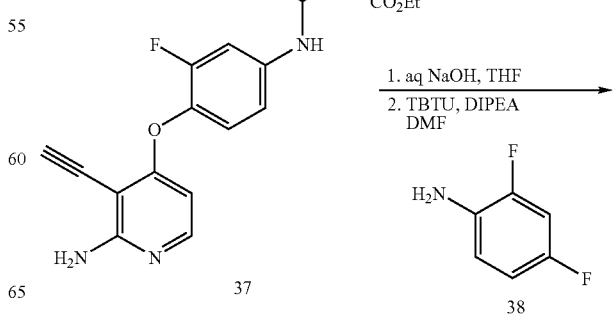

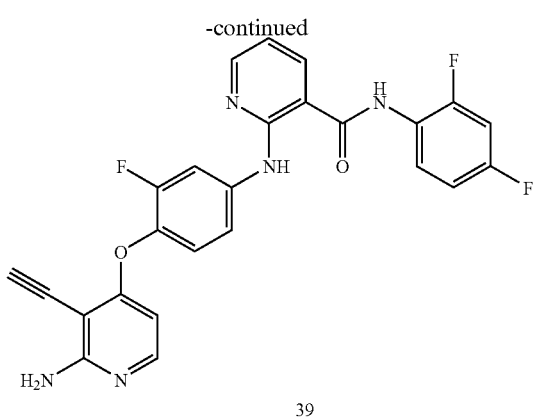

Scheme 10 depicts the synthesis of compounds 42 (X=CH₂ or NH). The pyrrole borane 40 (Takigi, J. et. al. *Tetrahedron Lett.* 2002, 43, 5649-5651, herein incorporated by reference) can be acylated with compound 26 (Scheme 7) to provide an intermediate 41. The intermediate 41 can be coupled with an aniline 19 (Scheme 5) to afford the desired product 42a (X=CH₂) (Chan, D. M. T. et. al. *Tetrahedron Lett.* 2003, 44, 3863-3865). Alternatively, 2-bromopyrrole (43, Chen, W. et. al. *Org. Synth.* 1992, 70, 151-156) can react with 4-fluorophenyl isocyanate (29, Scheme 8) to furnish intermediate 44, which can then be converted to 45 under standard Pd(0)-catalyzed coupling conditions with bis(pinacolato)diboron (Ishiyama, T. et. al. *J. Org. Chem.* 1995, 60, 7508-7510). The compound 45 can be transformed to 42b (X=NH) according to the conditions described above.

Scheme 11 illustrates the preparation of compound 50. Thus, the thiomethyl-substituted pyrimidine 46 (Alpha Aesar), can be treated with aniline 12 (from Scheme 4) under acidic conditions to give intermediate 47. Saponification of 47 with a base, such as sodium hydroxide can provide the carboxylate salt 48, which could be coupled with commercially available 2,4-difluoroaniline to give intermediate 49. Treatment of 49 with bis(trifluoroacetoxy)iodobenzene (as described in Scheme 4) can afford compound 50.

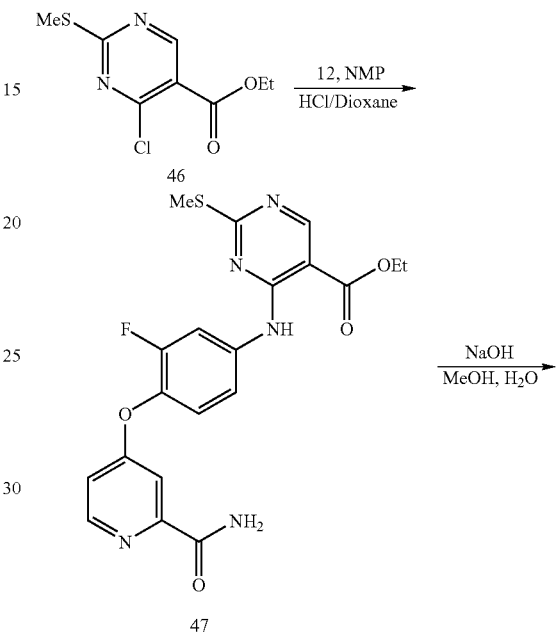

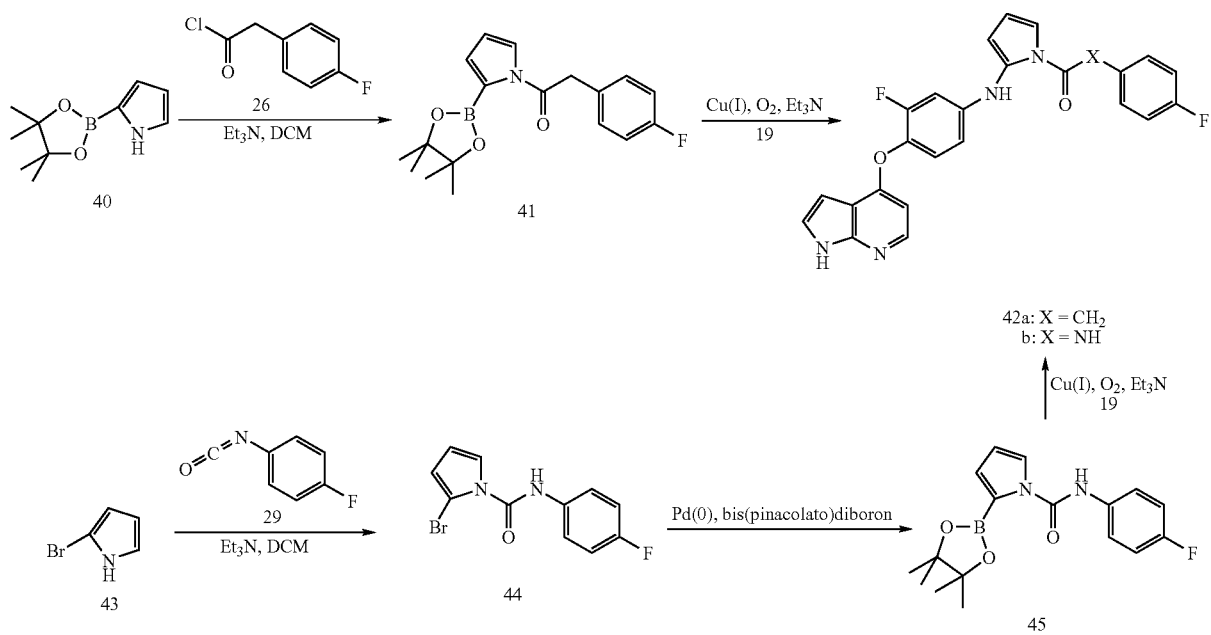

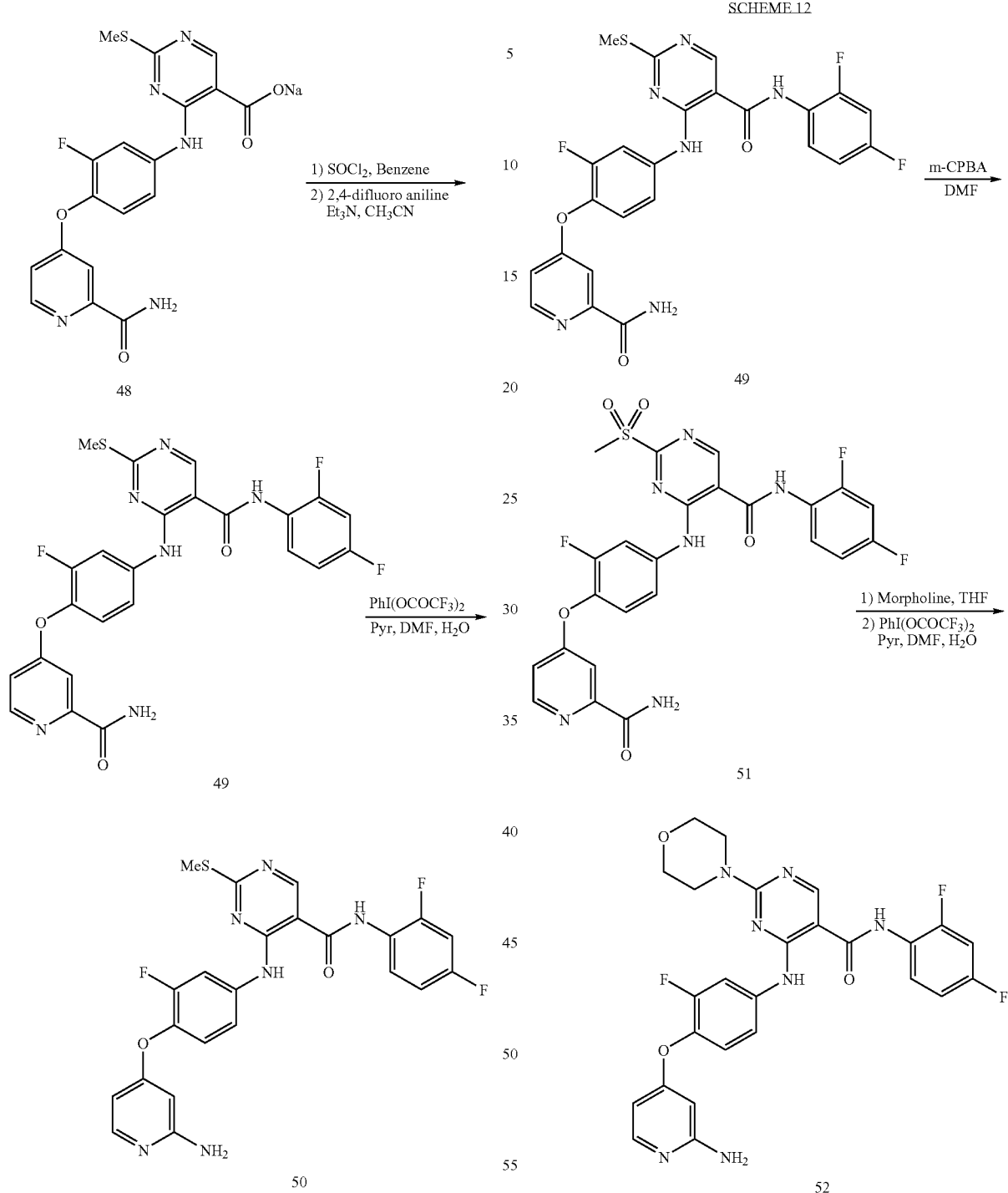

Scheme 12 illustrates the preparation of another specific example of Formula I. Thus, the thiomethyl-substituted pyrimidine 49 (Scheme 11) can be oxidized with, for example m-chloroperoxybenzoic acid in DMF to give sulfone 51. The sulfone moiety can then be displaced with a nucleophile, such as morpholine, followed by treatment with bis(trifluoroacetoxy)iodobenzene (as described in Scheme 4) to provide compound 52.

Assays

The pharmacological properties of the compounds of this invention may be confirmed by a number of pharmacological assays. The exemplified pharmacological assays which follow have been carried out with the compounds according to the invention and/or their pharmaceutically acceptable salts.

| Met Kinase assay | |
| --- | --- |
| Reagents | Substrate Mix Final Concentration |
| Stock Solution | |
| Tris-HCl, (1 M, pH 7.4) | 20 mM |
| $MnCl_2$ (1 M) | 1 mM |
| DTT (1 M) | 1 mM |
| BSA (100 mg/ml) | 0.1 mg/ml |
| polyGlu$_4$/tyr (10 mg/ml) | 0.1 mg/mL |
| ATP (1 mM) | 1 μM |
| γ-ATP (10 μCi/μl) | 0.2 μCi/ml |
| Buffer | Enzyme mix |
| 20 ul 1 M DTT | 4 ul GST/Met enzyme (3.2 mg/ml) = 10 ng/rxn |
| 200 ul 1 M Tris-HCL, pH 7.4 | qs 12 ml Buffer |
| 20 ul 100 mg/ml BSA | |
| qs 20 ml $H_2O$ | |

Incubation mixtures employed for the Met kinase assay contain the synthetic substrate polyGlu:Tyr, (4:1), ATP, ATP-γ-$^{33}$P and buffer containing $Mn^{++}$ and/or $Mg^{++}$, DTT, BSA, and Tris buffer. Reactions are incubated for 60 minutes at 27° C. and stopped by the addition of cold trichloroacetic acid (TCA) to a final concentration 4%. TCA precipitates are collected onto GF/C unifilter plates (Packard Instrument Co., Meriden, Conn.) using a Filtermate universal harvester (Packard Instrument Co., Meriden, Conn.) and the filters are quantitated using a TopCount 96-well liquid scintillation counter (Packard Instrument Co., Meriden, Conn.). Dose response curves are generated to determine the concentration required to inhibit 50% of kinase activity ($IC_{50}$). Compounds are dissolved at 10 mM in dimethyl sulfoxide (DMSO) and evaluated at six concentrations, each in quadruplicate. The final concentration of DMSO in the assay is 1%. $IC_{50}$ values are derived by non-linear regression analysis and have a coefficient of variance (SD/mean, n=6)=16%.

Preferred compounds of the invention inhibit the Met kinase enzyme with $IC_{50}$ values between 0.01 to 100 μM. More preferred compounds have $IC_{50}$ values less than 1.0 μM, and most preferably, less than about 0.5 μM.

The following examples and preparations describe the manner and process of making and using the invention and are illustrative rather than limiting. It should be understood that there may be other embodiments which fall within the spirit and scope of the invention as defined by the claims appended hereto.

EXAMPLES

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Analytical Reverse Phase (RP) HPLC was performed using a Phenomenex Luna C18 S5 4.6 mm×50 mm column or a YMC S5 ODS 4.6×50 mm column. In each case a 4 min linear gradient (from 100% A: % 0 B to 0% A: 100% B) was used with the following mobile phase system: A=90% $H_2O$/MeOH+0.2% $H_3PO_4$; B=90% MeOH/$H_2O$+0.2% $H_3PO_4$ at flow rate=4 mL/min and detection at 220 nm.

Preparative Reverse Phase (RP) HPLC was performed with a linear gradient elution using 10% methanol, 90% water, 0.1% TFA (solvent A) and 90% methanol, 10% water, 0.1% TFA (solvent B) and detection at 220 nm on one of the following columns: A—Shimadzu S5 ODS-VP 20×100 mm column with a flow rate of 20 mL/min; B—YMC S5 ODS 30×100 mm column with a flow rate of 20 mL/min; C—Phenomonex 30×250 mm column with a flow rate of 10 mL/min; D—YMC S5 ODS 20×250 mm column with a flow rate of 10 mL/min; E—YMC S10 ODS 50×500 mm column with a flow rate of 50 mL/min; or F—YMC S10 ODS 30×500 mm column with a flow rate of 20 mL/min.

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

The following abbreviations are used for common reagents: Boc or BOC: t-butyl carbamate; Fmoc: 9H-fluorenylmethyl carbamate; TEA: triethylamine; NMM: N-methylmorpholine; Ms: methanesulfonyl; DIEA or DIPEA: diisopropylethylamine or Hunig's base; NMP: N-methylpyrrolidinone; BOP reagent: benzotriazol-1-yloxytris(trimethylamino)phosphonium hexafluorophosphate; DCC: 1,3-dicyclohexylcarbodiimide; EDCI: 1-(dimethylaminopropyl)-3-ethylcarbodiimide hydrochloride; RT or rt: room temperature; $t_R$: retention time; h: hour(s); min: minute(s); PyBroP: bromotripyrrolidinophosphonium hexafluorophosphate; TBTU: O-(1H-benzotriazol-1-yl)-N,N,N',N'-tetramethyluronium tetrafluoroborate; DMAP: 4-N,N-dimethylaminopyridine; HOBt or HOBT: hydroxybenzotriazole; Na(OAc)$_3$BH: sodium triacetoxyborohydride; HOAc: acetic acid; TFA: trifluoroacetic acid; LiHMDS: lithium bis(trimethylsilyl)amide; DMSO: dimethyl sulfoxide; MeCN: acetonitrile; MeOH: methanol; EtOAc: ethyl acetate; DMF: dimethyl formamide; THF: tetrahydrofuran; DCE: 1,2-dichloroethane; Et$_2$O: diethyl ether; DCM: dichloromethane or methylene chloride; m-CPBA: 4-chloroperoxybenzoic acid.

Example 1

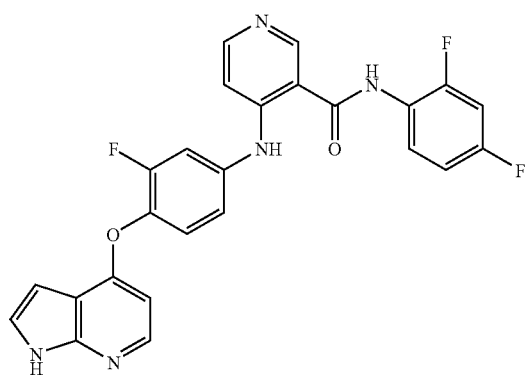

4-(4-(1H-Pyrrolo[2,3-b]pyridin-4-yloxy)-3-fluorophenylamino)-N-(2,4-difluorophenyl)nicotinamide, hydrochloride salt

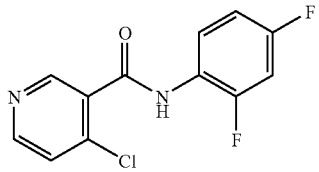

A) 4-Chloro-N-(2,4-difluorophenyl)nicotinamide

To a mixture of 4-chloronicotinic acid (Lancaster Synthesis, 0.31 g, 2.0 mmol) and 2,4-difluoroaniline (Aldrich, 0.20 mL, 2.0 mmol) in anhydrous dichloromethane (5 mL) was added bromo-tris-pyrrolidino-phosphonium hexafluorophosphate (PyBroP®, Novabiochem, 1.4 g, 3.0 mmol) followed by diisopropylethylamine (1.1 mL, 6.4 mmol). Anhydrous DMF (2 mL) was added to the mixture and the reaction stirred at ambient temperature. After 255 hours, the reaction mixture was partitioned between chloroform and 10% LiCl (aq). The organic layer was washed three times with 10% LiCl (aq), dried over anhydrous MgSO$_4$, then concentrated in vacuo. Purification of the residue by flash column chromatography (SiO$_2$, eluting with 1:1 hexane/EtOAc) afforded the desired compound (0.23 g, 42%). $^1$H NMR (DMSO-d$_6$) δ 10.58 (s, 1H), 8.78 (s, 1H), 8.66 (d, 1H, J=5.4 Hz), 7.82-7.88 (m, 1H), 7.71 (d, 1H, J=5.4 Hz), 7.37-7.43 (m, 1H), 7.14-7.19 (m, 1H);

MS(ESI$^+$) m/z 269 (M+H)$^+$.

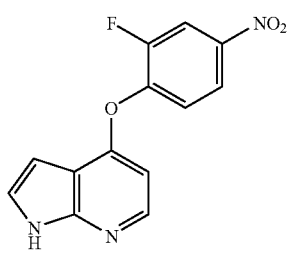

B) 4-(2-Fluoro-4-nitrophenoxy)-1H-pyrrolo[2,3-b]pyridine

A mixture of 4-chloro-1H-pyrrolo[2,3-b]pyridine (457 mg, 3.0 mmol, prepared generally according to Thibault, C. et al. *Org. Lett.* 2003, 5, 5023) and 2-fluoro-4-nitrophenol (706 mg, 4.5 mmol), and N,N-diisopropylethylamine (580 mg, 4.5 mmol) in 1-methyl-2-prolidinone (NMP) (3 mL) was heated at 200° C. under microwave irradiation for 1 h. The mixture was diluted with ethyl acetate (150 mL), washed with sat. aq. KH$_2$PO$_4$ solution, and Na$_2$CO$_3$ (aq. 1 M), and dried over Na$_2$SO$_4$. The product was purified by flash column chromatography (silica gel, eluting with CH$_2$Cl$_2$ to 30% EtOAc/CH$_2$Cl$_2$) to afford the desired compound (350 mg, 43%) as a brown solid. MS(ESI$^+$) m/z 274 (M+H)$^+$.

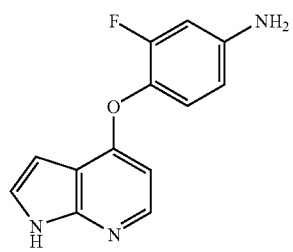

C) 4-(1H-Pyrrolo[2,3-b]pyridin-4-yloxy)-3-fluorobenzenamine

To a suspension of 4-(2-fluoro-4-nitrophenoxy)-1H-pyrrolo[2,3-b]pyridine (300 mg, 1.1 mmol) in tetrahydrofuran (5 mL) and methanol (10 mL), was added zinc powder (350 mg, 5.5 mmol) and ammonium chloride (294 mg, 5.5 mmol). The mixture was stirred at rt overnight. The mixture was filtered through a pad of Celite®, rinsed with methanol. The filtrate was concentrated in vacuo and the resulting residue was purified by flash column chromatography (silica gel, 1-5% MeOH in CH$_2$Cl$_2$) to afford the desired product (205 mg, 77%) as an off-white solid. MS(ESI$^+$) m/z 244 (M+H)$^+$.

D) 4-(4-(1H-Pyrrolo[2,3-b]pyridin-4-yloxy)-3-fluorophenylamino)-N-(2,4-difluorophenyl)nicotinamide, hydrochloride salt A homogeneous mixture of 4-(1H-pyrrolo[2,3-b]pyridin-4-yloxy)-3-fluorobenzenamine (0.039 g, 0.16 mmol), 4-chloro-N-(2,4-difluorophenyl)nicotinamide (0.043 g, 0.16 mmol) and p-toluenesulfonic acid monohydrate (Aldrich, 0.024 g, 0.13 mmol), in anhydrous NMP (1 mL), was microwaved in a CEM Explorer PLS microwave system (300 W). The temperature was measured with an IR temperature sensor and maintained at 160° C. After one hour, the reaction mixture was partitioned between chloroform and brine. The aqueous layer was extracted twice with chloroform, and the combined organic layers were concentrated in vacuo. The resultant residue was purified by preparative HPLC (YMC S10 ODS, 30×500 mm, 30 minute gradient from 34% to 90% aqueous methanol with 0.1% TFA). The appropriate fractions were combined and lyophilized to an off-white solid that was dissolved in anhydrous THF (1 mL), cooled to 0° C. and treated with HCl (4 N in dioxane, 1.0 mL, 4.0 mmol). The reaction mixture was stirred for ten minutes, before being lyophilized to afford the title compound (0.015 g, 18%) as an off-white solid.

$^1$H NMR (DMSO-d$_6$) δ 12.29 (s, 1H), 10.96 (s, 1H), 10.80 (s, 1H), 9.01 (s, 1H), 8.33 (d, 1H, J=7.2 Hz), 8.17 (d, 1H,

J=5.9 Hz), 7.11-7.67 (m, 8H), 6.59 (d, 1H, J=5.8 Hz), 6.38-6.39 (m, 1H); HRMS(ESI⁺), 476.1334 (M+H)⁺ calc, 476.1342 (M+H)⁺ found.

Example 2

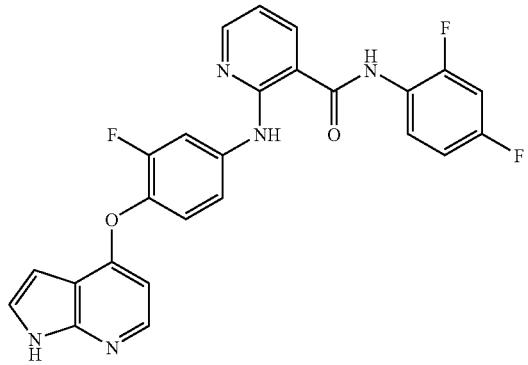

2-(4-(1H-Pyrrolo[2,3-b]pyridin-4-yloxy)-3-fluorophenylamino)-N-(2,4-difluorophenyl)nicotinamide, hydrochloride salt 4-(1H-Pyrrolo[2,3-b]pyridin-4-yloxy)-3-fluorobenzenamine (0.073 g, 0.30 mmol, Compound C of Example 1) was converted to the title compound (0.032 g, 21%) in a manner similar to the preparation of 4-(4-(1H-pyrrolo[2,3-b]pyridin-4-yloxy)-3-fluorophenylamino)-N-(2,4-difluorophenyl) nicotinamide hydrochloride salt (Compound D of Example 1), except that 2-chloro-N-(2,4-difluorophenyl)nicotinamide (Maybridge, 0.081 g, 0.30 mmol) was used instead of 4-chloro-N-(2,4-difluorophenyl)nicotinamide. ¹H NMR (DMSO-d₆) δ 12.83 (s, 1H), 10.75 (s, 1H), 10.52 (s, 1H), 8.28-8.41 (m, 3H), 8.15 (dd, 1H, J=13.6, 2.2 Hz), 7.32-7.56 (m, 5H), 7.09-7.13 (m, 1H), 6.98-7.01 (m, 1H), 6.72 (d, 1H, J=6.5 Hz), 6.48-6.49 (m, 1H); HRMS(ESI⁺), 476.1334 (M+H)⁺ calc, 476.1350 (M+H)⁺ found.

Example 3

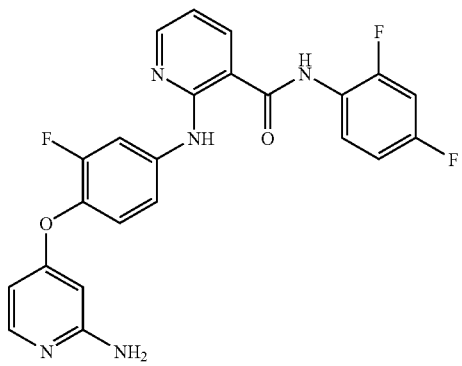

2-(4-(2-Aminopyridin-4-yloxy)-3-fluorophenylamino)-N-(2,4-difluorophenyl)nicotinamide, hydrochloride salt

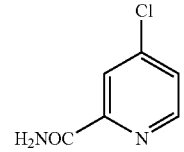

A) 4-Chloropicolinamide

A heterogeneous mixture of 4-chloropicolinic acid (TCI America, 5.4 g, 34.2 mmol, 1.0 eq) and thionyl chloride (30 mL) was heated at 80° C. for 2 h. The reaction mixture was cooled to room temperature and concentrated in vacuo. The residue was treated with an ammonia in MeOH solution (7N, 45 mL) in an ice bath and the reaction mixture was stirred for 15 minutes. The ice bath was then removed and the reaction was warmed to room temperature and then stirred for 3 h. The reaction mixture was concentrated in vacuo and the residue purified by recrystallization from EtOAc to afford the desired product (5.14 g, 96%) as a solid.
¹H NMR (DMSO-d₆) δ 8.61-8.63 (m, 1H), 8.21 (m, 1H), 8.03-8.04 (m, 1H), 7.76-7.83 (m, 2H); MS(ESI⁺) m/z 157 (M+H)⁺.

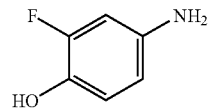

B) 2-Fluoro-4-aminophenol

A mixture of platinum oxide (0.010 g) and 2-fluoro-4-nitrophenol (Aldrich, 1.24 g, 7.78 mmol, 1.0 eq) in MeOH (100 mL) was stirred under a H₂ atmosphere at 50 psi at room temperature. The reaction mixture was filtered through Celite® and the filtrate concentrated in vacuo to afford the desired compound (1.00 g, 100%), as a solid which was used without further purification. ¹H NMR (DMSO-d₆) δ 8.57 (s, 1H), 6.46-6.47 (m, 1H), 6.33-6.46 (m, 1H), 6.19-6.21 (m, 1H), 4.79 (s, 2H);
MS(ESI⁺) m/z 128 (M+H)⁺.

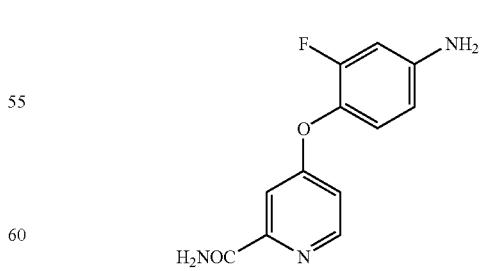

C) 4-(4-Amino-2-fluorophenoxy)picolinamide

A solution of 4-amino-2-fluorophenol (0.81 g, 6.4 mmol, 1.0 eq) in DMF (6.5 mL) was treated with potassium tert-butoxide (0.79 g, 7.1 mmol, 1.1 eq) at room temperature and the reaction mixture was stirred for 1 h. 4-Chloropicolinamide (1.0 g, 6.4 mmol, 1.0 eq) was added and the reaction mixture was heated to 110° C. for 8 h. The reaction was cooled to room temperature and the reaction mixture quenched with water. The resulting heterogeneous solution was filtered and the solid material was washed with water. The solid was triturated with a small amount of MeOH followed by Et$_2$O. The solid was filtered and dried in vacuo to afford the desired product (1.3 g, 82%) as a solid. $^1$H NMR (DMSO-d$_6$) δ 8.49-8.50 (m, 1H), 8.12 (br s, 1H), 7.71 (br s, 1H), 7.35-7.36 (m, 1H), 7.14-7.16 (m, 1H), 7.01-7.06 (m, 1H), 6.44-6.47 (m, 2H), 5.53 (s, 2H); MS(ESI$^+$) m/z 248 (M+H)$^+$.

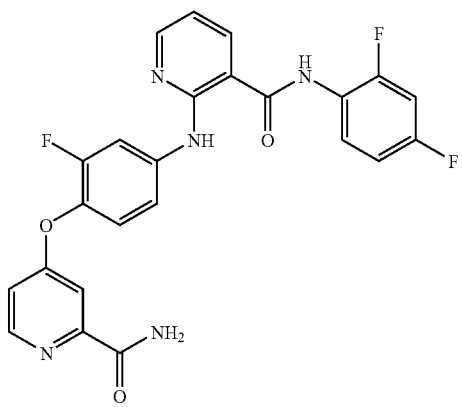

D) 2-(4-(2-Carbamoylpyridin-4-yloxy)-3-fluorophenylamino)-N-(2,4-difluorophenyl)nicotinamide 4-(4-Amino-2-fluorophenoxy)picolinamide (0.12 g, 0.50 mmol) was converted to the desired compound (0.088 g, 37%) in a manner similar to the preparation of 2-(4-(1H-pyrrolo[2,3-b]pyridin-4-yloxy)-3-fluorophenylamino)-N-(2, 4-difluorophenyl)-nicotinamide (Example 2). HRMS(ESI$^+$), 480.1283 (M+H)$^+$ calc, 480.1281 (M+H)$^+$ found.

E) 2-(4-(2-Aminopyridin-4-yloxy)-3-fluorophenylamino)-N-(2,4-difluorophenyl)nicotinamide, hydrochloride salt Bis(trifluoroacetoxy)iodobenzene (0.10 g, 0.23 mmol) was added to a solution of 2-(4-(2-carbamoylpyridin-4-yloxy)-3-fluorophenylamino)-N-(2,4-difluorophenyl)nicotinamide (0.080 g, 0.17 mmol), water (0.006 g, 0.33 mmol) and pyridine (0.27 mL, 3.33 mmol) in anhydrous DMF (5 mL) at room temperature. The reaction mixture was stirred for 69 hours before 6N aq HCl (2 mL) was added and the reaction stirred for an additional fifteen minutes. The mixture was extracted twice with Et$_2$O and the combined organic layers discarded. The aqueous layer was neutralized with 1M NaHCO$_3$(aq) then extracted with EtOAc. The combined organic layers were dried over anhydrous MgSO$_4$ and concentrated in vacuo. The resultant residue was purified by preparative HPLC (YMC S10 ODS, 30×500 mm, 30 minute gradient from 34% to 90% aqueous methanol with 0.1% TFA). The appropriate fractions were combined and lyophilized to an off-white solid that was dissolved in anhydrous THF (2 mL), cooled to 0° C. and treated with HCl (4N in dioxane, 1.0 mL, 4.0 mmol). The reaction mixture was stirred for ten minutes, before being lyophilized to afford the title compound (0.029 g, 35%) as an off-white solid. $^1$H NMR (DMSO-d$_6$) δ 10.72 (s, 1H), 10.49 (s, 1H), 8.32-8.40 (m, 2H), 8.13 (dd, 1H, J=13.7, 2.4 Hz), 7.82-7.92 (m, 3H), 7.29-7.53 (m, 4H), 7.05-7.15 (m, 1H), 6.97-7.01 (m, 1H), 6.64-6.66 (m, 1H), 6.12 (d, 1H, J=2.4 Hz); HRMS(ESI$^+$), 452.1334 (M+H)$^+$ calc, 452.1341 (M+H)$^+$ found.

Example 4

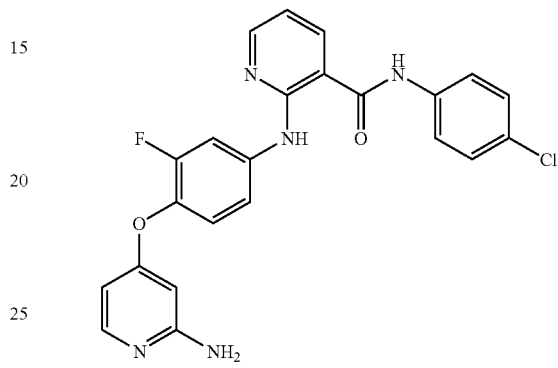

2-(4-(2-Aminopyridin-4-yloxy)-3-fluorophenylamino)-N-(4-chlorophenyl)nicotinamide, dihydrochloride salt

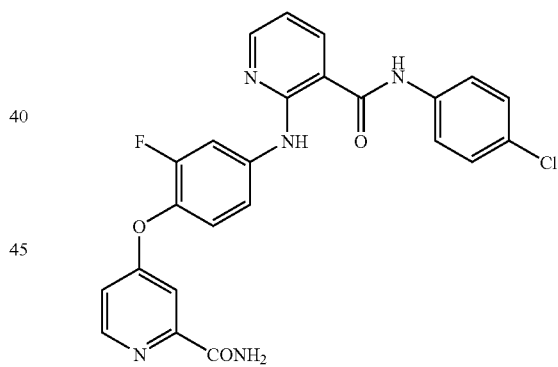

A) 2-(4-(2-Carbamoylpyridin-4-yloxy)-3-fluorophenylamino)-N-(4-chlorophenyl)nicotinamide 4-(4-Amino-2-fluorophenoxy)picolinamide (0.12 g, 0.50 mmol, Compound C of Example 3) was converted to the desired compound (0.090 g, 47%) in a manner similar to the preparation of 2-(4-(2-carbamoylpyridin-4-yloxy)-3-fluorophenylamino)-N-(2,4-difluorophenyl)-nicotinamide (Step D of Example 3), except that 2-chloro-N-(4-chlorophenyl) nicotinamide (Maybridge, 0.11 g, 0.40 mmol) was used instead of 2-chloro-N-(2,4-difluorophenyl)nicotinamide. HRMS(ESI$^+$), 478.1082 (M+H)$^+$ calc, 478.1059 (M+H)$^+$ found.

B) 2-(4-(2-Aminopyridin-4-yloxy)-3-fluorophenylamino)-N-(4-chlorophenyl)-nicotinamide, hydrochloride salt 2(4-(2-Carbamoylpyridin-4-yloxy)-3-fluorophenylamino)-N-(4-chlorophenyl)nicotinamide (0.088 g, 0.18 mmol) was converted to the title compound (0.022 g, 25%) in a manner similar to the preparation of 2-(4-(2-aminopyridin-4-yloxy)-3-fluorophenylamino)-N-(2,4-difluorophenyl) nicotinamide (Step E of Example 3). $^1$H NMR (DMSO-d$_6$) δ 10.65 (s, 1H), 10.40 (s, 1H), 8.36 (dd, 1H, J=4.9, 1.6 Hz), 8.25-8.28 (m, 1H), 8.11 (dd, 1H, J=13.6, 2.4 Hz), 7.71-7.92 (m, 5H), 7.29-7.45 (m, 4H), 6.98 (dd, 1H, J=7.7, 4.9 Hz), 6.65 (dd, 1H, J=7.3, 2.5 Hz), 6.13 (d, 1H, J=2.4 Hz); HRMS(ESI$^+$), 450.1148 (M+H)$^+$ calc, 450.1133 (M+H)$^+$ found.

B) 4-(4-(2-Aminopyridin-4-yloxy)-3-fluorophenylamino)-N-(2,4-difluorophenyl)nicotinamide, dihydrochloride salt 4-(4-(3-(2,4-Difluorophenylcarbamoyl)pyridin-4-ylamino)-2-fluorophenoxy)picolinamide (0.030 g, 0.062 mmol) was converted to the title compound (0.010 g, 34%) in a manner similar to the preparation of 2-(4-(2-aminopyridin-4-yloxy)-3-fluorophenylamino)-N-(2,4-difluorophenyl) nicotinamide (Step E of Example 3). $^1$H NMR (DMSO-d$_6$) δ 10.93 (s, 1H), 10.73 (s, 1H), 9.01 (s, 1H), 8.33 (d, 1H, J=6.6 Hz), 7.90-8.05 (m, 3H), 7.07-7.70 (m, 7H), 6.66 (dd, 1H, J=7.2, 2.3 Hz), 6.28 (s, 1H); HRMS(ESI$^+$), 452.1334 (M+H)$^+$ calc, 452.1332 (M+H)$^+$ found.

Example 5

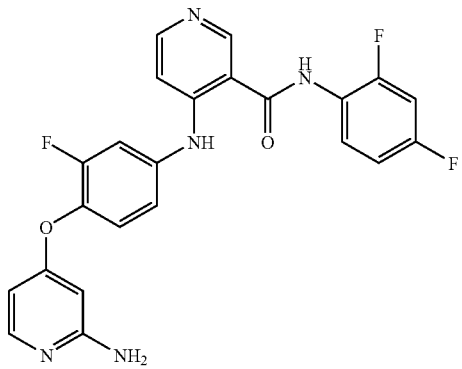

4-(4-(2-Aminopyridin-4-yloxy)-3-fluorophenylamino)-N-(2,4-difluorophenyl)nicotinamide, dihydrochloride salt

Example 6

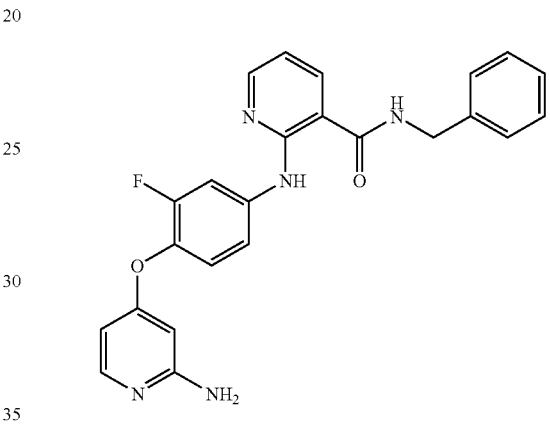

2-(4-(2-Aminopyridin-4-yloxy)-3-fluorophenyl amino)-N-benzylnicotinamide, dihydrochloride salt

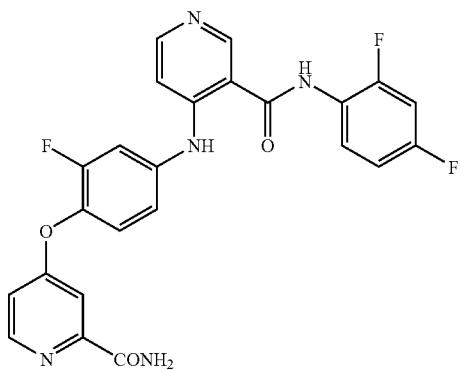

A) 4-(4-(3-(2,4-Difluorophenylcarbamoyl)pyridin-4-ylamino)-2-fluorophenoxy)picolinamide 4-(4-Amino-2-fluorophenoxy)picolinamide (0.12 g, 0.50 mmol, Compound C of Example 3) was converted to the desired compound (0.030 g, 12%) in a manner similar to the preparation of 4-(4-(1H-pyrrolo[2,3-b]pyridin-4-yloxy)-3-fluorophenylamino)-N-(2,4-di-fluorophenyl)nicotinamide (Step D of Example 1).
HRMS(ESI$^+$), 480.1284 (M+H)$^+$ calc, 480.1273 (M+H)$^+$ found.

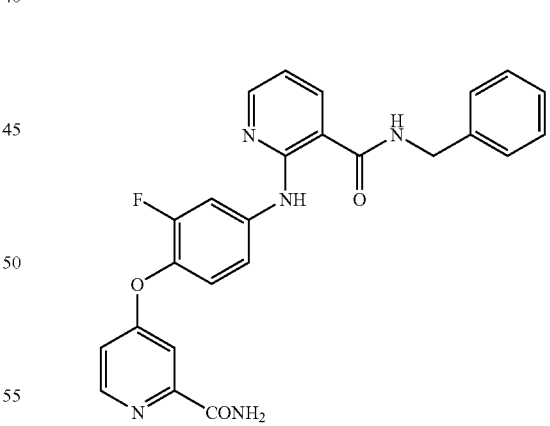

A) 4-(4-(3-(Benzylcarbamoyl)pyridin-2-ylamino)-2-fluorophenoxy)picolinamide 4-(4-Amino-2-fluorophenoxy)picolinamide (0.099 g, 0.40 mmol, Compound C of Example 3) was converted to the desired compound (0.080 g, 44%) in a manner similar to the preparation of 4-(4-(3-(2,4-difluorophenylcarbamoyl)pyridin-4-ylamino)-2-fluorophenoxy)picolinamide (Step D of Example 1), except that N-benzyl-2-chloronicotinamide (Maybridge, 0.099 g, 0.40 mmol) was used instead of 4-chloro-N-(2,4-difluorophenyl)nicotinamide. MS(ESI+) m/z 458 (M+H)+.

B) 2-(4-(2-Aminopyridin-4-yloxy)-3-fluorophenylamino)-N-benzylnicotinamide, dihydrochloride salt 4-(4-(3-(Benzylcarbamoyl)pyridin-2-ylamino)-2-fluorophenoxy)picolinamide (0.068 g, 0.15 mmol) was converted to the title compound (0.051 g, 69%) in a manner similar to the preparation of 2-(4-(2-aminopyridin-4-yloxy)-3-fluorophenylamino)-N-(2,4-difluorophenyl)nicotinamide (Step E of Example 3). $^1$H NMR (DMSO-$d_6$) δ 11.17 (s, 1H), 9.44 (t, 1H, J=5.7 Hz), 8.10-8.35 (m, 3H), 7.91 (d, 1H, J=7.2 Hz), 7.82 (br s, 2H), 7.15-7.42 (m, 7H), 6.90-6.94 (m, 1H), 6.65 (dd, 1H, J=7.2, 2.5 Hz), 6.12 (d, 1H, J=2.5 Hz), 4.45 (d, 2H, J=5.8 Hz); HRMS(ESI+), 430.1679 (M+H)+ calc, 430.1683 (M+H)+ found.

Example 7

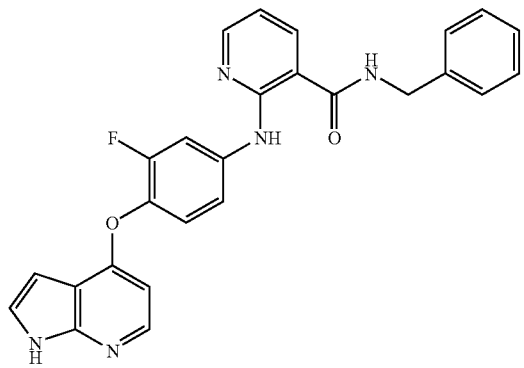

2-(4-(1H-Pyrrolo[2,3-b]pyridin-4-yloxy)-3-fluorophenylamino)-N-benzylnicotinamide, dihydrochloride salt 4-(1H-Pyrrolo[2,3-b]pyridin-4-yloxy)-3-fluorobenzenamine (0.043 g, 0.18 mmol, Compound C of Example 1) was converted to the title compound (0.015 g, 17%) in a manner similar to the preparation of 4-(4-(1H-pyrrolo[2,3-b]pyridin-4-yloxy)-3-fluorophenylamino)-N-(2,4-difluorophenyl) nicotinamide hydrochloride salt (Compound D of Example 1), except that N-benzyl-2-chloronicotinamide (Maybridge, 0.043 g, 0.18 mmol) was used instead of 4-chloro-N-(2,4-difluorophenyl)nicotinamide.

$^1$H NMR (DMSO-$d_6$) δ 12.55 (s, 1H), 11.18 (s, 1H), 9.37-9.45 (m, 1H), 8.10-8.36 (m, 4H), 7.18-7.54 (m, 8H), 6.90-6.97 (m, 1H), 6.64 (d, 1H, J=6.3 Hz), 6.40-6.44 (m, 1H), 4.46 (d, 2H, J=5.8 Hz); HRMS(ESI+), 454.1679 (M+H)+ calc, 454.1684 (M+H)+ found.

Example 8

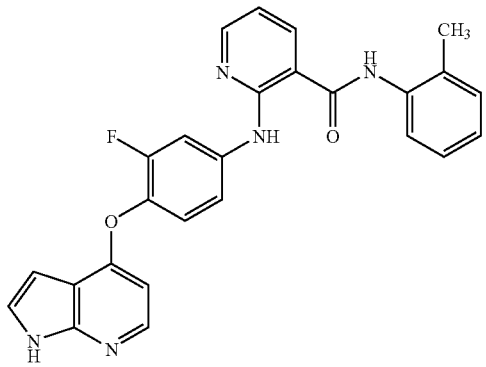

2-(4-(1H-Pyrrolo[2,3-b]pyridin-4-yloxy)-3-fluorophenylamino)-N-o-tolylnicotinamide, dihydrochloride salt

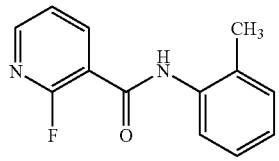

A) 2-Fluoro-N-o-tolylnicotinamide

A homogeneous mixture of 2-fluoronicotinic acid (Aldrich, 0.45 g, 3.2 mmol), in anhydrous THF (12 mL), was treated with oxalyl chloride (0.56 mL, 6.4 mmol) followed by anhydrous DMF (2 drops). After heating at reflux for 1.5 hours, the reaction mixture was concentrated in vacuo to afford 2-fluoronicotinoyl chloride as a residue which was used without further purification. The residue was dissolved in anhydrous THF (8 mL), anhydrous DCM (2 mL), pyridine (1 mL) and DMF (to a total volume of 16 mL). This homogeneous 2-fluoronicotinoyl chloride mixture (2 mL) was then added to a rapidly stirred mixture of o-toluidine (Aldrich, 0.17 mL, 1.6 mmol) in anhydrous THF (2 mL). After 15 hours, the reaction was quenched with water, and then extracted with 10% isopropanol in chloroform. The organic layer was washed once with sat. aq. NaHCO$_3$, once with sat. aq. NaCl, then dried over anhydrous Na$_2$SO$_4$ and concentrated in vacuo to afford the desired product (0.084 g, 91%) as a pale orange solid which was used without further purification. MS(ESI+) m/z 231 (M+H)+.

B) 2-(4-(1H-Pyrrolo[2,3-b]pyridin-4-yloxy)-3-fluorophenylamino)-N-o-tolylnicotinamide, dihydrochloride salt To a homogeneous mixture of 4-(1H-pyrrolo[2,3-b]pyridin-4-yloxy)-3-fluorobenzenamine (0.042 g, 0.17 mmol, Compound C of Example 1) and 2-fluoro-N-o-tolylnicotinamide (0.040 g, 0.17 mmol), in anhydrous 1,4-dioxane (0.22 mL) and anhydrous NMP (0.40 mL), was added HCl (4N in 1,4-dioxane, 0.18 mL, 0.72 mmol). The reaction mixture was heated in a sealed tube at 140° C. for 65 hours before being partitioned between chloroform and 10% LiCl (aq). The aqueous layer was extracted with chloroform and the combined organic layers were concentrated in vacuo. The resultant residue was purified by preparative (RP) HPLC (YMC S10 ODS, 30×500 mm, 30 minute gradient from 34% to 90% aqueous methanol with 0.1% TFA). The appropriate fractions were combined and concentrated in vacuo to a tan solid that was dissolved in anhydrous THF (1 mL), cooled to 0° C. and treated with HCl (4N in 1,4-dioxane, 0.5 mL, 2.0 mmol). The reaction mixture was stirred for ten minutes, before being lyophilized to afford the title compound (0.025 g, 29%) as a tan solid. $^1$H NMR (DMSO-$d_6$) δ 12.74 (s, 1H), 10.89 (s, 1H), 10.26 (s, 1H), 8.10-8.50 (m, 4H), 7.10-7.70 (m, 7H), 6.95-7.05 (m, 1H), 6.65-6.75 (m, 1H), 6.45-6.53 (m, 1H), 2.19 (s, 3H);

HRMS(ESI$^+$), 454.1674 (M+H)$^+$ calc, 454.1680 (M+H)$^+$ found.

Example 9

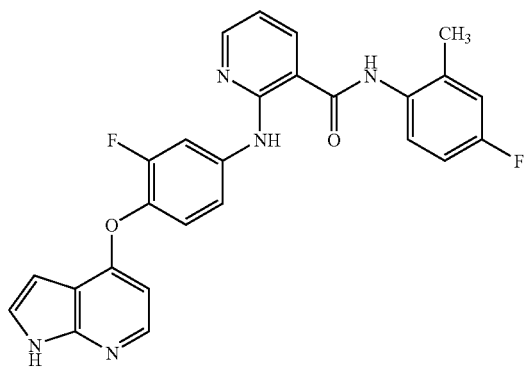

2-(4-(1H-Pyrrolo[2,3-b]pyridin-4-yloxy)-3-fluorophenylamino)-N-(4-fluoro-2-methylphenyl)nicotinamide, dihydrochloride salt

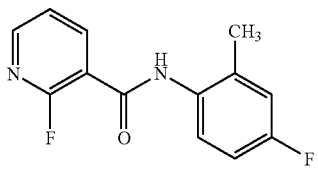

A)
2-Fluoro-N-(4-fluoro-2-methylphenyl)nicotinamide

4-Fluoro-2-methylaniline (Aldrich, 0.18 mL, 1.6 mmol) was converted to the desired compound (0.098 g, 99%) in a manner similar to the preparation of 2-fluoro-N-o-tolylnicotinamide (Step A of Example 8). MS(ESI$^+$) m/z 249 (M+H)$^+$.

B) 2-(4-(1H-Pyrrolo[2,3-b]pyridin-4-yloxy)-3-fluorophenylamino)-N-(4-fluoro-2-methylphenyl)nicotinamide, dihydrochloride salt 2-Fluoro-N-(4-fluoro-2-methylphenyl)nicotinamide (0.050 g, 0.20 mmol) was converted to the title compound (0.043 g, 42%) in a manner similar to the preparation of 2-(4-(1H-pyrrolo[2,3-b]pyridin-4-yloxy)-3-fluorophenylamino)-N-o-tolylnicotinamide (Step B of Example 8). $^1$H NMR (DMSO-$d_6$) δ 12.85 (s, 1H), 10.87 (s, 1H), 10.28 (s, 1H), 8.10-8.40 (m, 4H), 6.96-7.60 (m, 7H), 6.72 (d, 1H, J=6.5 Hz), 6.45-6.53 (m, 1H), 2.20 (s, 3H); HRMS(ESI$^+$), 472.1580 (M+H)$^+$ calc, 472.1590 (M+H)$^+$ found.

Example 10

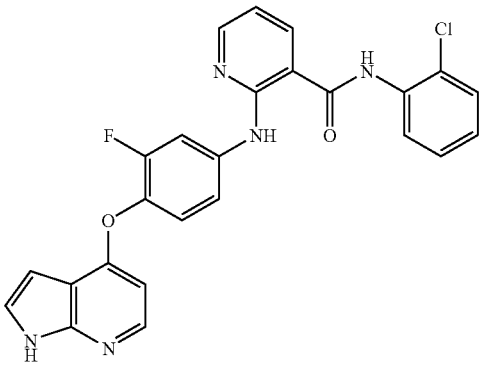

2-(4-(1H-Pyrrolo[2,3-b]pyridin-4-yloxy)-3-fluorophenylamino)-N-(2-chlorophenyl)nicotinamide, dihydrochloride salt

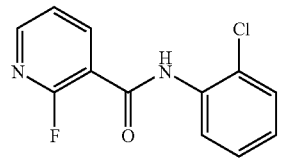

A) N-(2-Chlorophenyl)-2-fluoronicotinamide

2-Chloroaniline (Aldrich, 0.17 mL, 1.6 mmol) was converted to the desired compound (0.084 g, 84%) in a manner similar to the preparation of 2-fluoro-N-o-tolylnicotinamide (Step A of Example 8). MS(ESI$^+$) m/z 251 (M+H)$^+$.

B) 2-(4-(1H-Pyrrolo[2,3-b]pyridin-4-yloxy)-3-fluorophenylamino)-N-(2-chlorophenyl)nicotinamide, dihydrochloride salt N-(2-Chlorophenyl)-2-fluoronicotinamide (0.050 g, 0.20 mmol) was converted to the title compound (0.037 g, 36%) in a manner similar to the preparation of 2-(4-(1H-pyrrolo[2,3-b]pyridin-4-yloxy)-3-fluorophenylamino)-N-o-tolylnicotinamide (Step B of Example 8). $^1$H NMR (DMSO-$d_6$) δ 12.75

(s, 1H), 10.80 (s, 1H), 10.49 (s, 1H), 8.10-8.44 (m, 4H), 7.24-7.60 (m, 7H), 6.96-7.10 (m, 1H), 6.70 (m, 1H), 6.45-6.50 (m, 1H); HRMS(ESI+), 474.1133 (M+H)+ calc, 474.1129 (M+H)+ found.

Example 11

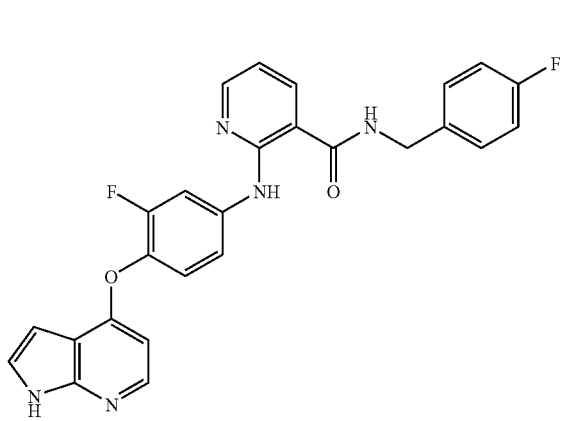

2-(4-(1H-Pyrrolo[2,3-b]pyridin-4-yloxy)-3-fluorophenylamino)-N-(4-fluorobenzyl)nicotinamide, dihydrochloride salt

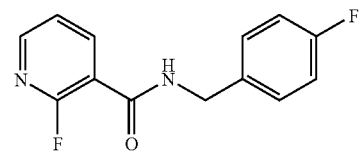

A) 2-Fluoro-N-(4-fluorobenzyl)nicotinamide

4-Fluorobenzylamine (Aldrich, 0.18 mL, 1.6 mmol) was converted to the desired compound (0.099 g, 100%) in a manner similar to the preparation of 2-fluoro-N-o-tolylnicotinamide (Step A of Example 8). MS(ESI+) m/z 249 (M+H)+.

B) 2-(4-(1H-Pyrrolo[2,3-b]pyridin-4-yloxy)-3-fluorophenylamino)-N-(4-fluorobenzyl)nicotinamide, dihydrochloride salt 2-Fluoro-N-(4-fluorobenzyl)nicotinamide (0.050 g, 0.20 mmol) was converted to the title compound (0.035 g, 35%) in a manner similar to the preparation of 2-(4-(1H-pyrrolo[2,3-b]pyridin-4-yloxy)-3-fluorophenylamino)-N-o-tolylnicotinamide (Step B of Example 8). $^1$H NMR (DMSO-$d_6$) δ 12.63 (s, 1H), 11.17 (s, 1H), 9.44 (t, 1H, J=5.8 Hz), 8.10-8.40 (m, 4H), 7.50-7.60 (m, 1H), 7.30-7.45 (m, 4H), 7.08-7.10 (m, 2H), 6.90-6.95 (m, 1H), 6.66 (d, 1H, J=6.3 Hz), 6.43-6.46 (m, 1H), 4.44 (d, 2H, J=5.7 Hz); HRMS(ESI+), 472.1585 (M+H)+ calc, 472.1587 (M+H)+ found.

Example 12

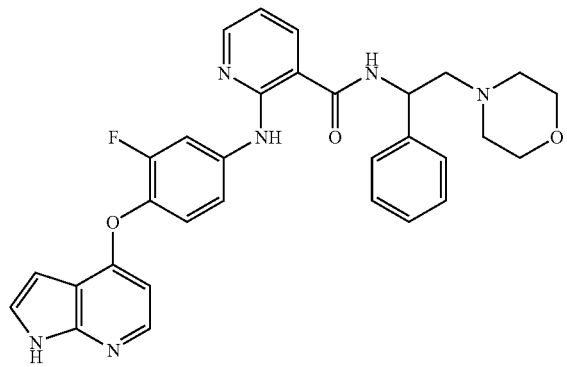

2-(4-(1H-Pyrrolo[2,3-b]pyridin-4-yloxy)-3-fluorophenylamino)-N-(2-morpholino-1-phenylethyl) nicotinamide, trihydrochloride salt

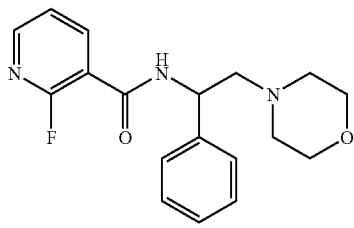

A) 2-Fluoro-N-(2-morpholino-1-phenylethyl)nicotinamide

2-Morpholin-4-yl-1-phenylethylamine (Array Biopharma, Inc., 0.33 g, 1.6 mmol) was converted to the desired compound (0.12 g, 87%) in a manner similar to the preparation of 2-fluoro-N-o-tolylnicotinamide (Step A of Example 8). HRMS(ESI+), 330.1618 (M+H)+ calc, 330.1620 (M+H)+ found.

B) 2-(4-(1H-Pyrrolo[2,3-b]pyridin-4-yloxy)-3-fluorophenylamino)-N-(4-fluorobenzyl)nicotinamide, hydrochloride salt 2-Fluoro-N-(2-morpholino-1-phenylethyl)nicotinamide (0.096 g, 0.29 mmol) was converted to the title compound (0.022 g, 13%) in a manner similar to the preparation of 2-(4-(1H-pyrrolo[2,3-b]pyridin-4-yloxy)-3-fluorophenylamino)-N-o-tolylnicotinamide (Step B of Example 8). $^1$H NMR (DMSO-$d_6$) δ 12.53 (s, 1H), 10.93-11.05 (m, 2H), 9.73 (d, 1H, J=7.8 Hz), 8.59 (dd, 1H, J=7.9, 1.3 Hz), 8.35 (dd, 1H, J=4.7, 1.4 Hz), 8.20 (d, 1H, J=6.2 Hz), 8.06-8.15 (m, 1H), 7.45-7.55 (m, 3H), 7.23-7.40 (m, 4H), 6.90-6.99 (m, 1H), 6.60 (d, 1H, J=6.2 Hz), 6.38-6.45 (m, 1H), 5.53-5.64 (m, 1H), 3.10-4.00 (m, 10H); HRMS(ESI⁺), 553.2363 (M+H)⁺ calc, 553.2368 (M+H)⁺ found.

Example 13

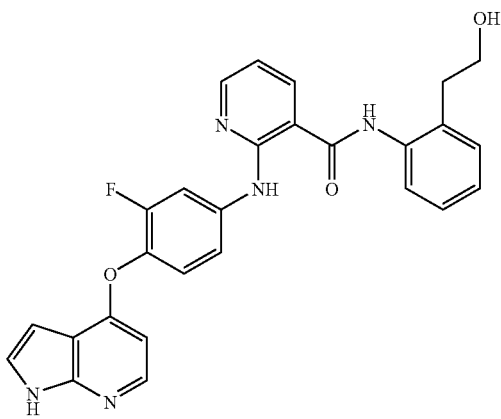

2-(4-(1H-Pyrrolo[2,3-b]pyridin-4-yloxy)-3-fluorophenylamino)-N-(2-(2-hydroxyethyl)phenyl)nicotinamide, bis(trifluoroacetic acid) salt

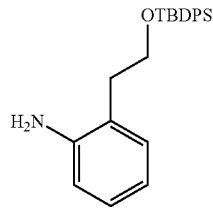

A) 2-(2-(tert-Butyldiphenylsilyloxy)ethyl)aniline

To a suspension of sodium hydride (60% dispersion in mineral oil, 0.29 g, 7.3 mmol) in anhydrous THF (30 mL), at 0° C., was added 2-aminophenethyl alcohol (Aldrich, 0.87 mL, 6.6 mmol). After 17 hours, during which time the reaction slowly warmed to room temperature, the mixture was poured into a saturated aqueous sodium chloride solution then extracted with EtOAc. The combined organic layers were dried over anhydrous MgSO₄ then concentrated in vacuo to a residue that was purified by silica gel flash chromatography, eluting with 3:1 hexane/EtOAc, to afford the desired compound as an oil (2.5 g, 100%). MS(ESI) m/z 376 (M+H)⁺.

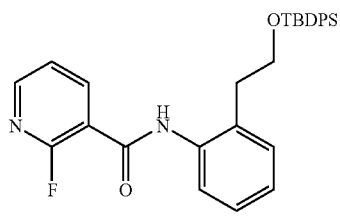

B) N-(2-(2-(tert-Butyldiphenylsilyloxy)ethyl)phenyl)-2-fluoronicotinamide

A mixture of 2-fluoronicotinic acid (Aldrich, 0.42 g, 2.9 mmol) in thionyl chloride (15 mL) was refluxed for two hours before being concentrated in vacuo to a residue which was used without further purification. The residue was dissolved in anhydrous DCM (5 mL) then added dropwise to a 0° C. solution of 2-(2-(tert-butyldiphenylsilyloxy)ethyl)aniline (1.10 g, 2.9 mmol) and TEA (0.43 mL, 3.1 mmol) in anhydrous DCM (15 mL). The reaction was then stirred at ambient temperature for 16 hours before being quenched with water then stirred for an additional thirty minutes. The layers were separated and the aqueous layer extracted with DCM. The combined organic layers were washed sequentially with water, saturated aqueous NaHCO₃, and brine before being dried over anhydrous MgSO₄, and then concentrated in vacuo. The resultant residue was purified by silica gel flash chromatography, eluting with 4:1 hexane/EtOAc, to afford the desired compound as a white solid (1.1 g, 72%). ¹H NMR (DMSO-d₆) δ 9.93 (s, 1H), 8.41 (d, 1H, J=4.4 Hz), 8.22 (t, 1H, J=7.6 Hz), 7.27-7.60 (m, 15H), 3.84 (t, 2H, J=6.7 Hz), 2.98 (t, 2H, J=6.7 Hz), 0.92 (s, 9H); HRMS(ESI⁺), 499.2217 (M+H)⁺ calc, 499.2230 (M+H)⁺ found.

C) 2-(4-(1H-Pyrrolo[2,3-b]pyridin-4-yloxy)-3-fluorophenylamino)-N-(2-(2-hydroxyethyl)phenyl)nicotinamide, bis(trifluoroacetic acid) salt To a homogeneous mixture of 4-(1H-pyrrolo[2,3-b]pyridin-4-yloxy)-3-fluorobenzenamine (0.040 g, 0.16 mmol, Compound C of Example 1) in anhydrous MeOH (3 mL), at 0° C., was added HCl (4 N in 1,4-dioxane, 0.30 mL, 1.2 mmol). The reaction was then stirred at room temperature for ten minutes before being concentrated in vacuo. The resultant solid was azeotroped from toluene, concentrated in vacuo to an off-white solid which was treated with anhydrous DMF (2 mL) and N-(2-(2-(tert-butyldiphenylsilyloxy)ethyl)phenyl)-2-fluoronicotinamide (0.90 g, 0.18 mmol) then heated at 110° C. for 121 hours. The reaction mixture was concentrated in vacuo to a residue which was purified by preparative (RP) HPLC (YMC S10 ODS, 30×500 mm, 30 minute gradient from 58% to 90% aqueous methanol with 0.1% TFA). The appropriate fractions were combined and concentrated in vacuo to afford the title compound (0.014 g, 15%) as a tan solid. ¹H NMR (DMSO-d₆) δ 11.89 (s, 1H), 10.86 (s, 1H), 10.43 (s, 1H), 8.35-8.45 (m, 1H), 8.24 (d, 1H, J=7.8 Hz), 8.05-8.14 (m, 2H), 7.13-7.48 (m, 7H), 6.95-6.99 (m, 1H), 6.35-6.41 (m, 1H), 6.24-6.29 (m, 1H), 3.59 (t, 2H, J=6.5 Hz), 2.74 (t, 2H, J=6.5 Hz); HRMS(ESI⁺), 484.1785 (M+H)⁺ calc, 484.1788 (M+H)⁺ found.

Example 14

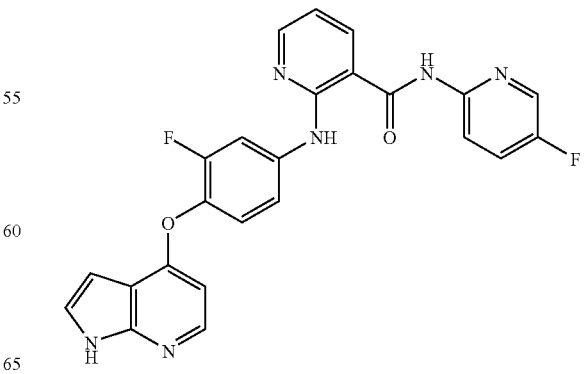

2-(4-(1H-Pyrrolo[2,3-b]pyridin-4-yloxy)-3-fluorophenylamino)-N-(5-fluoropyridin-2-yl)nicotinamide, bis(trifluoroacetic acid) salt

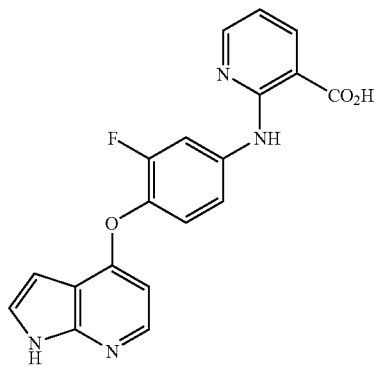

A) 2-(4-(1H-Pyrrolo[2,3-b]pyridin-4-yloxy)-3-fluorophenylamino)nicotinic acid To a homogeneous mixture of 4-(1H-pyrrolo[2,3-b]pyridin-4-yloxy)-3-fluorobenzenamine (0.10 g, 0.42 mmol, Compound C of Example 1) and 2-fluoronicotinic acid (Aldrich, 0.084 g, 0.59 mmol), in anhydrous NMP (0.50 mL), was added HCl (4N in 1,4-dioxane, 0.42 mL, 1.7 mmol). The mixture was microwaved in a CEM Explorer PLS microwave system (300 W). The temperature was measured with an IR temperature sensor and maintained at 120° C. for two hours followed by 140° C. for six hours. The reaction mixture was partitioned between water and EtOAc. The aqueous layer was extracted twice with EtOAc, and the combined organic layers were concentrated in vacuo. The resultant residue was purified by preparative (RP) HPLC (YMC S10 ODS, 30×500 mm, 30 minute gradient from 50% to 90% aqueous methanol with 0.1% TFA). The appropriate fractions were combined and concentrated in vacuo to afford the desired compound (0.13 g, 82%) as an off-white solid. $^1$H NMR (DMSO-$d_6$) δ 13.75 (br s, 1H), 12.11 (s, 1H), 10.60 (s, 1H), 8.40 (dd, 1H, J=4.7, 1.9 Hz), 8.24 (dd, 1H, J=7.7, 1.9 Hz), 8.10-8.20 (m, 2H), 7.30-7.49 (m, 3H), 6.90 (dd, 1H, J=7.7, 4.8 Hz), 6.48 (d, 1H, J=5.8 Hz), 6.31-6.40 (m, 1H); HRMS(ESI$^+$), 365.1050 (M+H)$^+$ calc, 365.1038 (M+H)$^+$ found.

B) 2-(4-(1H-Pyrrolo[2,3-b]pyridin-4-yloxy)-3-fluorophenylamino)-N-(5-fluoropyridin-2-yl)nicotinamide, bis(trifluoroacetic acid) salt To a homogeneous mixture of 2-(4-(1H-pyrrolo[2,3-b]pyridin-4-yloxy)-3-fluorophenylamino)nicotinic acid (0.036 g, 0.10 mmol), 2-amino-5-fluoropyridine (Aldrich, 0.22 g, 2.0 mmol) and TEA (0.020 g, 0.20 mmol) in anhydrous DCM (2 mL), cooled to 0° C., was added bis(2-oxo-3-oxazolidinyl)phosphinic chloride (0.025 g, 0.010 mmol). After 15 hours, during which time the reaction slowly warmed to room temperature, the mixture was partitioned between chloroform and water. The aqueous layer was extracted with chloroform before the organic layers were combined, washed with brine, dried over anhydrous MgSO$_4$, and concentrated in vacuo. The resultant residue was purified by preparative (RP) HPLC (YMC S10 ODS, 30×500 mm, 30 minute gradient from 58% to 90% aqueous methanol with 0.1% TFA). The appropriate fractions were combined and concentrated in vacuo to afford the desired compound (8.0 mg, 14%) as a pale yellow solid. $^1$H NMR (DMSO-$d_6$) δ 11.12 (s, 1H), 10.29 (s, 1H), 10.20 (s, 1H), 8.02-8.49 (m, 6H), 7.75-7.83 (m, 1H), 7.25-7.48 (m, 3H), 6.92 (dd, 1H, J=7.7, 4.8 Hz), 6.37-6.40 (m, 1H), 6.26 (dd, 1H, J=3.1, 1.7 Hz); HRMS(ESI$^+$), 459.1376 (M+H)$^+$ calc, 459.1367 (M+H)$^+$ found.

Example 15

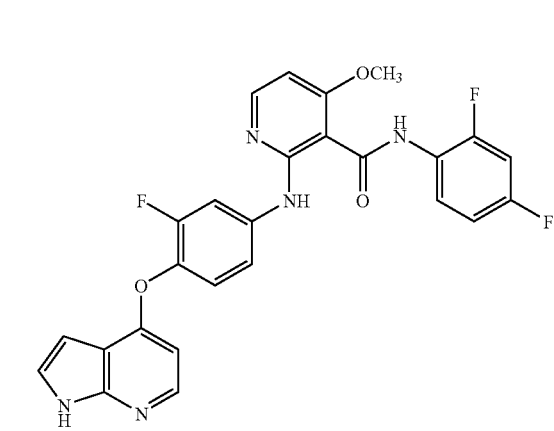

2-(4-(1H-Pyrrolo[2,3-b]pyridin-4-yloxy)-3-fluorophenylamino)-N-(2,4-difluorophenyl)-4-methoxynicotinamide, bis(triflouroacetic acid) salt and

Example 16

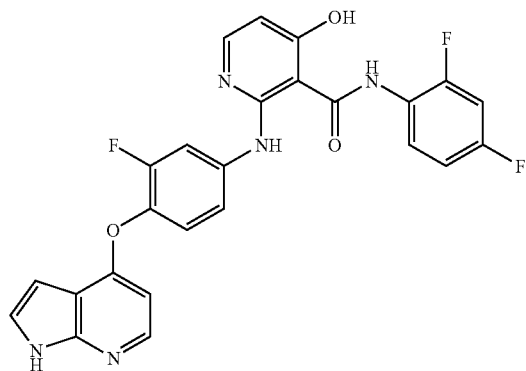

2-(4-(1H-Pyrrolo[2,3-b]pyridine-4-yloxy)-3-fluorophenylamino)-N-(2,4-difluorophenyl)-4-hydroxynicotinamide, bis(trifluoroacetic acid) salt

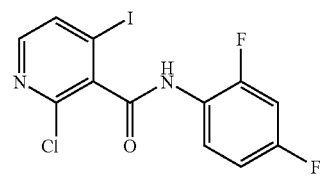

A) 2-Chloro-N-(2,4-difluorophenyl)-4-iodonicotinamide

To a homogeneous mixture of 2-chloro-4-iodonicotinic acid (CB Research & Development, Inc., 0.58 g, 2.0 mmol) and 2,4-difluoroaniline (Aldrich, 0.21 mL, 2.0 mmol) in anhydrous DMF (7 mL) was added PyBroP (Novabiochem, 1.4 g, 3.1 mmol) followed by DIPEA (1.1 mL, 6.6 mmol). The mixture was stirred for 63 hours, and then partitioned between chloroform and 10% LiCl (aq). After the aqueous layer was extracted with chloroform, the combined organic layers were washed twice with 10% LiCl (aq), dried over anhydrous MgSO$_4$, and then concentrated in vacuo. Purification of the residue by flash column chromatography (SiO$_2$, eluting with 1:1 hexane/EtOAc) afforded the desired compound (0.43 g, 53%). MS(ESI$^+$) m/z 395 (M+H)$^+$.

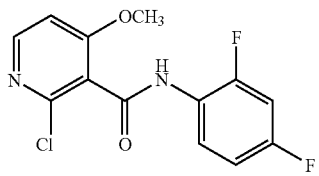

B) 2-Chloro-N-(2,4-difluorophenyl)-4-methoxynicotinamide

To a solution of sodium methoxide (0.023 g, 0.43 mmol) in anhydrous methanol (3 mL) was added 2-chloro-N-(2,4-difluorophenyl)-4-iodonicotinamide (0.17 g, 0.43 mmol). The mixture was heated at 60° C. for 12 hours then allowed to cool to ambient temperature. Concentration of the reaction mixture resulted in a residue that was triturated with methanol and water. Isolation by vacuum filtration afforded the desired compound (0.035 g) as an off-white solid. The filtrate was concentrated in vacuo to a residue that was purified by flash column chromatography (SiO$_2$, eluting with 25-100% EtOAc in hexane) to afford an additional amount desired compound (0.049 g, overall yield 65%) that was spectroscopically consistant with the initially isolated material. $^1$H NMR (DMSO-d$_6$) δ 10.48 (s, 1H), 8.38 (d, 1H, J=5.8 Hz), 7.85-7.96 (m, 1H), 7.33-7.40 (m, 1H), 7.27 (d, 1H, J=5.8 Hz), 7.05-7.20 (m, 1H), 3.92 (s, 3H); MS(ESI$^+$) m/z 299 (M+H)$^+$.

C) 2-(4-(1H-Pyrrolo[2,3-b]pyridin-4-yloxy)-3-fluorophenylamino)-N-(2,4-difluorophenyl)-4-methoxynicotinamide, bis(trifluoroacetic acid) salt (Example 16) and 2-(4-(1H-Pyrrolo[2,3-b]pyridine-4-yloxy)-3-fluorophenylamino)-N-(2,4-difluorophenyl)-4-hydroxynicotinamide, bis (trifluoroacetic acid) salt (Example 17)

To a homogeneous mixture of 4-(1H-pyrrolo[2,3-b]pyridin-4-yloxy)-3-fluorobenzenamine (0.037 g, 0.15 mmol, Compound C of Example 1) and 2-chloro-N-(2,4-difluorophenyl)-4-methoxynicotinamide (0.045 g, 0.15 mmol), in anhydrous NMP (0.50 mL), was added HCl (4N in 1,4-dioxane, 0.15 mL, 0.60 mmol). The mixture was microwaved in a CEM Explorer PLS microwave system (300 W), with the temperature measured with an IR temperature sensor and maintained at 140° C. for six hours. The reaction mixture was partitioned between water and EtOAc. The aqueous layer was extracted twice with EtOAc, and the combined organic layers were concentrated in vacuo. The resultant residue was purified by preparative (RP) HPLC (YMC S10 ODS, 30×500 mm, 30 minute gradient from 50% to 90% aqueous methanol with 0.1% TFA). The appropriate fractions were combined and concentrated in vacuo to afford 2-(4-(1H-pyrrolo[2,3-b]pyridin-4-yloxy)-3-fluorophenylamino)-N-(2,4-difluorophenyl)-4-methoxynicotinamide (Example 15) (0.006 g) as an off-white solid and 2-(4-(1H-pyrrolo[2,3-b]pyridine-4-yloxy)-3-fluorophenylamino)-N-(2,4-difluorophenyl)-4-hydroxynicotinamide (Example 16) (0.042 g) as a white solid.

Example 15

$^1$H NMR (DMSO-d$_6$) δ 13.42 (s, 1H), 12.10 (s, 1H), 11.12 (s, 1H), 8.54 (d, 1H, J=7.1 Hz), 8.23-8.35 (m, 1H), 7.80 (d, 1H, J=3.3 Hz), 7.55-7.75 (m, 2H), 7.25-7.41 (m, 3H), 6.89-7.10 (m, 2H), 6.77 (d, 1H, J=3.3 Hz), 6.00-6.09 (m, 1H), 4.23 (s, 3H);
HRMS(ESI$^+$), 506.1440 (M+H)$^+$ calc, 506.1438 (M+H)$^+$ found.

Example 16

$^1$H NMR (DMSO-d$_6$) δ 12.04 (s, 1H), 11.93 (s, 1H), 11.03 (s, 1H), 8.25-8.40 (m, 1H), 8.11 (d, 1H, J=5.6 Hz), 7.59 (dd, 1H, J=11.6, 1.9 Hz), 7.20-7.50 (m, 5H), 6.99-7.10 (m, 1H), 6.48 (d, 1H, J=5.6 Hz), 6.35 (dd, 1H, J=3.3, 1.9 Hz), 6.02 (d, 1H, J=7.4 Hz), 4.85 (br s, 1H); HRMS(ESI$^+$), 492.1283 (M+H)$^+$ calc, 492.1282 (M+H)$^+$ found.

Example 17

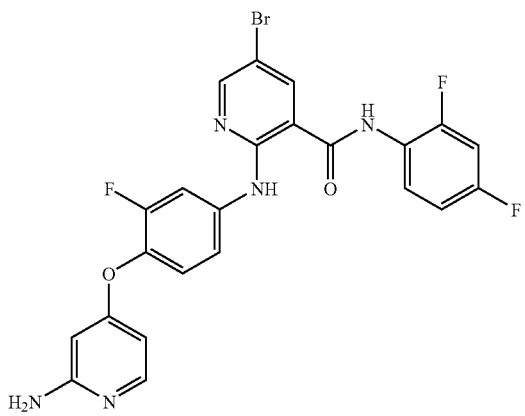

2-(4-(2-Aminopyridin-4-yloxy)-3-fluorophenylamino)-5-bromo-N-(2,4-difluorophenyl)nicotinamide, bis(trifluoroacetic acid) salt

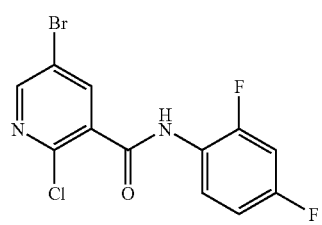

A) 5-Bromo-2-chloro-N-(2,4-difluorophenyl)nicotinamide

To a suspension of 5-bromo-2-hydroxynicotinic acid (2.20 g, 10 mmol *Synthesis*, 2002, 528-532) in 10 mL of SOCl$_2$ at room temperature was added slowly 1 mL of DMF and the resulting solution was then heated at 80° C. for 2 h. The excess SOCl$_2$ was removed under reduced pressure. The residue dissolved in 50 mL of dichloromethane (DCM). To the mixture was added 2,4-di-fluoroaniline (1.29 g, 10 mmol), followed by the addition of 4 mL of triethylamine. The reaction mixture was stirred at room temperature for 1 h and then diluted with 20 mL of H$_2$O. The two layers were separated and the aqueous layer extracted with EtOAc. The combined organic layers were washed with brine and dried over MgSO$_4$. After filtration and concentration, the residue was triturated with DCM and filtered and washed with DCM to provide the desired compound (1.40 g, 40% yield). MS (ESI$^+$) m/z 347.13, 349.12, 351.09 (M+H)$^+$.

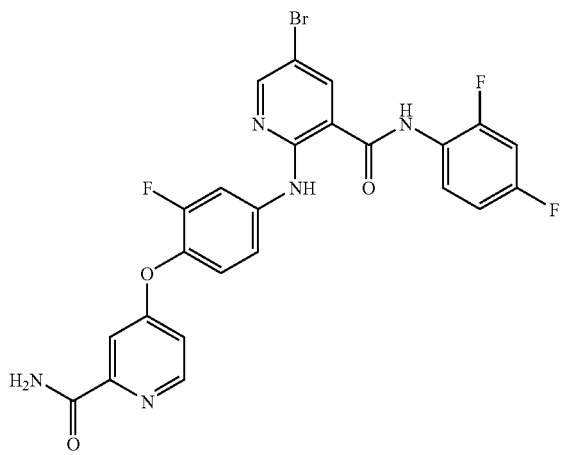

B) 4-(4-(5-Bromo-3-(2,4-difluorophenylcarbamoyl)pyridin-2-ylamino)-2-fluorophenoxy)picolinamide To a solution of 5-bromo-2-chloro-N-(2,4-difluorophenyl)nicotinamide (126 mg, 0.51 mmol) and 4-(4-amino-2-fluorophenoxy)picolinamide (172 mg, 0.49 mmol, Compound C of Example 3) in 3 mL of NMP was added toluenesulfonic acid monohydrate (71 mg, 0.37 mmol). The mixture was stirred at 120° C. for 2 h and at 160° C. for 15 h. The solution was cooled to rt and purified on preparative (RP) HPLC. The fractions containing the desired product pooled and concentrated in vacuo. The residue was then partitioned between 1N NaOH and EtOAc and the two layers were separated. The organic layer washed with brine and dried over MgSO$_4$. After filtration and concentration, the desired product was obtained (30 mg, 11% yield). MS (ESI$^+$) m/z 558.22, 560.22 (M+H)$^+$.

C) 2-(4-(2-Aminopyridin-4-yloxy)-3-fluorophenylamino)-5-bromo-N-(2,4-difluorophenyl)nicotinamide, bis(trifluoroacetic acid) salt To a solution of 4-(4-(5-bromo-3-(2,4-difluorophenylcarbamoyl)pyridin-2-ylamino)-2-fluorophenoxy)picolinamide (28 mg, 0.05 mmol) in 1 mL of DMF were added H$_2$O (50 mg, 2.7 mmol), pyridine (100 mg, 1.2 mmol) and PhI(OCOCF$_3$)$_2$ (26 mg, 0.06 mmol). The mixture was stirred for 30 min and then another equivalent of PhI(OCOCF$_3$)$_2$ (26 mg, 0.06 mmol) was added. The stirring was continued for 1 h and the reaction was then purified on preparative (RP) HPLC. The fraction containing the desired product was pooled and concentrated in vacuo to give the title compound (5 mg, 13% yield) as a bis(trifluoroacetic acid) salt. $^1$H NMR (DMSO-d$_6$) δ 10.59 (s, 1H), 10.52 (s, 1H), 8.49 (s, 2H), 8.02 (d, 1H, J=13.4 Hz), 7.89 (d, 1H, J=7.1 Hz), 7.31-7.56 (m, 4H), 7.12 (m, 1H), 6.64 (d, 1H, J=7.1 Hz), 6.09 (s, 1H); MS (ESI$^+$) m/z 530.17, 532.17 (M+H)$^+$.

Example 18

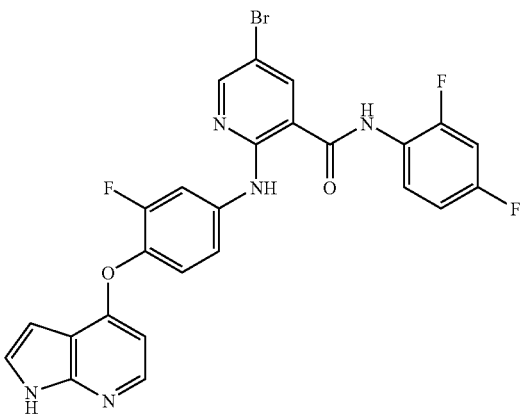

2-(4-(1H-Pyrrolo[2,3-b]pyridin-4-yloxy)-3-fluorophenylamino)-5-bromo-N-(2,4-difluorophenyl)nicotinamide, dihydrochloride salt

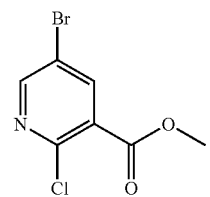

A) Methyl 5-bromo-2-chloronicotinate

To a suspension of 5-bromo-2-hydroxynicotinic acid (4.34 g, 20 mmol) in 20 mL of SOCl$_2$ at room temperature was added 1 mL of DMF slowly. The solution was then heated at 80° C. for 2 h. The solvent was removed under reduced pressure and the residue was dissolved in 50 mL of DCM. To the mixture was added 10 mL of MeOH and the stirring continued for 1 h. The solution was concentrated in vacuo and the residue was dissolved in 200 mL of EtOAc. The mixture was then washed with brine and dried over MgSO$_4$. After filtration and concentration in vacuo, the desired product (5.0 g, >95% yield) was obtained. MS (ESI) m/z 250.04, 252.05, 254.05 (M+H)$^+$.

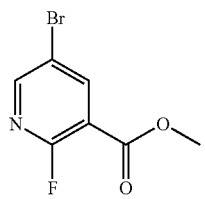

B) Methyl 5-bromo-2-fluoronicotinate

To a solution of methyl 5-bromo-2-chloronicotinate (170 mg, 0.68 mmol) in 3 mL of DMSO was added CsF (152 mg, 1.0 mmol). The solution was stirred at room temperature for 2 d and then heated at 60° C. for 4 h. After cooling, the mixture was diluted with 30 mL of H$_2$O. The aqueous solution was extracted with EtOAc and the combined organic layers were washed with brine, and dried over MgSO$_4$. After filtration and concentration in vacuo, the residue was purified by silica gel flash chromatography to give the desired product (90 mg, 57% yield). MS (ESI$^+$) m/z 234.06, 236.09 (M+H)$^+$.

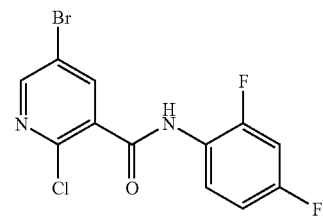

C) 5-Bromo-N-(2,4-difluorophenyl)-2-fluoronicotinamide

To a solution of methyl 5-bromo-2-fluoronicotinate (90 mg, 0.38 mmol) in 2 mL of THF was added 1N NaOH (1.0 mL, 1.0 mmol) at room temperature. The reaction was stirred at room temperature for 2 h before it was neutralized by 1.0 mL of 1N HCl. The solution was then concentrated under reduced pressure and the residue was purified on preparative (RP) HPLC to provide 5-Bromo-2-fluoronicotinic acid (55 mg).

To a solution of 5-bromo-2-fluoronicotinic acid (55 mg, 0.25 mmol) in a mixture of 2.0 mL of THF and 5.0 mL of DCM was added (COCl)$_2$ (0.13 mL, 1.5 mmol). The mixture was stirred at room temperature for 1 h and at 40° C. overnight. After cooling, the solvent was removed under reduced pressure. The residue was dissolved in 2.0 mL of DCM and to it were added 2,4-difluoroaniline (0.05 mL, 0.5 mmol) and 0.1 mL of TEA. The mixture was stirred at room temperature for 2 h and diluted with H$_2$O. The organic layer was separated and the aqueous layer was extracted with EtOAc. The combined organic layers were washed with brine and dried over MgSO$_4$. After filtration and concentration in vacuo, the residue was purified on preparative (RP) HPLC to give the desired product (60 mg, 73% yield). MS(ESI$^+$) m/z 331.18, 333.18 (M+H)$^+$.

D) 2-(4-(1H-Pyrrolo[2,3-b]pyridin-4-yloxy)-3-fluorophenylamino)-5-bromo-N-(2,4-difluorophenyl) nicotinamide, dihydrochloride salt To a solution of 4-(1H-pyrrolo[2,3-b]pyridin-4-yloxy)-3-fluoroaniline (17 mg, 0.07 mmol, Compound C of Example 1) and 5-bromo-N-(2,4-difluorophenyl)-2-fluoronicotinamide (26 mg, 0.08 mmol) in 1 mL of NMP was added 4N HCl in 1,4-dioxane (0.05 mL, 0.20 mmol). The mixture was stirred at 110° C. for 4 d. After cooling, the mixture was purified on preparative (RP) HPLC to give fractions containing the desired product. The fractions were pooled and concentrated in vacuo and the residue was treated with 10 mL of 1N HCl and it was concentrated again to give the title compound (8.0 mg, 18% yield). $^1$H NMR (DMSO-d$_6$) δ 10.66 (s, 1H), 10.62 (s, 1H), 8.55 (d, 2H, J=7.5 Hz), 8.06 (d, 1H, J=13.4 Hz), 7.35-7.62 (m, 5H), 7.16 (m, 1H), 6.62 (d, 1H, J=6.0 Hz), 6.43 (s, 1H); MS(ESI$^+$) m/z 554.15, 556.14 (M+H)$^+$.

Example 19

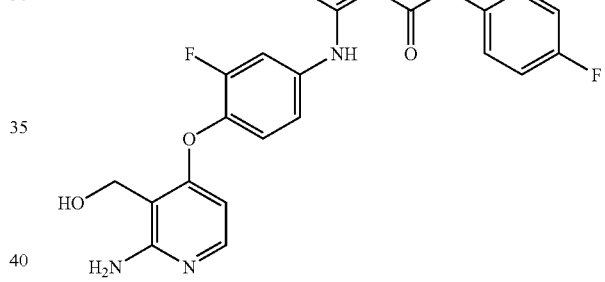

2-(4-(2-Amino-3-(hydroxymethyl)pyridin-4-yl oxy)-3-fluorophenyl amino)-N-(2,4-difluorophenyl)nicotinamide, dihydrochloride salt

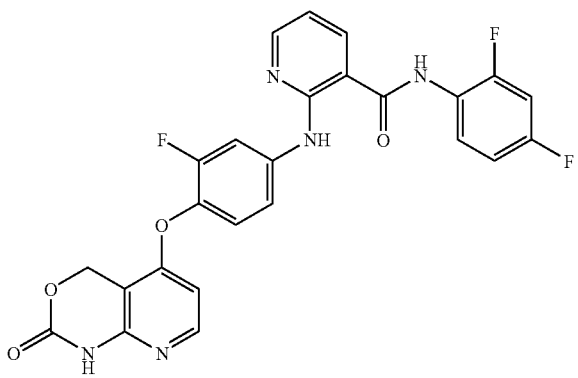

A) N-(2,4-Difluorophenyl)-2-(3-fluoro-4-(2-oxo-2,4-dihydro-1H-pyrido[2,3-d][1,3]oxazin-5-yloxy)phenylamino)nicotinamide, trifluoroacetic acid salt To a solution of N-(2,4-difluorophenyl)-2-fluoronicotinamide (25 mg, 0.1 mmol, Compound C of Example 1) and tert-butyl 4-(4-amino-2-fluorophenoxy)-3-((tert-butyldimethylsilyloxy)methyl)pyridin-2-ylcarbamate (46 mg, 0.1 mmol, Compound B of Example 129 in US 2005/0245530) in 1 mL of NMP was added 4N HCl in 1,4-dioxane (0.025 mL, 0.1 mmol). The reaction mixture was stirred at 110° C. overnight and 120° C. for 3 d. To the mixture was then added 4N HCl (0.05 mL, 0.2 mmol) and it was heated at 140° C. overnight. After cooling, the mixture was purified on preparative (RP) HPLC to provide the desired product (10 mg, 16% yield).

MS(ESI$^+$) m/z 508.12 (M+H)$^+$.

B) 2-(4-(2-Amino-3-(hydroxymethyl)pyridin-4-yloxy)-3-fluorophenylamino)-N-(2,4-difluorophenyl)nicotinamide, dihydrochloride salt To a solution of N-(2,4-difluorophenyl)-2-(3-fluoro-4-(2-oxo-2,4-dihydro-1H-pyrido[2,3-d][1,3]oxazin-5-yloxy)phenylamino)nicotinamide, trifluoroacetic acid (10 mg, 0.016 mmol) in 1 mL of THF was added 1N NaOH (0.5 mL, 0.5 mmol). The mixture was stirred at room temperature for 1 h and then at 50° C. overnight. After cooling, the mixture was purified by preparative (RP) HPLC to give the fractions containing the desired product. The fractions were pooled and concentrated in vacuo and the residue was treated with excess of 1N HCl and concentrated again to provide the title compound (7 mg, 79% yield). $^1$H NMR (DMSO-d$_6$) δ 10.77 (s, 1H), 10.56 (s, 1H), 8.44 (d, 1H, J=6.3 Hz), 8.39 (d, 1H, J=7.5 Hz), 8.16 (d, 1H, J=13.0 Hz), 7.89-7.92 (m, 3H), 7.28-7.58 (m, 4H), 7.15 (m, 1H), 7.03 (m, 1H), 6.24 (d, 1H, J=7.0 Hz), 4.64 (s, 2H); MS(ESI$^+$) m/z 482.16 (M+H)$^+$.

Example 20

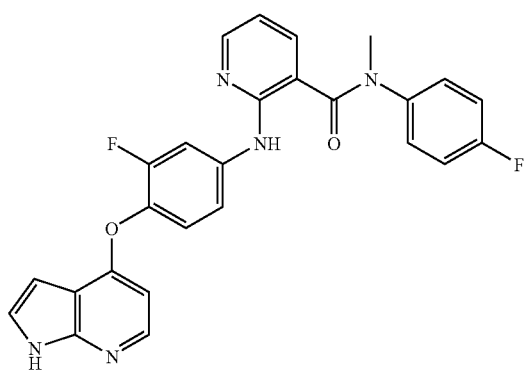

2-(4-(1H-Pyrrolo[2,3-b]pyridin-4-yloxy)-3-fluorophenylamino)-N-(4-fluorophenyl)-N-methylnicotinamide, dihydrochloride salt

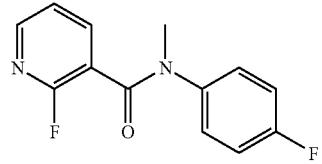

A) 2-Fluoro-N-(4-fluorophenyl)-N-methylnicotinamide

To a suspension of 2-fluoronicotinic acid (820 mg, 5.83 mmol) and oxalyl chloride (1.27 g, 10 mmol) in CH$_2$Cl$_2$ (10 mL) at RT, was added 2 drops of DMF. The resulting mixture was stirred for 3 h. The solvent was removed in vacuo to afford 2-fluoronictinoyl chloride (920 mg).

To a solution of 4-fluoro-N-methylaniline (75 mg, 0.6 mmol) and DIPEA (90 mg, 0.7 mmol) in THF (2 mL) at room temperature, was added a solution of 2-fluoronictinoyl chloride (80 mg, 0.5 mmol) in CH$_2$Cl$_2$ (2 mL). The mixture was stirred overnight. The mixture was diluted with CH$_2$Cl$_2$, washed with 5% aq. citric acid solution, and sat. aq. K$_2$HPO$_4$ solution, and dried over MgSO$_4$. The product was purified by flash column chromatography (silica gel, eluding with a gradient of CH$_2$Cl$_2$/EtOAc) to give the desired product as a light yellow solid (120 mg, 97% yield). MS(ESI$^+$) m/z 249 (M+H)$^+$.

B) 2-(4-(1H-Pyrrolo[2,3-b]pyridin-4-yloxy)-3-fluorophenylamino)-N-(4-fluorophenyl)-N-methylnicotinamide, dihydrochloride salt A mixture of 2-fluoro-N-(4-fluorophenyl)-N-methylnicotinamide (50 mg, 0.2 mmol) and 4-(1H-pyrrolo[2,3-b]pyridin-4-yloxy)-3-fluoroaniline (122 mg, 0.5 mmol, Compound C of Example 1) in DMA (0.8 mL) was heated in a microwave at 160° C. for 20 min. The product was purified by preparative (RP) HPLC to afford the title compound as a beige solid (11 mg, 11% yield)—dihydrochloride salt. $^1$H NMR (CD$_3$OD) δ 8.56 (d, 1H, J=3.5 Hz), 8.23 (dd, 1H, J=7.6, 1.0 Hz), 8.19 (d, 1H, J=7.1 Hz), 7.58 (m, 3H), 7.32 (dd, 1H, J=11.2, 2.5 Hz), 7.22 (d, 1H, J=8.6 Hz), 7.04 (d, 1H, J=4.1 Hz), 6.96 (d, 1H, J=7.9 Hz), 6.47 (m, 4H), 3.27 (s. 3H). MS(ESI$^+$) m/z 472 (M+H)$^+$.

Example 21

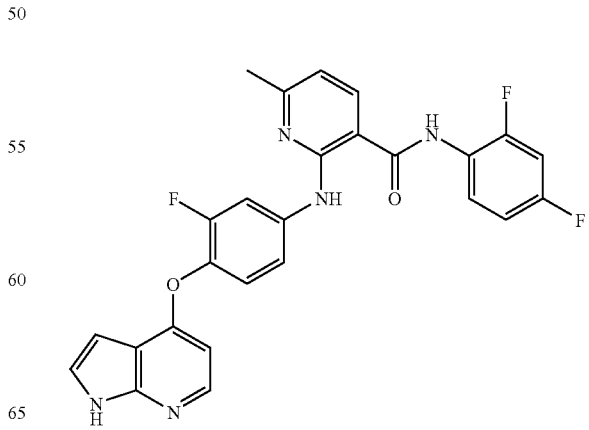

2-(4-(1H-Pyrrolo[2,3-b]pyridin-4-yloxy)-3-fluorophenylamino)-N-(2,4-difluorophenyl)-6-methylnicotinamide, dihydrochloride salt

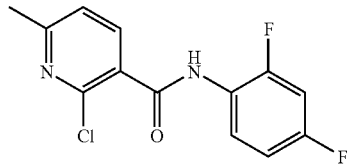

A) 2-Chloro-N-(2,4-difluorophenyl)-6-methylnicotinamide

2-Chloro-6-methylnicotinic acid (500 mg, 2.9 mmol) was suspended in $CH_2Cl_2$ (14.6 mL). Oxalyl chloride (0.3 mL, 3.5 mmol) was added followed by 3 drops of DMF and the reaction was stirred at 23° C. for 2 h. The solvent was removed by rotary evaporation and the residue was dried under vacuum. The crude acid chloride was dissolved in $CH_3CN$ (14 mL) and 2,4-difluorobenzenamine (0.33 mL, 3.2 mmol) was added followed by triethylamine (0.41 mL, 2.9 mmol). The reaction was stirred at 23° C. for 16 h and then concentrated in vacuo. The residue was partitioned between EtOAc (30 mL) and sat. aq. $NaHCO_3$ soln (30 mL). A little water was added to help break up some of the residual salts. The aqueous layer was extracted with EtOAc (3×30 mL). The combined organics were dried over $MgSO_4$ and concentrated in vacuo. Trituration with hot 5% EtOAc-hexanes afforded the desired product as a light tan powder (559 mg, 68%). $^1$H NMR (400 MHz, $CDCl_3$) δ 2.60 (s, 3H), 6.82-7.09 (m, 2H), 7.22-7.32 (d, 1H, J=7.63 Hz), 8.18 (d, 1H, J=8.14 Hz), 8.28-8.50 (m, 1H), 8.57 (s, 1H).

B) 2-(4-(1H-Pyrrolo[2,3-b]pyridin-4-yloxy)-3-fluorophenylamino)-N-(2,4-difluorophenyl)-6-methylnicotinamide, dihydrochloride salt 4-(1H-Pyrrolo[2,3-b]pyridin-4-yloxy)-3-fluorobenzenamine (40 mg, 164 μmol, Compound C of Example 1) and 2-chloro-N-(2,4-difluorophenyl)-6-methylnicotinamide (51 mg, 181 μmol) were suspended in 1,4-dioxane (1 mL). 4M HCl in 1,4-dioxane (0.16 mL, 0.333 mmol) was added and the reaction was irradiated (CEM personal microwave, 300 W) to a temperature of 160° C. for 60 min. The reaction was cooled to ambient temperature and NMP (1 mL) was added. The reaction mixture was re-heated to 160° C. (microwave irradiation, 300 W) for an additional two hours. The 1,4-dioxane was removed by rotary evaporation and the residue was partitioned between 10% aq. $NaHCO_3$ solution (10 mL) and EtOAc (10 mL). The organic layer was separated and the aqueous layer was extracted EtOAc (2×10 mL). The combined organic layers were washed with 10% LiCl (20 mL), dried ($Na_2SO_4$) and concentrated in vacuo. The crude product was purified by preparative (RP) HPLC Chromatography (YMC S5 ODS, 20×100 mm, 10 minute gradient from 33% to 90% aqueous methanol with 0.1% TFA). The fractions containing the desired product were combined and concentrated. The purified material was dissolved in MeOH (1 mL), acidified with 4 N HCl in 1,4-dioxane (0.10 mL) and concentrated. The resulting salt was triturated with hot EtOAc and collected by filtration to afford a brown solid (4.4 mg, >97% HPLC purity). $^1$H NMR (DMSO-$d_6$) δ 3.15 (s, 3H), 6.48 (s, 1H), 6.69 (d, 1H, J=6.10 Hz), 6.91 (d, 1H, J=7.63 Hz), 7.06-7.21 (m, 1H), 7.31-7.44 (m, 2H), 7.46-7.64 (m, 3H), 8.12-8.42 (m, 3H), 10.41 (s, 1H), 10.96 (s, 1H), 12.58 (s, 1H); MS(ESI$^+$) m/z 490.2 (M+H)$^+$.

Example 22

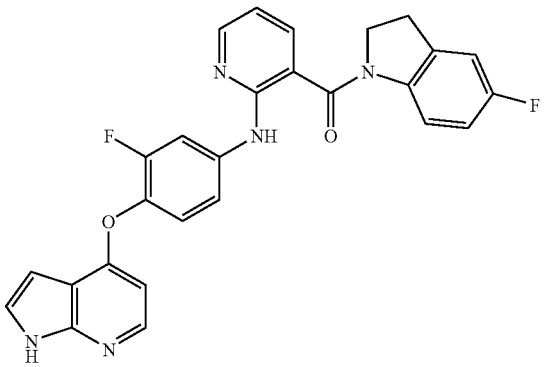

2-(4-(1H-Pyrrolo[2,3-b]pyridin-4-yloxy)-3-fluorophenylamino)pyridin-3-yl)(5-fluoroindolin-1-yl)methanone, dihydrochloride salt

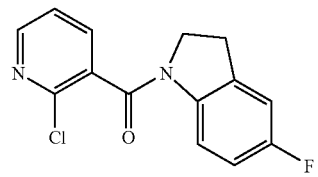

A) (2-Chloropyridin-3-yl)-(5-fluoroindolin-1-yl)methanone

2-Chloronicotinoyl chloride (200 mg, 1.14 mmol) was dissolved in $CH_3CN$ (5.6 mL). 5-Fluoroindoline (171 mg, 1.25 mmol) was added followed by triethylamine (0.24 mL, 1.71 mmol) and the reaction mixture was stirred at 23° C. for 16 h. The solvent was removed by evaporation and the residue was partitioned between $CH_2Cl_2$ (10 mL) and sat. aq. $NaHCO_3$ solution (10 mL). The organic phase was removed and the aqueous phase was extracted with $CH_2Cl_2$ (2×10 mL). The combined organics were dried over $Na_2SO_4$ and concentrated in vacuo. Flash column chromatography (40 g $SiO_2$, 2% $CH_3OH$—$CH_2Cl_2$) afforded the desired product as an off-white solid (247.8 mg, 79%). $^1$H NMR (DMSO-$d_6$) δ 3.14 (t, 2H, J=8.39 Hz), 3.82 (t, 2H, J=8.39 Hz), 7.09 (dt, 1H, J=9.03, 2.80 Hz,), 7.20 (dd, 1H, J=8.39, 2.80 Hz), 7.60 (dd, 1H, J=7.38, 4.83 Hz), 8.10 (dd, 1H, J=7.63, 2.03 Hz), 8.15 (dd, 1H, J=8.90, 4.83 Hz), 8.55 (dd, 1H, J=4.83, 1.78 Hz).

B) 2-(4-(1H-Pyrrolo[2,3-b]pyridin-4-yloxy)-3-fluorophenylamino)pyridin-3-yl)(5-fluoroindolin-1-yl)methanone, dihydrochloride salt 4-(1H-Pyrrolo[2,3-b]pyridin-4-yloxy)-3-fluorobenzenamine (40 mg, 0.16 mmol, Compound C of Example 1) and (2-chloropyridin-3-yl)(5-fluoroindolin-1-yl)methanone (46 mg, 0.16 mmol) were suspended in isopropanol (1.6 mL). 4N HCl in 1,4-dioxane (0.16 mL, 0.64 mmol) was added and the reaction was heated to 80° C. for 72 h. NMP (1 mL) was added and the reaction mixture was heated to 100° C. until no further conversion to product was observed. The isopropanol was removed by rotary evaporation and the resulting residue was partitioned between 10% aq. LiCl solution (10 mL) and EtOAc (10 mL). The organic layer was separated and the aqueous layer was extracted EtOAc (2×10 mL). The combined organic layers were washed with 10% LiCl (20 mL), dried ($Na_2SO_4$) and concentrated. The crude product was purified by preparative (RP) HPLC chromatography (YMC S5 ODS, 30×75 mm, 10 minute gradient from 33% to 90% aqueous methanol with 0.1% TFA, 40 mL/min). The fractions containing the desired product were combined and concentrated. The purified material was dissolved in MeOH (1 mL) and acidified with 4 N HCl-1,4-dioxane (0.10 mL). The resulting salt was triturated with hot EtOAc-$Et_2O$ and collected by filtration to afford a tan powder (2.7 mg, >95% HPLC purity). $^1$H NMR (DMSO-$d_6$) δ 3.10 (t, 2H, J=8.11 Hz), 3.42-3.53 (m, 1H), 3.61-3.75 (m, 1H), 6.38 (d, 1H, J=1.37 Hz), 6.53 (d, 1H, J=5.77 Hz), 6.99 (dd, 1H, J=7.42, 4.95 Hz), 7.04 (s, 1H), 7.17 (dd, 1H, J=8.25, 2.47 Hz), 7.32 (t, 1H, J=9.21 Hz), 7.44 (d, 1H, J=9.90 Hz), 7.46-7.51 (m, 1H), 7.85 (d, 1H, J=6.60 Hz), 7.90 (d, 1H, J=12.92 Hz), 8.19 (d, 1H, J=6.05 Hz), 8.34 (dd, 1H, J=4.95, 1.65 Hz), 8.92 (s, 1H), 12.23 (s, 1H);

MS(ESI$^+$) m/z 484.3 (M+H)$^+$.

Example 23

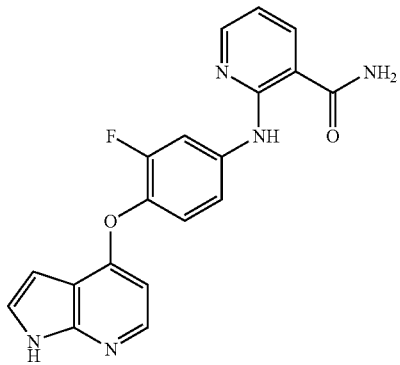

2-(4-(1H-Pyrrolo[2,3-b]pyridin-4-yloxy)-3-fluorophenylamino)nicotinamide, bis(trifluoroacetic acid) salt 4-(1H-Pyrrolo[2,3-b]pyridin-4-yloxy)-3-fluorobenzenamine (40 mg, 0.16 mmol, Compound C of Example 1) and 2-chloronicotinamide (26 mg, 0.16 mmol) were suspended in isopropanol (1.6 mL). 4N HCl in 1,4-dioxane (0.16 mL, 0.33 mmol) was added and the reaction was heated to 80° C. for 72 h. NMP (1 mL) was added and the reaction mixture was heated to 100° C. for 48 h. The isopropanol was removed by rotary evaporation and the resulting residue was partitioned between 5% aq. $NaHCO_3$ solution (10 mL) and EtOAc (10 mL). The organic layer was separated and the aqueous layer was extracted EtOAc (2×10 mL). The combined organic layers were washed with 10% LiCl (20 mL), dried ($MgSO_4$) and concentrated. The crude product was purified by preparative (RP) HPLC chromatography (YMC S5 ODS, 30×75 mm, 10 minute gradient from 33% to 90% aqueous methanol with 0.1% TFA, 40 mL/min). The fractions containing the desired product were combined and concentrated. The purified material was triturated with 10:1 $Et_2O$-MeOH (3 mL) to afford the desired product as a cream solid (21.0 mg, >99% HPLC purity). $^1$H NMR (DMSO-$d_6$) δ 6.32 (dd, 1H, J=3.05, 1.53 Hz), 6.46 (d, 1H, J=5.60 Hz), 6.92 (dd, 1H, J=7.88, 4.83 Hz), 7.30-7.40 (m, 2H), 7.42 (t, 1H), 7.79 (s, 1H), 8.12 (d, 1H, J=5.59 Hz), 8.17 (dd, 1H, J=23.65, 1.78 Hz), 8.16-8.19 (m, 1H, J=1.53 Hz), 8.32-8.39 (m, 2H), 11.45 (s, 1H), 11.96 (s, 1H); MS(ESI$^+$) m/z 364.3 (M+H)$^+$.

Example 24

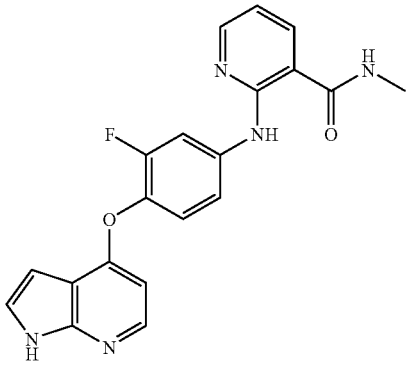

2-(4-(1H-Pyrrolo[2,3-b]pyridin-4-yloxy)-3-fluorophenylamino)-N-methylnicotinamide, dihydrochloride salt

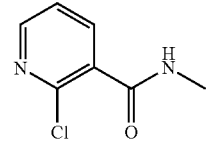

A) 2-Chloro-N-methylnicotinamide

Methanamine (0.425 mL, 3.41 mmol) and triethylamine (0.792 mL, 5.68 mmol) were dissolved in $CH_3CN$ (14.2 mL) at 23° C. 2-Chloronicotinoyl chloride (500 mg, 2.84 mmol) was added and the reaction mixture was stirred at 23° C. for 16 h. The solvent was removed by rotary evaporation and the residue was partitioned between EtOAc (20 mL) and sat. aq. $NaHCO_3$ (20 mL). The aqueous phase was extracted with EtOAc (3×20 mL). The combined organic phases were dried over $MgSO_4$ and concentrated. Trituration of the resulting solid with 5% EtOAc-hexane provided the desired product as a white powder (153.2 mg, 31%). $^1$H NMR (CD$_3$OD) δ 8.43 (dd, 1H, J=5.09, 2.03 Hz), 7.88 (dd, 1H, J=7.63, 2.03 Hz), 7.45 (dd, 1H, J=7.38, 4.83 Hz), 2.91 (s, 3H); MS(ESI$^+$) m/z 171.1 (M+H)$^+$.

B) 2-(4-(1H-Pyrrolo[2,3-b]pyridin-4-yloxy)-3-fluorophenylamino)-N-methylnicotinamide, dihydrochloride salt 4-(1H-Pyrrolo[2,3'-b]pyridin-4-yloxy)-3-fluorobenzenamine (75 mg, 0.31 mmol) and 2-chloro-N-methylnicotinamide (53 mg, 0.31 mmol) were suspended in 3:1 isopropanol-NMP (3.0 mL). 4N HCl in 1,4-dioxane 0.23 mL, 0.93 mmol) was added and the reaction was heated to 100° C. for 24 h. The isopropanol was removed by rotary evaporation and the resulting residue was partitioned between 5% aq. NaHCO$_3$ solution (10 mL) and EtOAc (10 mL). The organic layer was separated and the aqueous layer was extracted EtOAc (3×10 mL). The combined organic layers were washed with 10% LiCl (20 mL), dried (MgSO$_4$) and concentrated. The crude product was purified by preparative (RP) HPLC chromatography (YMC S5 ODS, 30×75 mm, 10 minute gradient from 33% to 90% aqueous methanol with 0.1% TFA, 40 mL/min). The fractions containing the desired product were combined and concentrated. The product residue was dissolved in MeOH (2 mL) and acidified with 4N HCl in 1,4-dioxane (0.10 mL). After concentration the product was triturated with 5% EtOAc-hexane (3 mL) to afford the desired product as a tan solid (16.4 mg, >99% HPLC purity). $^1$H NMR (CD$_3$OD) δ 8.44 (d, 1H, J=6.10 Hz), 8.37 (d, 1H, J=7.12 Hz), 8.13 (d, 1H, J=6.10 Hz), 7.78 (dd, 1H, J=11.70, 2.03 Hz), 7.58-7.69 (m, 2H), 7.48 (d, 1H, J=8.14 Hz), 7.09-7.21 (m, 1H), 7.05 (d, 1H, J=7.12 Hz), 6.83 (d, 1H, J=3.56 Hz), 3.34 (s, 1H), 2.97 (s, 1H); MS(ESI$^+$) m/z 378.3 (M+H)$^+$.

Example 25

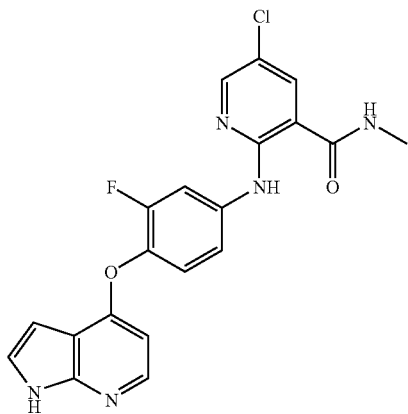

2-(4-(1H-Pyrrolo[2,3-b]pyridin-4-yloxy)-3-fluorophenylamino)-5-chloro-N-methylnicotinamide, dihydrochloride salt

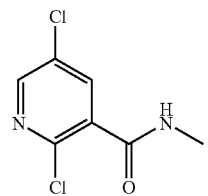

A) 2,5-Dichloro-N-methylnicotinamide

Methanamine (0.355 mL, 2.85 mmol) and triethylamine (0.662 mL, 4.75 mmol) were dissolved in CH$_3$CN (14.2 mL) at 23° C. 2,5-Dichloronicotinoyl chloride (500 mg, 2.376 mmol) was added and the reaction was stirred for 16 h. The solvent was removed by rotary evaporation and the residue was partitioned between EtOAc (20 mL) and 5% aq. NaHCO$_3$ soln. (20 mL). The aqueous phase was extracted with EtOAc (3×20 mL). The combined organics were washed with brine, dried over MgSO$_4$ and concentrated. The resulting solid was triturated in 5% EtOAc-Hexane to provide the desired product as a cream powder (456.7 mg, 94%). $^1$H NMR (CD$_3$OD) δ 8.46 (d, 1H, J=2.54 Hz), 7.96 (d, 1H, J=2.54 Hz), 2.90 (s, 3H); MS(ESI$^+$) m/z 205.1 (M+H)$^+$.

B) 2-(4-(1H-Pyrrolo[2,3-b]pyridin-4-yloxy)-3-fluorophenylamino)-5-chloro-N-methylnicotinamide, dihydrochloride salt 4-(1H-Pyrrolo[2,3-b]pyridin-4-yloxy)-3-fluorobenzenamine (70 mg, 0.29 mmol, Compound C of Example 1) and 2-chloro-N-methylnicotinamide (59 mg, 0.29 mmol) were suspended in 3:1 isopropanol-NMP (2.9 mL). 4N HCl in 1,4-dioxane (0.22 mL, 0.86 mmol) was added and the reaction was heated to 100° C. for 168 h. The reaction was diluted with 30 mL of H$_2$O and then basified with sat. aq. NaHCO$_3$ soln. (5 mL). The aqueous layer was extracted EtOAc (3×10 mL). The combined organic layers were washed with 10% LiCl (15 mL), dried (MgSO$_4$) and concentrated. The crude product was purified by preparative (RP) HPLC chromatography (YMC S5 ODS, 30×75 mm, 10 minute gradient from 33% to 90% aqueous methanol with 0.1% TFA, 40 mL/min). The fractions containing the desired product were combined and concentrated. The product residue was dissolved in MeOH (2 mL) and acidified with 4N HCl in 1,4-dioxane (0.10 mL). Concentration afford the desired product as a brown solid (3.3 mg, >99% HPLC purity). $^1$H NMR (CD$_3$OD) δ 8.33 (d, 1H, J=2.54 Hz), 8.31 (d, 1H, J=7.12 Hz), 8.17 (dd, 1H, J=13.48, 2.29 Hz), 8.09 (d, 1H, J=2.03 Hz), 7.56 (d, 1H, J=3.56 Hz), 7.33-7.43 (m, 2H), 6.91 (d, 1H, J=6.61 Hz), 6.68 (d, 1H, J=3.56 Hz), 2.93 (s, 3H); MS(ESI$^+$) m/z 412.2 (M+H)$^+$.

Example 26

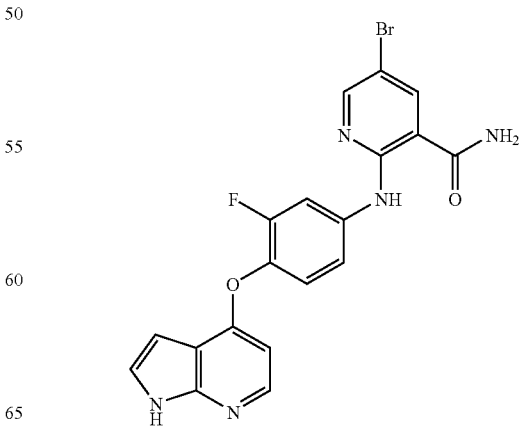

2-(4-(1H-Pyrrolo[2,3-b]pyridin-4-yloxy)-3-fluorophenylamino)nicotinamide, bis(trifluoroacetic acid) salt

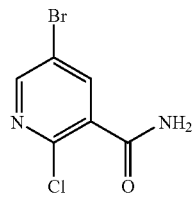

A) 5-Bromo-2-chloronicotinamide

Sodium 5-bromo-2-chloronicotinate (229 mg, 0.798 mmol) was suspended in $CH_2Cl_2$ (7.9 mL). Oxalyl chloride (0.084 ml, 0.957 mmol) was added followed by DMF (0.002 mL, 0.080 mmol) and the reaction mixture was stirred at 23° C. for 1 h. The solvent was removed by evaporation and the intermediate residue was dried under vacuum for 90 minutes. The crude acid chloride was suspended in $CH_3CN$ (7.9 mL) and $NH_3$ (7M in MeOH, 0.125 mL, 0.877 mmol) was added and the reaction mixture was stirred at ambient temperature for 16 h. The solvent was removed by evaporation and the residue was partitioned between EtOAc (20 mL) and $H_2O$ (20 mL). The EtOAc layer was removed and the aqueous layer was extracted with EtOAc (3×25 mL). The combined organics were washed with brine, dried over $MgSO_4$ and concentrated. The resulting solid was triturated with cold $CH_2Cl_2$ to provide the desired product as a tan powder (80.5 mg, 43%). $^1H$ NMR ($CDCl_3$) δ 6.08 (s, 1H), 6.66 (s, 1H), 8.36 (d, 1H, J=2.54 Hz), 8.54 (d, 1H, J=2.54 Hz).

B) 2-(4-(1H-Pyrrolo[2,3-b]pyridin-4-yloxy)-3-fluorophenylamino)nicotinamide, bis(trifluoroacetic acid) salt 4-(1H-Pyrrolo[2,3-b]pyridin-4-yloxy)-3-fluorobenzenamine (51.7 mg, 0.21 mmol) and 5-bromo-2-chloronicotinamide (50 mg, 0.21 mmol) were suspended in 3:1 isopropanol-NMP (2.1 mL). 4N HCl in 1,4-dioxane (0.21 mL, 0.84 mmol) was added and the reaction was heated to 100° C. for 240 h. The isopropanol was removed by rotary evaporation and the resulting residue was partitioned between 5% aq. $NaHCO_3$ solution (10 mL) and EtOAc (10 mL). The organic layer was separated and the aqueous layer was extracted EtOAc (2×10 mL). The combined organic layers were washed with 10% LiCl (20 mL), dried ($MgSO_4$) and concentrated. The crude product was purified by preparative (RP) HPLC chromatography (YMC S5 ODS, 30×75 mm, 10 minute gradient from 33% to 90% aqueous methanol with 0.1% TFA, 40 mL/min). The fractions containing the desired product were combined and concentrated to afford the desired product as a tan powder (10.1 mg, >98% HPLC purity). $^1H$ NMR (DMSO-$d_6$) δ 12.00 (s, 1H), 11.38 (s, 1H), 8.44 (s, 1H), 8.44 (dd, 1H, J=23.91, 2.03 Hz), 8.13 (d, 1H, J=5.59 Hz), 8.06 (d, 1H, J=13.23 Hz), 7.92 (s, 1H), 7.42 (s, 1H), 7.29-7.38 (m, 2H), 6.46 (d, 1H, J=5.59 Hz), 6.32 (s, 1H); MS(ESI$^+$) m/z 442.1 (M+H)$^+$.

Example 27

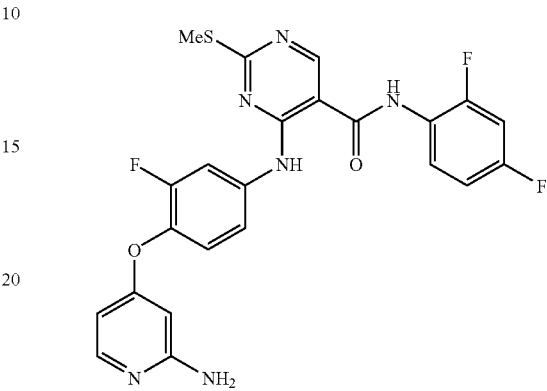

4-(4-(2-Aminopyridin-4-yloxy)-3-fluorophenylamino)-N-(2,4-difluorophenyl)-2-(methylthio)pyrimidine-5-carboxamide, bis(trifluoroacetic acid) salt

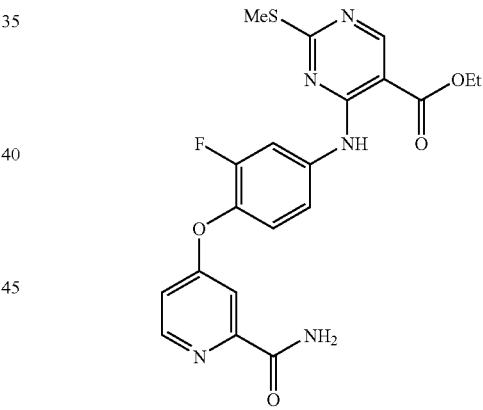

A) Ethyl 4-(4-(2-carbamoylpyridin-4-yloxy)-3-fluorophenylamino)-2-(methylthio)pyrimidine-5-carboxylate, hydrochloride salt To a mixture of ethyl 4-chloro-2-(methylthio)pyrimidine-5-carboxylate (Alpha Aesar, 2.08 g, 8.93 mmol) and 4-(4-amino-2-fluorophenoxy)picolinamide (2.0 g, 8.09 mmol, Compound C of Example 3) in NMP (10 mL) was added a solution of 4 N HCl in 1,4-dioxane (4 mL, 16 mmol). After stirring overnight, the reaction mixture was diluted with water (200 mL) and the resulting solid was filtered and dried in vacuo to give the desired product (3.6 g, 93%) as a white solid. MS(ESI$^+$) m/z 444 (M+H)$^+$.

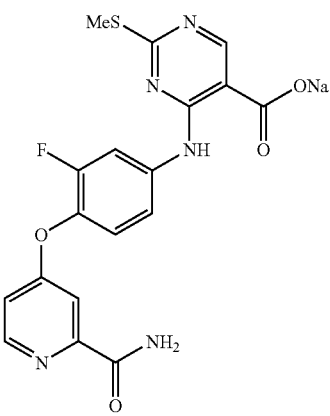

B) Sodium 4-(4-(2-carbamoylpyridin-4-yloxy)-3-fluorophenylamino)-2-(methylthio)pyrimidine-5-carboxylate To a suspension of ethyl 4-(4-(2-carbamoylpyridin-4-yloxy)-3-fluorophenylamino)-2-(methylthio)pyrimidine-5-carboxylate, hydrochloride salt (3.88 g, 8.08 mmol) in methanol (20 mL) and water (20 mL) was added a 4 N solution of sodium hydroxide in 1:1 methanol/water (5 mL, 20 mmol). After stirring overnight the reaction mixture was diluted methanol (100 mL) and water (100 mL) and was treated with additional sodium hydroxide solution (4 mL). After stirring 5 h, the mixture was partially concentrated under reduced pressure and the resulting suspension was filtered. The resulting solid was triturated with boiling ethanol, filtered and dried in vacuo to afford the carboxylate salt (2.94 g, 83%) as a white solid. MS(ESI$^+$) m/z 416 (M+H)$^+$.

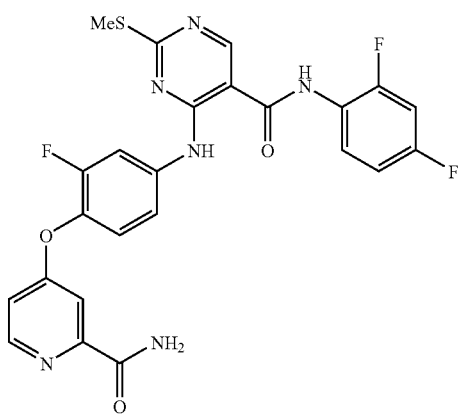

C) 4-(4-(2-Carbamoylpyridin-4-yloxy)-3-fluorophenylamino)-N-(2,4-difluorophenyl)-2-(methylthio)pyrimidine-5-carboxamide, hydrochloride salt To a suspension of sodium 4-(4-(2-carbamoylpyridin-4-yloxy)-3-fluorophenylamino)-2-(methylthio)pyrimidine-5-carboxylate (2.94 g, 6.72 mmol) in benzene (75 mL) was added thionyl chloride (4.9 mL, 62 mmol) and the solution was refluxed for 3 h. The reaction mixture was cooled to room temperature and concentrated in vacuo. The residue was treated with benzene and again concentrated in vacuo to remove the residual thionyl chloride. The resulting solid was taken up in THF (75 mL) and was treated with 2,4-difluoroaniline (2.6 g, 20.2 mmol). After stirring overnight the mixture was acidified with dilute aqueous HCl, was diluted with water (400 mL), and filtered. The resulting solid was purified by repeated trituration with methanol or ethyl acetate to give the amide (1.69 g, 45%) as a solid. MS(ESI$^+$) m/z 527 (M+H)$^+$.

D) 4-(4-(2-Aminopyridin-4-yloxy)-3-fluorophenylamino)-N-(2,4-difluorophenyl)-2-(methylthio)pyrimidine-5-carboxamide, bis(trifluoroacetic acid) salt 4-(4-(2-Carbamoylpyridin-4-yloxy)-3-fluorophenylamino)-N-(2,4-difluorophenyl)-2-(methylthio)pyrimidine-5-carboxamide, hydrochloride salt (169 mg, 0.30 mmol) was converted to the title compound (99 mg, 53%) in a manner similar to the preparation of 2-(4-(2-aminopyridin-4-yloxy)-3-fluorophenylamino)-N-(2,4-difluorophenyl)nicotinamide (Step E of Example 3). $^1$H NMR (DMSO-d$_6$) δ 11.06 (s, 1H), 10.51 (s, 1H), 8.94 (s, 1H), 8.12 (dd, 1H, J=13.0, 2.3 Hz), 7.98 (d, 1H, J=7.2 Hz), 7.90 (br s, 2H), 7.61-7.40 (m, 4H), 7.18 (m, 1H), 6.74 (dd, 1H, J=7.3, 2.5 Hz), 6.18 (d, 1H, J=2.4 Hz), 2.57 (s, 3H); MS(ESI$^+$) m/z 499 (M+H)$^+$.

Example 28

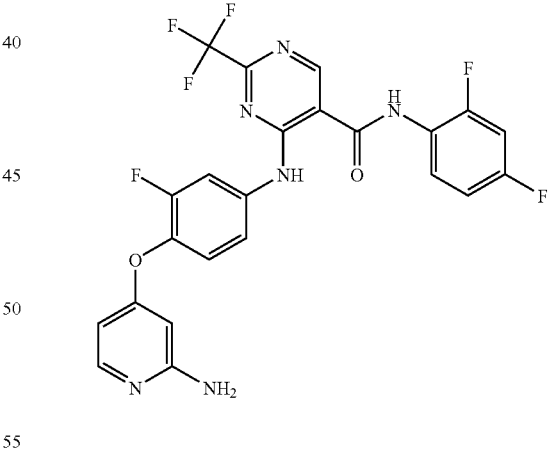

4-(4-(2-Aminopyridin-4-yloxy)-3-fluorophenylamino)-N-(2,4-difluorophenyl)-2-(trifluoromethyl)pyrimidine-5-carboxamide, dihydrochloride salt Ethyl 4-chloro-2-(trifluoromethyl)pyrimidine-5-carboxylate (Maybridge) was converted to the title compound in a manner similar to the procedure outlined in Steps A to D of Example 27. $^1$H NMR (CD$_3$OD) δ 9.3 (s, 1H), 8.14 (dd, 1H, J=12.8, 2.5 Hz), 7.86 (d, 1H, J=7.3 Hz), 7.75 (m, 1H), 7.56

(m, 1H), 7.41 (m, 1H), 7.20-7.03 (m, 2H), 6.71 (dd, 1H, J=7.2, 2.4 Hz), 6.27 (d, 1H, J=2.1 Hz); MS(ESI⁺) m/z 521 (M+H)⁺.

Example 29

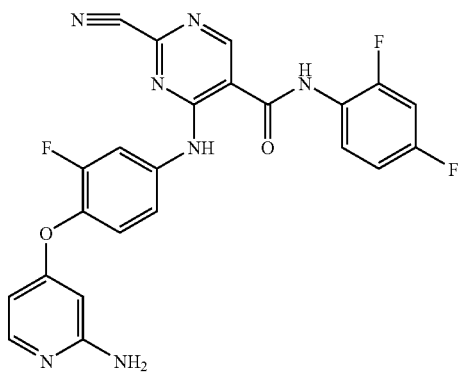

4-(4-(2-Aminopyridin-4-yloxy)-3-fluoropheny-lamino)-2-cyano-N-(2,4-difluorophenyl)pyrimidine-5-carboxamide, dihydrochloride salt

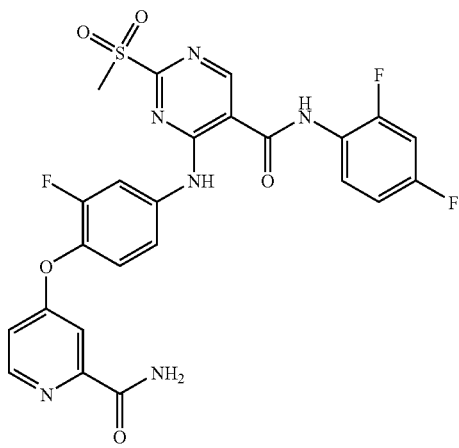

A) 4-(4-(2-Carbamoylpyridin-4-yloxy)-3-fluorophe-nylamino)-N-(2,4-difluorophenyl)-2-(methylsulfo-nyl)pyrimidine-5-carboxamide To a solution of 4-(4-(2-carbamoylpyridin-4-yloxy)-3-fluorophenylamino)-N-(2,4-difluorophenyl)-2-(methylthio) pyrimidine-5-carboxamide, hydrochloride salt (1.67 g, 2.95 mmol) in DMF (25 mL) was added m-CPBA (approx. 90%, 1.33 g, 6.9 mmol) in portions. After the reaction was complete (16 h) the solvent was partially concentrated under reduced pressure. The resulting suspension was diluted with an excess of 10% aqueous sodium sulfite and the resulting solid was filtered, washed with water, and dried in vacuo. The solid was purified by repeated trituration with ethyl acetate/hexane to give the sulfone (1.34 g, 81%) as a white solid. MS(ESI⁺) m/z 559 (M+H)⁺.

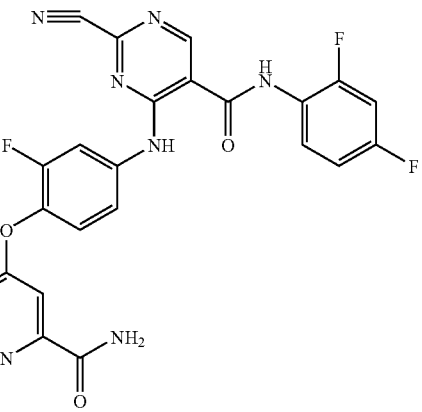

B) 4-(4-(2-Carbamoylpyridin-4-yloxy)-3-fluorophe-nylamino)-2-cyano-N-(2,4-difluorophenyl)pyrimi-dine-5-carboxamide To a solution of 4-(4-(2-carbamoylpyridin-4-yloxy)-3-fluorophenylamino)-N-(2,4-difluorophenyl)-2-(methylsul-fonyl)pyrimidine-5-carboxamide (200 mg, 0.36 mmol) in DMF (4 mL) was added potassium cyanide (94 mg, 1.44 mmol) and the mixture was heated to 80° C. After 5 h. The mixture was cooled to rt and the solvent was removed in vacuo. The residue was diluted with brine and extracted with EtOAc. The combined organic layers were washed with brine, dried over anhydrous MgSO₄, and concentrated in vacuo to give the nitrile (171 mg, 94%) as a solid. MS(ESI⁺) m/z 506 (M+H)⁺.

C) 4-(4-(2-Aminopyridin-4-yloxy)-3-fluoropheny-lamino)-2-cyano-N-(2,4-difluorophenyl)pyrimidine-5-carboxamide, dihydrochloride salt 4-(4-(2-Carbamoylpyridin-4-yloxy)-3-fluoropheny-lamino)-2-cyano-N-(2,4-difluorophenyl)pyrimidine-5-car-boxamide (171 mg, 0.33 mmol) was converted to the title compound (90 mg, 53%) in a manner similar to the preparation of 2-(4-(2-aminopyridin-4-yloxy)-3-fluoropheny-lamino)-N-(2,4-difluorophenyl)nicotinamide (Step E of Example 3). ¹H NMR (DMSO-d₆) δ 10.85 (s, 1H), 10.83 (s, 1H), 9.11 (s, 1H), 7.99 (m, 2H), 7.83 (br s, 2H), 7.68-7.40 (m, 4H), 7.20 (m, 1H), 6.75 (dd, 1H, J=7.3, 2.4 Hz), 6.20 (d, 1H, J=2.4 Hz); MS(ESI⁺) m/z 478 (M+H)⁺.

Example 30

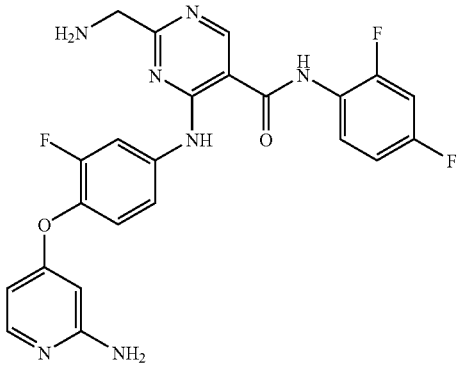

2-(Aminomethyl)-4-(4-(2-aminopyridin-4-yloxy)-3-fluorophenylamino)-N-(2,4-difluorophenyl)pyrimidine-5-carboxamide, trihydrochloride salt To a solution of 4-(4-(2-aminopyridin-4-yloxy)-3-fluorophenylamino)-2-cyano-N-(2,4-difluorophenyl)pyrimidine-5-carboxamide, dihydrochloride salt (48 mg, 0.092 mmol) in methanol (1 mL) was added 1 N HCl in ether (30 µL, 0.03 mmol), and 20% palladium hydroxide on carbon (48 mg). The suspension was purged with hydrogen and was stirred 2 h. Additional palladium hydroxide (38 mg) and methanol (1 mL) was added and the mixture was stirred an additional 4 h. The mixture was filtered through Celite® and the filtrate concentrated in vacuo. The resultant residue was purified by preparative (RP) HPLC (gradient from 34% to 90% aqueous methanol with 0.1% TFA). The appropriate fractions were combined and treated with Amberlyst A-21 ion exchange resin, filtered and concentrated in vacuo to give the freebase. The residue was dissolved in anhydrous THF (2 mL), and acidified with 1N HCl in ether. The reaction mixture was stirred for 10 min, the solvent was removed in vacuo and the solid was triturated in ether to afford the amine (20 mg, 39%) as an off-white solid. $^1$H NMR (DMSO-$d_6$) δ 10.99 (s, 1H), 10.78 (s, 1H), 9.16 (s, 1H), 8.48 (br s, 2H), 8.17 (dd, 1H, J=12.9, 2.4 Hz), 7.99 (d, 1H, J=7.2 Hz), 7.87 (br s, 2H), 7.62 (m, 2H), 7.43 (m, 2H), 7.20 (m, 1H), 6.70 (dd, 1H, J=7.2, 2.4 Hz), 6.21 (d, 1H, J=2.3 Hz), 4.21 (m, 2H); MS(ESI$^+$) m/z 482 (M+H)$^+$.

Example 31

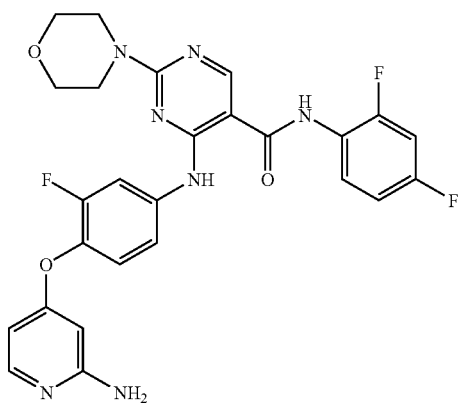

4-(4-(2-Aminopyridin-4-yloxy)-3-fluorophenylamino)-N-(2,4-difluorophenyl)-2-morpholinopyrimidine-5-carboxamide, trihydrochloride salt

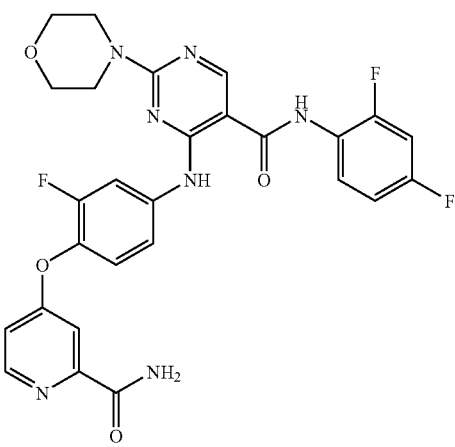

A) 4-(4-(2-Carbamoylpyridin-4-yloxy)-3-fluorophenylamino)-N-(2,4-difluorophenyl)-2-morpholinopyrimidine-5-carboxamide To a suspension of 4-(4-(2-carbamoylpyridin-4-yloxy)-3-fluorophenylamino)-N-(2,4-difluorophenyl)-2-(methylsulfonyl)pyrimidine-5-carboxamide (75 mg, 0.13 mmol) in THF (4 mL) was added morpholine (100 mg, 1.1 mmol) and the reaction mixture was stirred 15 min. The solvent was removed in vacuo and the resulting solid was triturated in methanol/ether to give the desired product (55 mg, 75%) as a white solid. MS(ESI$^+$) m/z 566 (M+H)$^+$.

B) 4-(4-(2-Aminopyridin-4-yloxy)-3-fluorophenylamino)-N-(2,4-difluorophenyl)-2-morpholinopyrimidine-5-carboxamide, trihydrochloride salt 4-(4-(2-Carbamoylpyridin-4-yloxy)-3-fluorophenylamino)-N-(2,4-difluorophenyl)-2-morpholinopyrimidine-5-carboxamide (55 mg, 0.01 mmol) was converted to the title compound (16 mg, 26%) in a manner similar to the preparation of 2-(4-(2-aminopyridin-4-yloxy)-3-fluorophenylamino)-N-(2,4-difluorophenyl)nicotinamide (Step E of Example 3). $^1$H NMR (DMSO-$d_6$) δ 11.24 (s, 1H), 10.20 (s, 1H), 8.85 (s, 1H), 7.92 (m, 2H), 7.82 (br s, 2H), 7.48-7.35 (m, 4H), 7.08 (m, 1H), 6.65 (dd, 1H, J=7.3, 2.5 Hz), 6.12 (d, 1H, J=2.4 Hz), 3.74 (m, 4H) 3.63 (m, 4H); MS(ESI$^+$) m/z 538 (M+H)$^+$.

The following compounds were prepared from the appropriate amine similarly to the procedure outlined in Example 31 (Steps A-B).

Example 32

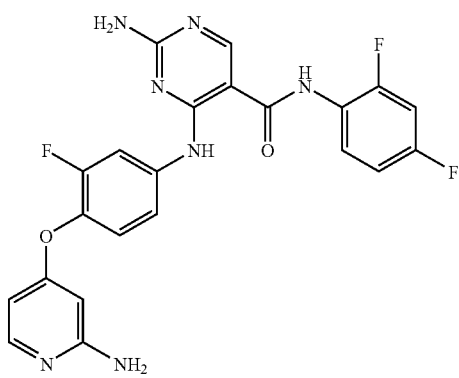

2-Amino-4-(4-(2-aminopyridin-4-yloxy)-3-fluorophenylamino)-N-(2,4-difluorophenyl)pyrimidine-5-carboxamide, trihydrochloride salt Ammonia in methanol was used to convert 4-(4-(2-carbamoylpyridin-4-yloxy)-3-fluorophenylamino)-N-(2,4-difluorophenyl)-2-(methylsulfonyl)pyrimidine-5-carboxamide (Compound A of Example 29) to the title compound in a manner similar to the procedure outlined in Example 31 (Steps A-B). MS(ESI$^+$) m/z 468 (M+H)$^+$.

Example 33

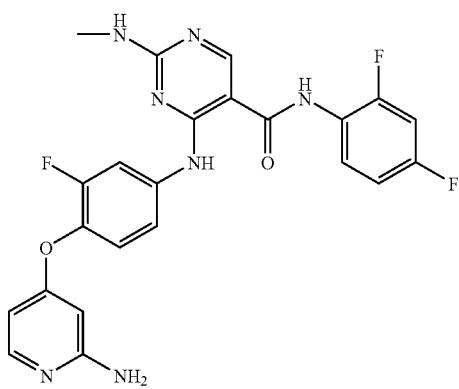

4-(4-(2-Aminopyridin-4-yloxy)-3-fluorophenylamino)-N-(2,4-difluorophenyl)-2-(methylamino)pyrimidine-5-carboxamide, trihydrochloride salt Methylamine in ethanol was used to convert 4-(4-(2-carbamoylpyridin-4-yloxy)-3-fluorophenylamino)-N-(2,4-difluorophenyl)-2-(methylsulfonyl)pyrimidine-5-carboxamide (Compound A of Example 29) to the title compound in a manner similar to the procedure outlined in Example 31 (Steps A-B). MS(ESI$^+$) m/z 482 (M+H)$^+$.

Example 34

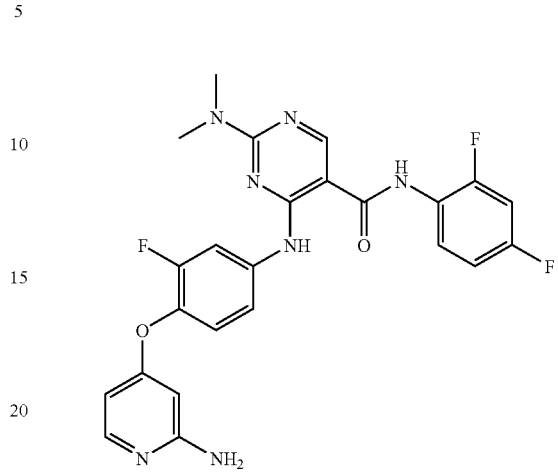

4-(4-(2-Aminopyridin-4-yloxy)-3-fluorophenylamino)-N-(2,4-difluorophenyl)-2-(dimethylamino)pyrimidine-5-carboxamide, trihydrochloride salt Dimethylamine in THF was used to convert 4-(4-(2-carbamoylpyridin-4-yloxy)-3-fluorophenylamino)-N-(2,4-difluorophenyl)-2-(methylsulfonyl)pyrimidine-5-carboxamide (Compound A of Example 29) to the title compound in a manner similar to the procedure outlined in Example 31 (Steps A-B). MS(ESI$^+$) m/z 496 (M+H)$^+$.

Example 35

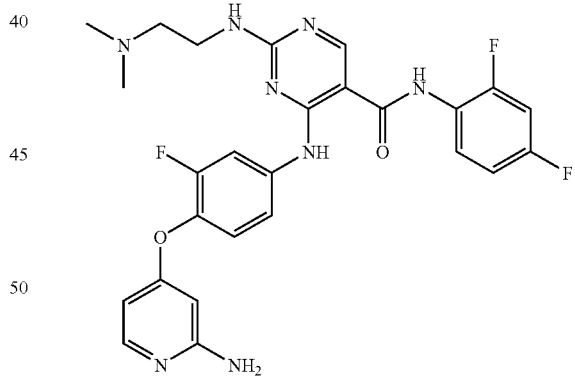

4-(4-(2-Aminopyridin-4-yloxy)-3-fluorophenylamino)-N-(2,4-difluorophenyl)-2-(2-(dimethylamino)ethylamino)pyrimidine-5-carboxamide, trihydrochloride salt N,N'-Dimethylethylenediamine was used to convert 4-(4-(2-carbamoylpyridin-4-yloxy)-3-fluorophenylamino)-N-(2,4-difluorophenyl)-2-(methylsulfonyl)pyrimidine-5-carboxamide (Compound A of Example 29) to the title compound in a manner similar to the procedure outlined in Example 31 (Steps A-B)
MS(ESI$^+$) m/z 539 (M+H)$^+$..

Example 36

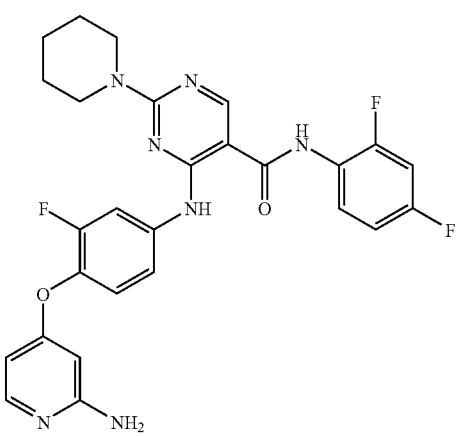

4-(4-(2-Aminopyridin-4-yloxy)-3-fluorophenylamino)-N-(2,4-difluorophenyl)-2-(piperidin-1-yl)pyrimidine-5-carboxamide, trihydrochloride salt Piperidine was used to convert 4-(4-(2-carbamoylpyridin-4-yloxy)-3-fluorophenylamino)-N-(2,4-difluorophenyl)-2-(methylsulfonyl)pyrimidine-5-carboxamide (Compound A of Example 29) to the title compound in a manner similar to the procedure outlined in Example 31 (Steps A-B). MS(ESI$^+$) m/z 536 (M+H)$^+$.

Example 37

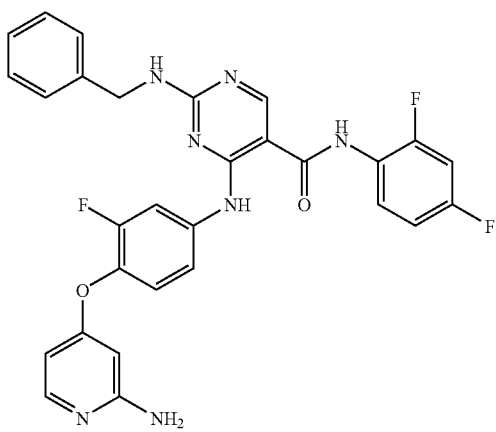

4-(4-(2-Aminopyridin-4-yloxy)-3-fluorophenylamino)-2-(benzylamino)-N-(2,4-difluorophenyl)pyrimidine-5-carboxamide, trihydrochloride salt Benzylamine was used to convert 4-(4-(2-carbamoylpyridin-4-yloxy)-3-fluorophenylamino)-N-(2,4-difluorophenyl)-2-(methylsulfonyl)pyrimidine-5-carboxamide (Compound A of Example 29) to the title compound in a manner similar to the procedure outlined in Example 31 (Steps A-B). MS(ESI$^+$) m/z 558 (M+H)$^+$.

Example 38

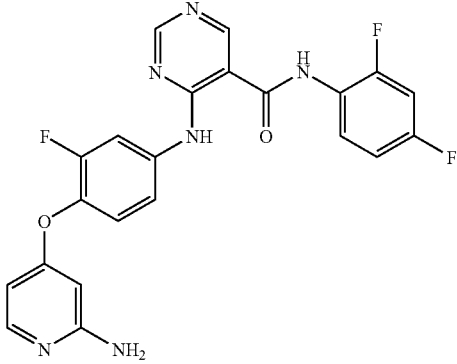

4-(4-(2-Aminopyridin-4-yloxy)-3-fluorophenylamino)-N-(2,4-difluorophenyl)pyrimidine-5-carboxamide, bis(trifluoroacetic acid) salt

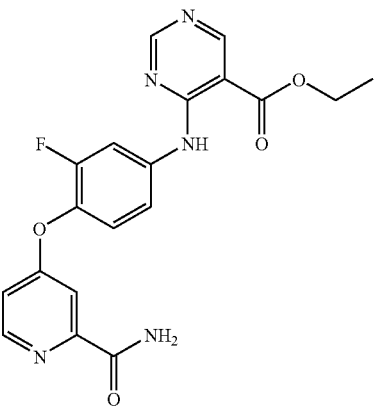

A) Ethyl 4-(4-(2-carbamoylpyridin-4-yloxy)-3-fluorophenylamino)pyrimidine-5-carboxylate To a solution of ethyl 4-(4-(2-carbamoylpyridin-4-yloxy)-3-fluorophenylamino)-2-(methylthio)pyrimidine-5-carboxylate (260 mg, 0.58 mmol) in ethanol (5 mL) was added Raney nickel in water (Raney®2400, approx. 3 g). The mixture was heated to 70° C. and was allowed to stir overnight. The mixture was filtered through Celite® and the filtrate was concentrated in vacuo to give the desired product (91 mg, 39%) as a solid. MS(ESI$^+$) m/z 398 (M+H)$^+$.

B) 4-(4-(2-Aminopyridin-4-yloxy)-3-fluorophenylamino)-N-(2,4-difluorophenyl)pyrimidine-5-carboxamide, bis(trifluoroacetic acid) salt Ethyl 4-(4-(2-carbamoylpyridin-4-yloxy)-3-fluorophenylamino)pyrimidine-5-carboxylate was converted to the title compound in a manner similar to the procedure outlined for Example 27 (Steps B-D). $^1$H NMR (CD$_3$OD) δ 9.04 (s, 1H), 8.83 (s, 1H), 8.15 (dd, 1H, J=13.0, 2.3 Hz), 7.86 (d, 1H, J=7.4 Hz), 7.72 (m, 1H), 7.53 (m, 1H), 7.38 (m, 1H), 7.18-7.03 (m, 2H), 6.71 (dd, 1H, J=7.2, 2.4 Hz), 6.26 (d, 1H, J=2.3 Hz); MS(ESI$^+$) m/z 453 (M+H)$^+$.

Example 39

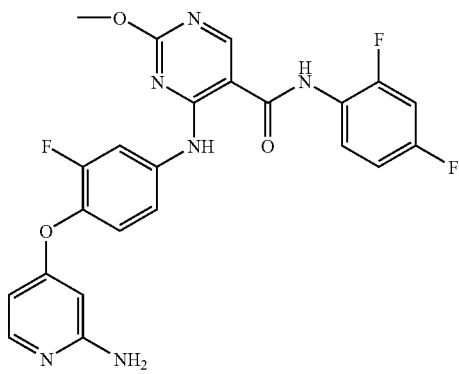

4-(4-(2-Aminopyridin-4-yloxy)-3-fluorophenylamino)-N-(2,4-difluorophenyl)-2-methoxypyrimidine-5-carboxamide, dihydrochloride salt and Example 40

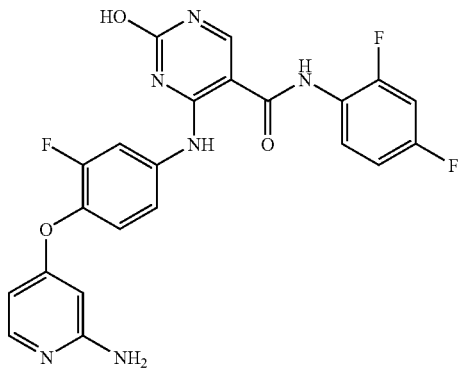

4-(4-(2-Aminopyridin-4-yloxy)-3-fluorophenylamino)-N-(2,4-difluorophenyl)-2-hydroxypyrimidine-5-carboxamide, dihydrochloride salt To a solution of 4-(4-(2-carbamoylpyridin-4-yloxy)-3-fluorophenylamino)-N-(2,4-difluorophenyl)-2-(methylsulfonyl)pyrimidine-5-carboxamide (100 mg, 0.18 mmol) in methanol (5 mL) was added sodium methoxide (60 mg, 1.1 mmol) and the mixture was heated to 64° C. After stirring 4.5 h the reaction mixture was cooled to rt and stirred overnight. The mixture was acidified with hydrochloric acid and the solvent was removed in vacuo. The resulting solid was heated in ethyl acetate and filtered. The filtrate was concentrated in vacuo and the resulting solid was triturated with water and filtered to give a mixture of the methoxy and hydroxy substituted pyrimidines (66 mg) as a solid. The mixture was converted to the title compounds in a manner similar to the preparation of 2-(4-(2-aminopyridin-4-yloxy)-3-fluorophenylamino)-N-(2,4-difluorophenyl)nicotinamide (Step E of Example 3) followed by separation of the products by preparative (RP) HPLC (gradient from 44 to 90%) to afford the title compounds.

Example 39

$^1$H NMR (CD$_3$OD) δ 8.89 (s, 1H), 7.86 (m, 1H), 7.77 (d, 1H, J=7.3 Hz), 7.61 (m, 1H), 7.52 (m, 1H), 7.38 (m, 1H), 7.03 (m, 1H), 6.95 (m, 1H), 6.58 (dd, 1H, J=7.3, 2.5 Hz), 6.19 (d, 1H, J=2.4 Hz), 4.12 (s, 3H); MS(ESI$^+$) m/z 483 (M+H)$^+$.

Example 40

$^1$H NMR (CD$_3$OD) δ 8.74 (s, 1H), 7.90 (m, 2H), 7.72 (m, 1H), 7.48 (m, 2H), 7.13 (m, 1H), 7.05 (m, 1H), 6.72 (dd, 1H, J=7.2, 2.4 Hz), 6.37 (d, 1H, J=2.3 Hz); MS(ESI$^+$) m/z 469 (M+H)$^+$.

Example 41

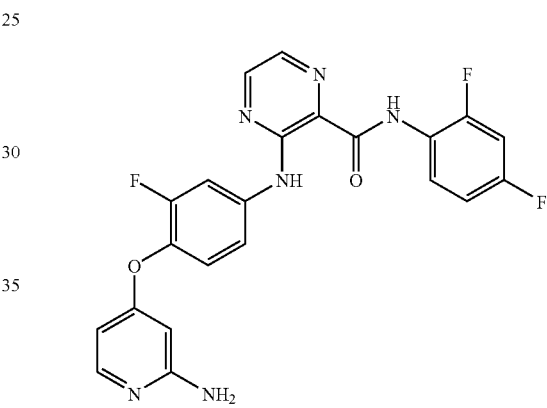

3-(4-(2-Aminopyridin-4-yloxy)-3-fluorophenylamino)-N-(2,4-difluorophenyl)pyrazine-2-carboxamide, bis(trifluoroacetic acid) salt

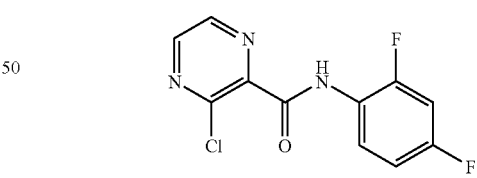

A) 3-Chloro-N-(2,4-difluorophenyl)pyrazine-2-carboxamide

To a mixture of 3-chloropyrazine-2-carboxylic acid (Tyger Scientific, 500 mg, 3.15 mmol) in methylene chloride (30 mL) and DMF (0.1 mL) was added oxalyl chloride (593 mg, 4.7 mmol). After stirring 30 min the reaction mixture was concentrated in vacuo. The residue was taken up in acetonitrile (12 mL) and was treated with triethylamine (920 mg, 9.1 mmol) and 2,4-difluoroaniline (430 mg, 3.3 mmol) and stirred 30 min. The reaction mixture was partitioned between ethyl acetate and brine. The organic layer was washed with brine, dried over anhydrous MgSO$_4$, and then concentrated in vacuo. The resulting solid was recrystallized (ethyl acetate/hexanes) to give the amide (455 mg, 53%) as a solid. MS(ESI$^+$) m/z 270 (M+H)$^+$.

B) 3-(4-(2-Aminopyridin-4-yloxy)-3-fluorophenylamino)-N-(2,4-difluorophenyl)pyrazine-2-carboxamide, bis(trifluoroacetic acid) salt 3-Chloro-N-(2,4-difluorophenyl)pyrazine-2-carboxamide and 4-(4-amino-2-fluorophenoxy)picolinamide were converted to the title compound in a manner similar to the procedures outlined in Step D of Example 1 and Step E of Example 3. $^1$H NMR (CD$_3$OD) δ 11.24 (s, 1H), 8.50 (d, 1H, J=2.4 Hz), 8.19 (m, 3H), 7.86 (d, 1H, J=7.2 Hz), 7.52 (m, 1H), 7.33 (m, 1H), 7.18 (m, 1H), 7.08 (m, 1H), 6.70 (dd, 1H, J=7.3, 2.5 Hz), 6.25 (d, 1H, J=2.2 Hz); MS(ESI$^+$) m/z 453 (M+H)$^+$.

Example 42

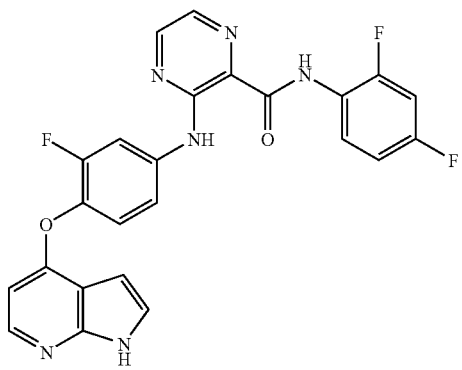

3-(4-(1H-Pyrrolo[2,3-b]pyridin-4-yloxy)-3-fluorophenylamino)-N-(2,4-difluorophenyl)pyrazine-2-carboxamide, bis(trifluoroacetic acid) salt 3-Chloro-N-(2,4-difluorophenyl)pyrazine-2-carboxamide was converted to the title compound in a manner similar to the procedure outlined in Step D of Example 1. $^1$H NMR (CD$_3$OD) δ 8.44 (d, 1H, J=2.4 Hz), 8.27-8.11 (m, 4H), 7.49 (m, 2H), 7.38 (m, 1H), 7.13 (m, 1H), 7.01 (m, 1H), 6.83 (dd, 1H, J=7.3, 2.4 Hz), 6.62 (d, 1H, J=2.3 Hz); MS(ESI$^+$) m/z 477 (M+H)$^+$.

We claim:
1. A compound having the following Formula I or Formula II:

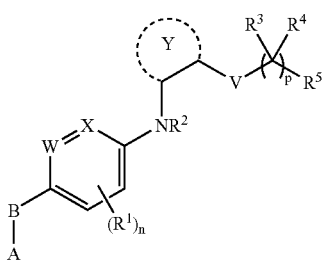

or a salt thereof:

wherein
each R$^1$ is H, halogen, halogenated alkyl, cyano, NO$_2$, OR$^6$, NR$^7$R$^8$, alkyl, substituted alkyl, cycloalkyl, substituted cycloalkyl, aryl, substituted aryl, heteroaryl, substituted heteroaryl, arylalkyl, substituted arylalkyl, heterocycloalkyl, or substituted heterocycloalkyl;

B is O, NR$^9$, S, SO, SO$_2$, or CR$^{10}$R$^{11}$;

W and X are each CH;

V is CO;

n is 1 to 4;

m is 1 to 4;

p is 0 to 2;

l is 1 to 2;

R$^2$ is H, alkyl, substituted alkyl, cycloalkyl, or substituted cycloalkyl;

R$^3$ and R$^4$ are independently H, halogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycloalkyl, or substituted heterocycloalkyl, or taken together to form a carbocyclic or heterocyclic ring of 3 to 8 atoms;

R$^5$ is —NR$^{12}$R$^{13}$, —OR$^{14}$, alkyl, substituted alkyl, haloalkyl, cycloalkyl, substituted cycloalkyl, aryl, substituted aryl, heteroaryl, substituted heteroaryl, aryalkyl, substituted arylalkyl, heterocycloalkyl, or heterocycloalkyl;

R$^6$, R$^7$, R$^8$, and R$^9$ are each independently H, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycloalkyl or substituted heterocycloalkyl;

R$^{10}$ and R$^{11}$ are each independently H, halogen, alkyl, substituted alkyl, cycloalkyl, substituted cycloalkyl, aryl, substituted aryl, benzyl, heteroaryl, substituted heteroaryl, heterocycloalkyl, or substituted heterocycloalkyl, or taken together to form a carbocyclic or heterocyclic ring of 3 to 8 atoms;

R$^{12}$ and R$^{13}$ are each independently H, alkyl, substituted alkyl, cycloalkyl, substituted cycloalkyl, arylalkyl, substituted arylalkyl, aryl, substituted aryl, heteroaryl, substituted heteroaryl, heteroarylalkyl, substituted heteroarylalkyl, heterocycloalkyl, or substituted heterocycloalkyl, or taken together to form a heterocyclic ring of 3 to 8 atoms;

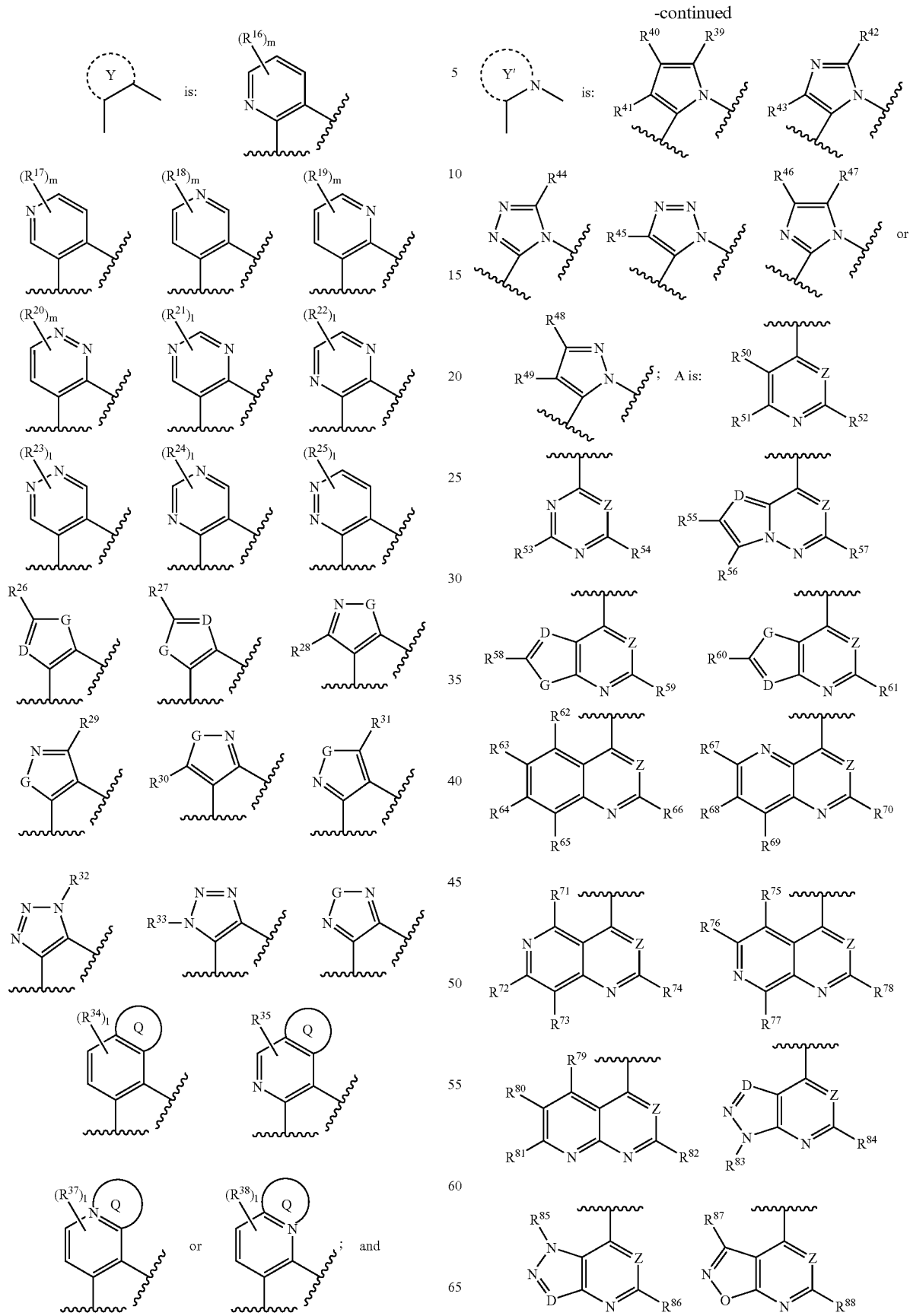

-continued

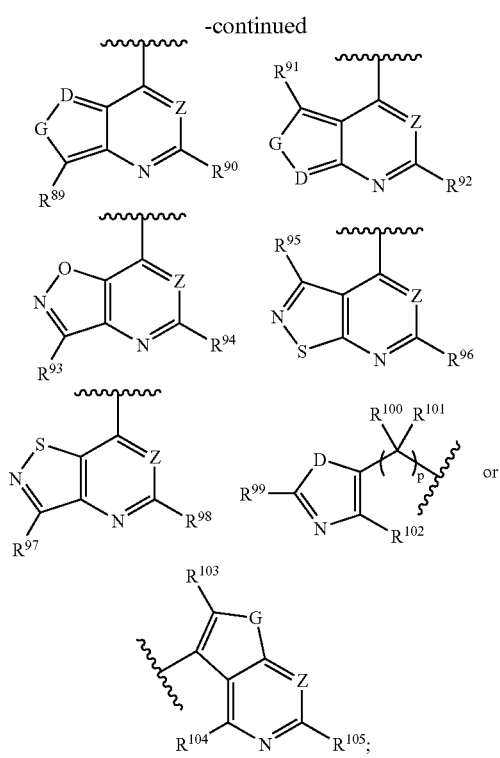

wherein
G is O, S, or NR$^{106}$;
D is CR$^{107}$ or N;
Z is N or CR$^{108}$;
Q is an optionally substituted carbocyclic or heterocyclic ring containing 4-8 atoms;
R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$, R$^{34}$, R$^{35}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$, R$^{48}$, R$^{49}$, R$^{50}$, R$^{51}$, R$^{52}$, R$^{53}$, R$^{54}$, R$^{55}$, R$^{56}$, R$^{57}$, R$^{58}$, R$^{59}$, R$^{60}$, R$^{61}$, R$^{62}$, R$^{63}$, R$^{64}$, R$^{65}$, R$^{66}$, R$^{67}$, R$^{68}$, R$^{69}$, R$^{70}$, R$^{71}$, R$^{72}$, R$^{73}$, R$^{74}$, R$^{75}$, R$^{76}$, R$^{77}$, R$^{78}$, R$^{79}$, R$^{80}$, R$^{81}$, R$^{82}$, R$^{84}$, R$^{86}$, R$^{87}$, R$^{88}$, R$^{89}$, R$^{90}$, R$^{91}$, R$^{92}$, R$^{93}$, R$^{94}$, R$^{95}$, R$^{96}$, R$^{97}$, R$^{98}$, R$^{99}$, R$^{102}$, R$^{103}$, R$^{104}$, R$^{105}$, R$^{107}$ and R$^{108}$ are each independently H, halogen, haloalkyl, NO$_2$, cyano, OR$^{109}$, NR$^{110}$R$^{111}$, CO$_2$R$^{112}$, C(O)NR$^{113}$R$^{114}$, SO$_2$R$^{115}$, SO$_2$NR$^{116}$R$^{117}$, NR$^{118}$SO$_2$R$^{119}$, NR$^{120}$C(O)R$^{121}$, NR$^{122}$CO$_2$R$^{123}$, —CO(CH$_2$)$_m$R$^{124}$; -CONH(CH$_2$)$_m$R$^{125}$, SR$^{126}$, SOR$^{127}$ aminoalkyl, alkylaminoalkyl, alkylaminoalkylamino, diaalkylaminoalkylamino, alkylaminoalkynyl, C$_1$ to C$_6$ alkyl, substituted C$_1$ to C$_6$ alkyl, C$_3$ to C$_7$ cycloalkyl, substituted C$_3$ to C$_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl; or R$^{40}$ is taken together with either R$^{39}$ or R$^{41}$ to form a carbocyclic, or an unsaturated or saturated heterocyclic ring of 3 to 8 atoms;

R$^{32}$, R$^{33}$, R$^{83}$, and R$^{85}$ are each independently H, halogenated alkyl, —CO$_2$R$^{128}$, —SO$_2$R$^{129}$, —CO(CH$_2$)$_m$R$^{130}$, alkylaminoalkyl, alkylaminoalkynyl, C$_1$ to C$_6$ alkyl, substituted C$_1$ to C$_6$ alkyl, C$_3$ to C$_7$ cycloalkyl, substituted C$_3$ to C$_7$ cycloalkyl, hydroxyalkyl, aryl, substituted aryl, heteroaryl, substituted heteroaryl, arylalkyl, substituted arylalkyl, or heterocycloalkyl;

R$^{100}$ and R$^{101}$ are independently selected from H, halogen, alkyl, substituted alkyl, cycloalkyl, substituted cycloalkyl, aryl, substituted aryl, heteroaryl, substituted heteroaryl, heterocycloalkyl, or substituted heterocycloalkyl, or taken together to form a carbocyclic or heterocyclic ring of 3 to 8 atoms; and R$^{14}$, R$^{106}$, R$^{109}$, R$^{110}$, R$^{111}$, R$^{112}$, R$^{113}$, R$^{114}$, R$^{115}$, R$^{116}$, R$^{117}$, R$^{118}$, R$^{119}$, R$^{120}$, R$^{121}$, R$^{122}$, R$^{123}$, R$^{124}$, R$^{125}$, R$^{126}$, R$^{127}$, R$^{128}$, R$^{129}$ and R$^{130}$ are each independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

2. The compound according to claim 1 wherein A is

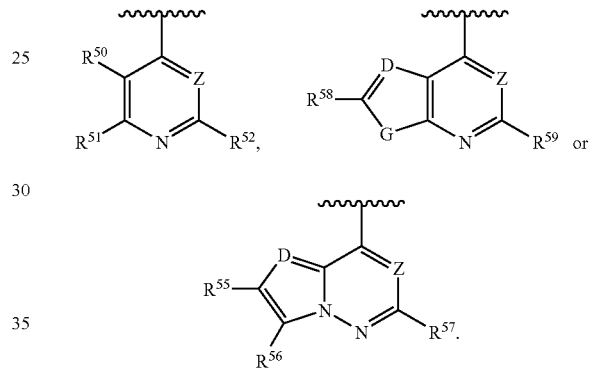

3. The compound according to claim 2 wherein D is —CH, G is —NH, Z is N or —CH and R$^{50}$, R$^{51}$, R$^{52}$, R$^{58}$ and R$^{59}$ are each, independently, H, amino, or substituted C$_1$-C$_6$ alkyl.

4. The compound according to claim 1 wherein B is O.

5. The compound according to claim 1 wherein

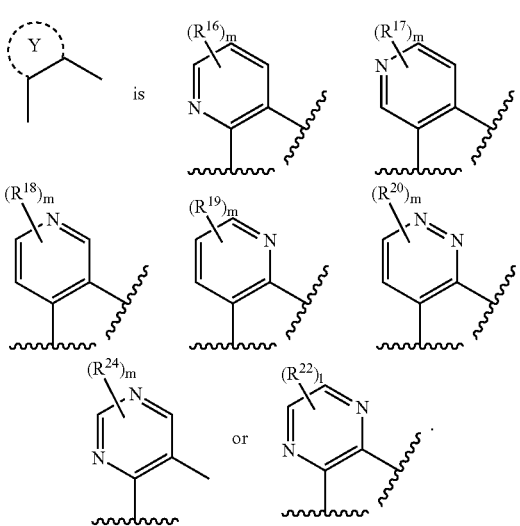

6. The compound according to claim 5 wherein

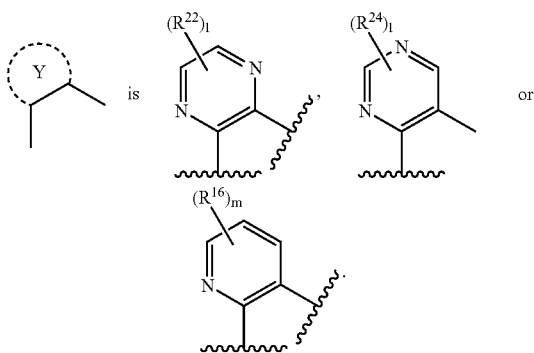

is

7. The compound according to claim 6 wherein each $R^{22}$, $R^{24}$ and $R^{16}$ is independently H, hydroxyl, alkoxy, halo, $C_1$-$C_6$ alkyl, haloalkyl, —$NR^{110}R^{111}$, —$SR^{126}$, —CN, amino, aminoalkyl, alkylamino, dialkylaminoalkylamino, arylalkylamino or heterocycloalkyl.

8. The compound according to claim 7 wherein each $R^{22}$, $R^{24}$, and $R^{16}$ is, independently, —OH, —$OCH_3$, Br, Cl, —$CH_3$, —$SCH_3$, —$CF_3$, —CN, —$CH_2NH_2$, morpholinyl, piperazinyl, or —$NR^{10}R^{11}$, wherein $R^{10}$ and $R^{11}$ are, independently, H, $C_1$-$C_6$ alkyl, benzyl, or dialkylaminoalkyl.

9. The compound according to claim 1 wherein each $R^1$ is independently H or F.

10. The compound according to claim 1 wherein $R^5$ is an optionally substituted phenyl, optionally substituted indolinyl, or —$NR^{12}R^{13}$.

11. The compound according to claim 10 wherein said phenyl is substituted with halo, $C_1$-$C_6$ alkyl, hydroxyalkyl, heteroaryl, heterocycloalkyl, amino, or alkylamino.

12. The compound having the following Formula I:

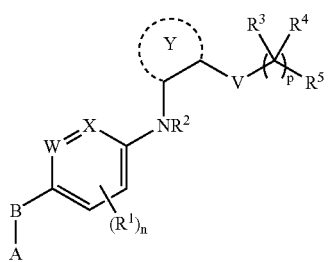

I or a salt thereof wherein:
each $R^1$ is H, halogen, halogenated alkyl, cyano, $NO_2$, $OR^6$, $NR^7R^8$, alkyl, substituted alkyl, cycloalkyl, substituted cycloalkyl, aryl, substituted aryl, heteroaryl, substituted heteroaryl, aryalkyl, substituted arylalkyl, heterocycloalkyl, or substituted heterocycloalkyl;
B is O, $NR^9$, S, SO, $SO_2$, or $CR^{10}R^{11}$;
W and X are each CH;
V is CO;
n is 1 to 4;
m is 1 to 4;
p is 0 to 2;
l is 1 to 2;
$R^2$ is H, alkyl, substituted alkyl, cycloalkyl, or substituted cycloalkyl;

$R^3$ and $R^4$ are independently H, halogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycloalkyl, substituted heterocycloalkyl or taken together to form a carbocyclic or heterocyclic ring of 3 to 8 atoms;
$R^5$ is —$NR^{12}R^{13}$, —$OR^{14}$, alkyl, substituted alkyl, haloalkyl, cycloalkyl, substituted cycloalkyl, aryl, substituted aryl, heteroaryl, substituted heteroaryl, aryalkyl, substituted arylalkyl, heterocycloalkyl, or substituted heterocycloalkyl;
$R^6$, $R^7$, $R^8$, and $R^9$ are each independently H, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycloalkyl, or substituted heterocycloalkyl;
$R^{10}$ and $R^{11}$ are each independently H, halogen, alkyl, substituted alkyl, cycloalkyl, substituted cycloalkyl, aryl, substituted aryl, heteroaryl, substituted heteroaryl, heterocycloalkyl, or substituted heterocycloalkyl, or taken together to form a carbocyclic or heterocyclic ring of 3 to 8 atoms;
$R^{12}$ and $R^{13}$ are each independently H, alkyl, substituted alkyl, cycloalkyl, substituted cycloalkyl, arylalkyl, substituted arylalkyl, aryl, substituted aryl, heteroaryl, substituted heteroaryl, heteroarylalkyl, substituted heteroarylalkyl, heterocycloalkyl, or substituted heterocycloalkyl, or taken together to form a heterocyclic ring of 3 to 8 atoms;

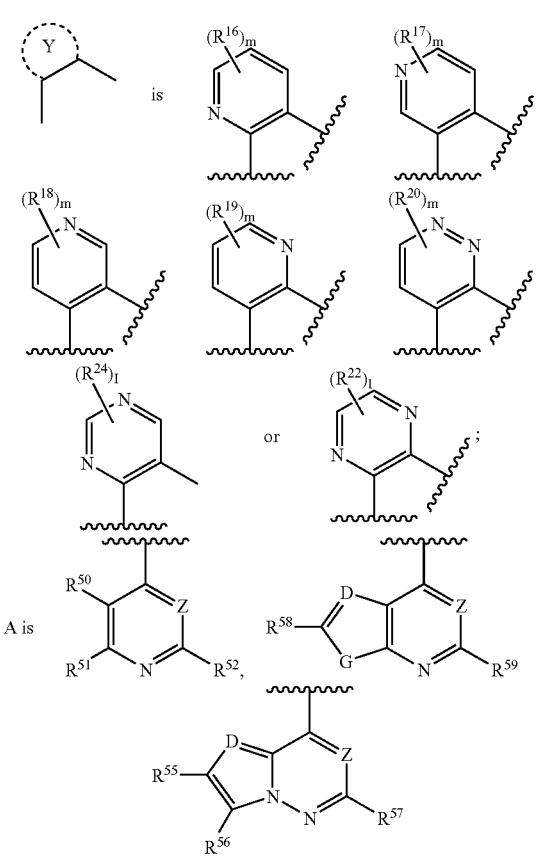

wherein
$R^{16}$, $R^{17}$, $R^{18}$, $R^{19}$, $R^{20}$, $R^{22}$, $R^{24}$, $R^{50}$, $R^{51}$, $R^{52}$, $R^{55}$, $R^{56}$, $R^{57}R^{58}$, and $R^{59}$ are each independently, H, halogen, halogenated alkyl, NO₂, cyano, OR¹⁰⁹, NR¹¹⁰OR¹¹¹, CO₂R¹¹², C(O)NR¹¹³R¹¹⁴, SO₂R¹¹⁵, SO₂NR¹¹⁶R¹¹⁷, NR¹¹⁸SO₂R¹¹⁹, NR¹²⁰C(O)R¹²¹, NR¹²²CO₂R¹²³, —CO(CH₂)$_m$R¹²⁴; —CONH(CH₂)$_m$R¹²⁵, SR¹²⁶, SOR¹²⁷, alkylaminoalkyl, alkylaminoalkynyl, C₁ to C₆ alkyl, substituted C₁ to C₆ alkyl, C₃ to C₇ cycloalkyl, substituted C₃ to C₇ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl; and R¹⁴, R¹⁰⁶, R¹⁰⁹, R¹¹⁰, R¹¹¹, R¹¹², R¹¹³, R¹¹⁴, R¹¹⁵, R¹¹⁶, R¹¹⁷, R¹¹⁸, R¹¹⁹, R¹²⁰, R¹²¹, R¹²², R¹²³, R¹²⁴, R¹²⁵, R¹²⁶, and R¹²⁷, are each independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

13. The compound according to claim 12 wherein each R²², R²⁴ and R¹⁶ are independently H, hydroxyl, alkoxy, halo, C₁-C₆ alkyl, haloalkyl, —NR¹¹⁰R¹¹¹, —SR¹²⁶, —CN, amino, or heterocycloalkyl.

14. The compound according to claim 12 wherein each R¹ is independently H or F.

15. The compound according to claim 12 wherein R⁵ is an optionally substituted phenyl, optionally substituted indolinyl, —NR¹⁰R¹¹, or alkylamino.

16. The compound according to claim 12 wherein said phenyl is substituted with halo, C₁-C₆ alkyl, hydroxyalkyl, heteroaryl, heterocycloalkyl, amino, or alkylamino.

17. A compound selected from group consisting of:
4-(4-(1H-Pyrrolo[2,3-b]pyridin-4-yloxy)-3-fluorophenylamino)-N-(2,4-difluorophenyl)nicotinamide, hydrochloride salt;
2-(4-(1H-Pyrrolo[2,3-b]pyridin-4-yloxy)-3-fluorophenylamino)-N-(2,4-difluorophenyl)nicotinamide, hydrochloride salt;
2-(4-(2-Aminopyridin-4-yloxy)-3-fluorophenylamino)-N-(2,4-difluorophenyl)nicotinamide, hydrochloride salt;
2-(4-(2-Aminopyridin-4-yloxy)-3-fluorophenylamino)-N-(4-chlorophenyl)nicotinamide, dihydrochloride salt;
4-(4-(2-Aminopyridin-4-yloxy)-3-fluorophenylamino)-N-(2,4-difluorophenyl)nicotinamide, dihydrochloride salt;
2-(4-(2-Aminopyridin-4-yloxy)-3-fluorophenylamino)-N-benzylnicotinamide, dihydrochloride salt;
2-(4-(1H-Pyrrolo[2,3-b]pyridin-4-yloxy)-3-fluorophenylamino)-N-benzylnicotinamide, dihydrochloride salt;
2-(4-(1H-Pyrrolo[2,3-b]pyridin-4-yloxy)-3-fluorophenylamino)-N-o-tolylnicotinamide, dihydrochloride salt;
2-(4-(1H-Pyrrolo[2,3-b]pyridin-4-yloxy)-3-fluorophenylamino)-N-(4-fluoro-2-methylphenyl)nicotinamide, dihydrochloride salt;
2-(4-(1H-Pyrrolo[2,3-b]pyridin-4-yloxy)-3-fluorophenylamino)-N-(2-chlorophenyl)nicotinamide, dihydrochloride salt;
2-(4-(1H-Pyrrolo[2,3-b]pyridin-4-yloxy)-3-fluorophenylamino)-N-(4-fluorobenzyl)nicotinamide, dihydrochloride salt;
2-(4-(1H-Pyrrolo[2,3-b]pyridin-4-yloxy)-3-fluorophenylamino)-N-(2-morpholino-1-phenylethyl)nicotinamide, trihydrochloride salt; 2-(4-(1H-Pyrrolo[2,3-b]pyridin-4-yloxy)-3-fluorophenylamino)-N-(2-(2-hydroxyethyl)phenyl)nicotinamide, bis(trifluoroacetic acid) salt;
2-(4-(1H-Pyrrolo[2,3-b]pyridin-4-yloxy)-3-fluorophenylamino)-N-(5-fluoropyridin-2-yl)nicotinamide, bis(trifluoroacetic acid) salt;
2-(4-(1H-Pyrrolo[2,3-b]pyridin-4-yloxy)-3-fluorophenylamino)-N-(2,4-difluorophenyl)-4-methoxynicotinamide, bis(triflouroacetic acid) salt;
2-(4-(1H-Pyrrolo[2,3-b]pyridine-4-yloxy)-3-fluorophenylamino)-N-(2,4-difluorophenyl)-4-hydroxynicotinamide, bis(trifluoroacetic acid) salt;
2-(4-(2-Aminopyridin-4-yloxy)-3-fluorophenylamino)-5-bromo-N-(2,4-difluorophenyl)nicotinamide, bis(trifluoroacetic acid) salt;
2-(4-(1H-Pyrrolo[2,3-b]pyridin-4-yloxy)-3-fluorophenylamino)-5-bromo-N-(2,4-difluorophenyl)nicotinamide, dihydrochloride salt;
2-(4-(2-Amino-3-(hydroxymethyl)pyridin-4-yloxy)-3-fluorophenylamino)-N-(2,4-difluorophenyl)nicotinamide, dihydrochloride salt;
2-(4-(1H-Pyrrolo[2,3-b]pyridin-4-yloxy)-3-fluorophenylamino)-N-(4-fluorophenyl)-N-methylnicotinamide, dihydrochloride salt;
2-(4-(1H-Pyrrolo[2,3-b]pyridin-4-yloxy)-3-fluorophenylamino)-N-(2,4-difluorophenyl)-6-methylnicotinamide, dihydrochloride salt;
2-(4-(1H-Pyrrolo[2,3-b]pyridin-4-yloxy)-3-fluorophenylamino)pyridin-3-yl)(5-fluoroindolin-1-yl)methanone, dihydrochloride salt;
2-(4-(1H-Pyrrolo[2,3-b]pyridin-4-yloxy)-3-fluorophenylamino)nicotinamide, bis(trifluoroacetic acid) salt;
2-(4-(1H-Pyrrolo[2,3-b]pyridin-4-yloxy)-3-fluorophenylamino)-N-methylnicotinamide, dihydrochloride salt;
2-(4-(1H-Pyrrolo[2,3-b]pyridin-4-yloxy)-3-fluorophenylamino)-5-chloro-N-methylnicotinamide, dihydrochloride salt;
2-(4-(1H-Pyrrolo[2,3-b]pyridin-4-yloxy)-3-fluorophenylamino)nicotinamide, bis(trifluoroacetic acid) salt;
4-(4-(2-Aminopyridin-4-yloxy)-3-fluorophenylamino)-N-(2,4-difluorophenyl)-2-(methylthio)pyrimidine-5-carboxamide, bis(trifluoroacetic acid) salt;
4-(4-(2-Aminopyridin-4-yloxy)-3-fluorophenylamino)-N-(2,4-difluorophenyl)-2-(trifluoromethyl)pyrimidine-5-carboxamide, dihydrochloride salt;
4-(4-(2-Aminopyridin-4-yloxy)-3-fluorophenylamino)-2-cyano-N-(2,4-difluorophenyl)pyrimidine-5-carboxamide, dihydrochloride salt;
2-(Aminomethyl)-4-(4-(2-aminopyridin-4-yloxy)-3-fluorophenylamino)-N-(2,4-difluorophenyl)pyrimidine-5-carboxamide, trihydrochloride salt;
4-(4-(2-Aminopyridin-4-yloxy)-3-fluorophenylamino)-N-(2,4-difluorophenyl)-2-morpholinopyrimidine-5-carboxamide, trihydrochloride salt;
2-Amino-4-(4-(2-aminopyridin-4-yloxy)-3-fluorophenylamino)-N-(2,4-difluorophenyl)pyrimidine-5-carboxamide, trihydrochloride salt;
4-(4-(2-Aminopyridin-4-yloxy)-3-fluorophenylamino)-N-(2,4-difluorophenyl)-2-(methylamino)pyrimidine-5-carboxamide, trihydrochloride salt;
4-(4-(2-Aminopyridin-4-yloxy)-3-fluorophenylamino)-N-(2,4-difluorophenyl)-2-(dimethylamino)pyrimidine-5-carboxamide, trihydrochloride salt;
4-(4-(2-Aminopyridin-4-yloxy)-3-fluorophenylamino)-N-(2,4-difluorophenyl)-2-(2-(dimethylamino)ethylamino)pyrimidine-5-carboxamide, trihydrochloride salt;

4-(4-(2-Aminopyridin-4-yloxy)-3-fluorophenylamino)-N-(2,4-difluorophenyl)-2-(piperidin-1-yl)pyrimidine-5-carboxamide, trihydrochloride salt;

4-(4-(2-Aminopyridin-4-yloxy)-3-fluorophenylamino)-2-(benzylamino)-N-(2,4-difluorophenyl)pyrimidine-5-carboxamide, trihydrochloride salt;

4-(4-(2-Aminopyridin-4-yloxy)-3-fluorophenylamino)-N-(2,4-difluorophenyl)pyrimidine-5-carboxamide, bis(trifluoroacetic acid) salt;

4-(4-(2-Aminopyridin-4-yloxy)-3-fluorophenylamino)-N-(2,4-difluorophenyl)-2-methoxypyrimidine-5-carboxamide, dihydrochloride salt;

4-(4-(2-Aminopyridin-4-yloxy)-3-fluorophenylamino)-N-(2,4-difluorophenyl)-2-hydroxypyrimidine-5-carboxamide, dihydrochloride salt;

3-(4-(2-Aminopyridin-4-yloxy)-3-fluorophenylamino)-N-(2,4-difluorophenyl)pyrazine-2-carboxamide, bis(trifluoroacetic acid) salt; and 3-(4-(1H-Pyrrolo[2,3-b]pyridin-4-yloxy)-3-fluorophenylamino)-N-(2,4-difluorophenyl)pyrazine-2-carboxamide bis(trifluoroacetic acid) salt.

* * * * *

UNITED STATES PATENT AND TRADEMARK OFFICE
CERTIFICATE OF CORRECTION

PATENT NO. : 7,547,782 B2
APPLICATION NO. : 11/529875
DATED : June 16, 2009
INVENTOR(S) : Robert Borzilleri et al.

It is certified that error appears in the above-identified patent and that said Letters Patent is hereby corrected as shown below:

In the Claims:

Claim 1, col. 90, line 45, delete "aryalkyl," and insert -- arylalkyl, --;

Claim 1, col. 91, lines 60-65, delete " 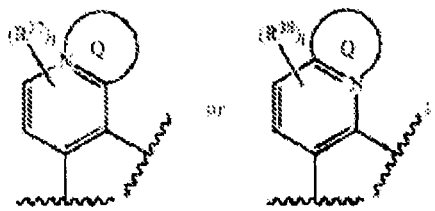 " and insert 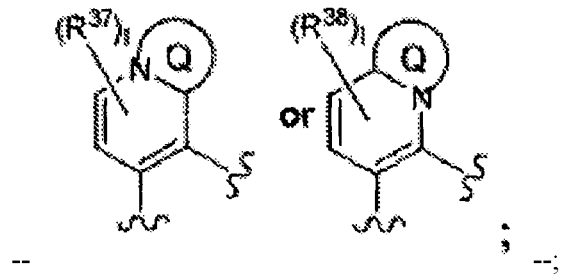 --;

Claim 1, col. 93, line 50, delete "$SOR^{127}$" and insert -- $SOR^{127}$, --;

Signed and Sealed this

First Day of June, 2010

David J. Kappos
*Director of the United States Patent and Trademark Office*

CERTIFICATE OF CORRECTION (continued)
U.S. Pat. No. 7,547,782 B2

Claim 5, col. 94, lines 60-65, delete " 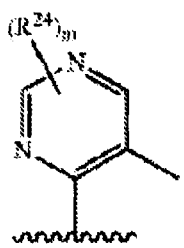 " and insert -- 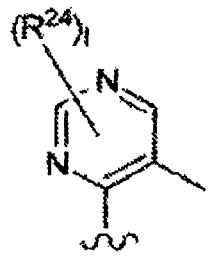 --;

Claim 7, col. 95, line 22, delete "alkylamino," and insert -- alkylaminoalkyl, --;

Claim 7, col. 95, line 23, before "or" delete "arylalkylamino";

Claim 12, col. 95, line 56, delete "aryalkyl," and insert -- arylalkyl, --;

Claim 12, col. 96, line 9, delete "aryalkyl," and insert -- arylalkyl, --;

Claim 12, col. 96, lines 45-50, delete " 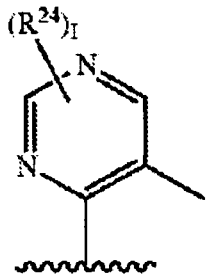 " and insert -- 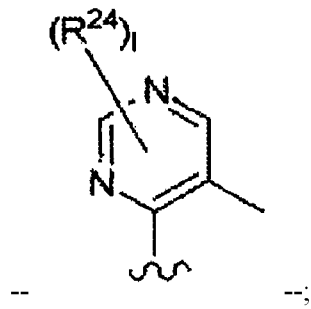 --;

Claim 12, col. 96, line 67, delete "R⁵⁷R⁵⁸," and insert -- $R^{57}$, $R^{58}$, --; and Claim 17, col. 98, line 6, delete "bis(triflouroacetic acid)" and insert -- bis(trifluoroacetic acid) --.